US012060393B2

(12) United States Patent
Kalyanasundaram

(10) Patent No.: US 12,060,393 B2
(45) Date of Patent: *Aug. 13, 2024

(54) VACCINE AND METHODS FOR DETECTING AND PREVENTING FILARIASIS

(71) Applicant: The Board of Trustees of the University of Illinois, Urbana, IL (US)

(72) Inventor: Ramaswamy Kalyanasundaram, Rockford, IL (US)

(73) Assignee: THE BD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 494 days.

This patent is subject to a terminal disclaimer.

(21) Appl. No.: 16/116,203

(22) Filed: Aug. 29, 2018

(65) Prior Publication Data

US 2019/0040108 A1 Feb. 7, 2019

Related U.S. Application Data

(63) Continuation of application No. 14/798,945, filed on Jul. 14, 2015, now Pat. No. 10,072,054, which is a continuation-in-part of application No. 13/885,168, filed as application No. PCT/US2011/059501 on Nov. 7, 2011, now abandoned.

(60) Provisional application No. 61/522,079, filed on Aug. 10, 2011, provisional application No. 61/449,954, filed on Mar. 7, 2011, provisional application No. 61/413,681, filed on Nov. 15, 2010.

(51) Int. Cl.
| | |
|---|---|
| *C07K 14/435* | (2006.01) |
| *A61K 39/00* | (2006.01) |
| *C12N 9/08* | (2006.01) |
| *G01N 33/569* | (2006.01) |

(52) U.S. Cl.
CPC ...... *C07K 14/4354* (2013.01); *A61K 39/0003* (2013.01); *C12N 9/0065* (2013.01); *G01N 33/56966* (2013.01); *A61K 2039/53* (2013.01); *A61K 2039/545* (2013.01); *A61K 2039/55505* (2013.01); *A61K 2039/70* (2013.01); *C07K 2319/00* (2013.01); *C07K 2319/40* (2013.01); *G01N 2333/4353* (2013.01); *G01N 2469/10* (2013.01); *G01N 2469/20* (2013.01); *Y02A 50/30* (2018.01)

(58) Field of Classification Search
CPC ............ C07K 14/4354; C07K 2319/40; A61K 39/0003; A61K 2039/53; A61K 2039/545; A61K 2039/55505; A61K 2039/70; C12N 9/0065; G01N 33/56966; G01N 2333/4353; G01N 2469/10; G01N 2469/20; Y02A 50/30
See application file for complete search history.

(56) References Cited

PUBLICATIONS

Ellis (Vaccines, W.B. Saunders Company, Chapter 29, 1988, pp. 568-574).*
Boslego et al (Vaccines and Immunotherapy, 1991, Chapter 17).*
Anand et al. "Comparison of Immunogenicity, Protective Efficacy of Single and Cocktail DNA Vaccine of *Brugia malayi* Abundant Larval Transcript (ALT-2) and Thioredoxin Peroxidase (TPX) in Mice" Acta Tropica 2008 107:106-112.
Babayan et al. "Vaccination against Filarial Nematodes with Irradiated Larvae Provides Long-Term Protection against the Third Larval Stage but not against subsequent Life Cycle Stages" International Journal for Parasitology 2006 36:903-914.
Bottazzi, et al. "An Ounce of Prevention on a Budget: a Nonprofit Approach to Developing Vaccines Against Neglected Diseases" Expert Review of Vaccines 2006 5(2):189-198.
Bowie et al. "Deciphering the Message in Protein Sequences: Tolerance to Amino Acid Substitutions" Science 1990 257:1306-1310.
Chenthamarakshan, et al. "Immunoprophylactic Potential of a 120 kDa Brugia malayi Adult Antigen Fraction, BmA-2, in Lymphatic Filariasis" Parasite Immunology 1995 17(6):277-285.
Cookson et al. "Identification of the Major Soluble Cuticular Glycoprotein of Lymphatic Filarial Nematode Parasites (gp29) as a Secretory Homolog of Glutathione Peroxidase" Proceedings of the National Academy of Sciences USA 1992 89:5837-5841.
Dash et al. "Granuloma Formation around Filarial Larvae Triggered by Host Responses to an Excretory/Secretory Antigen" Infection and Immunity 2011 79(2):838-845.
Dissanayake et al. "Differential Recognition of Microfilarial Chitinase, a Transmission-Blocking Vaccine Candidate Antigen, by Sera from Patients with Brugian and Bancroftian Filariasis" American Journal of Tropical Medicine and Hygeine 1995 53:289-294.
Gnanasekar et al. "Novel Phage Display-Based Subtractive Screening to Identify Vaccine Candidates of *Brugia malayi*" Infection and Immunity 2004 72(8):4707-4715.
Gnanasekar et al. "Identification and Cloning of a Novel Tetraspanin (TSP) Homologue from *Brugia malayi*" DNA Sequence 2008 19(2):151-156.
Gnanaseker et al. "A Novel Small Heat Shock Protein 12.6 (HSP12.6) from *Brugia malayi* Functions as a Human IL-10 Receptor Binding Protein" Molecular and Biochemical Parasitology 2008 159:98-103.
Greenspan, N.S. & Di Cera, E. "Defining Epitopes: It's Not as Easy as it Seems" Nature Biotechnology 1999 17:936-937.
Gregory et al., "The Abundant Larval Transcript-1 and -2 Genes of *Brugia malayi* Encode Stage-Specific Candidate Vaccine Antigens for Filariais" Infection and Immunity 2000 68(7):4174-4179.
Kron et al. "An Immunodominant Antigen of *Brugia malayi* is an Asparaginyl-tRNA Synthetase" FEBS Letters 1995 374:122-124.

(Continued)

*Primary Examiner* — Robert A Zeman
(74) *Attorney, Agent, or Firm* — Licata & Tyrrell P.C.

(57) ABSTRACT

The present invention is a multivalent vaccine for immunizing an animal against filariasis. In some embodiments, the antigens of the multivalent vaccine are protein-based, DNA-based, or a combination thereof. This invention also provides a method and kit for detecting a filarial nematode and determining vaccine efficacy.

3 Claims, 2 Drawing Sheets
Specification includes a Sequence Listing.

(56) References Cited

PUBLICATIONS

Li et al. "Identification of Paramyosin as a Potential Protective Antigen Against *Brugia malayi* Infection in Jirds" Molecular and Biochemical Parasitology 1991 49:315-323.

Li et al. "Vaccination with Recombinant Filarial Paramyosin Induces Partial Immunity to *Brugia malayi* Infection in Jirds." The Journal of Immunology 1993 150(5):1881-1885.

Maizels et al. "Cross-reactive surface antigens on three stages of *Brugia malayi, B. pahangi* and *B. timori*" Parasitology 1983 87:249-263.

Maizels et al. "Antigenic Analysis of *Brugia timori*, a Filarial Nematode of Man: Initial Characterization by Surface Radioiodination and Evaluation of Diagnostic Potential" Clinical & Experimental Immunology 1983 51:269-277.

Maizels et al. "Immunological Genomics of *Brugia malayi*: Filarial Genes Implicated in Immune Evasion and Protective Immunity" Parasite Immunology 2001 23:327-344.

Makepeace et al. "Immunisation with a Multivalent, Subunit Vaccine Reduces Patent Infection in a Natural Bovine Model of Onchocerciasis during Intense Field Exposure" Plos One 2009 3(11):e544.

Rahman et al. "Pan LF-ELISA Using BmRI and BmSXP Recombinant Antigens for Detection of Lymphatic Filariasis" Filaria Journal 2007 6:10.

Samykutty et al. "Multivalent Vaccine for Lymphatic Filariasis" Procedia in Vaccinology 2010 3:12-18.

Selkirk et al. "Heat Shock Cognate 70 is a Prominent Immunogen in Brugian Filariasis" The Journal of Immunology 1989 143:299-308.

Thirugnanam et al. "*Brugia malayi*: Comparison of Protective Immune Responses Induced by Bm-alt-2 DNA, Recombinant Bm-ALT-2 Protein and Prime-Boost Vaccine Regimens in a Jird Model" Experimental Parastiology 2007 116 (4):483-491.

Veerapathran et al. "Evaluation of *Wuchereria bancrofti* GST as a Vaccine Candidate for Lymphatic Filariasis" PLoS Neglected Tropical Diseases 2009 3(6):e457.

International Search Report and Written Opinion from PCT/US2011/059501, May 30, 2012, PCT.

International Preliminary Report on Patentability from PCT/US2011/059501, May 30, 2013, PCT.

EP Search Report from EPO application 11841437.4, Apr. 29, 2014, EP.

* cited by examiner

VACCINE AND METHODS FOR DETECTING AND PREVENTING FILARIASIS

INTRODUCTION

This application is a continuation of U.S. patent application Ser. No. 14/798,945, filed Jul. 14, 2015, issued as U.S. Pat. No. 10,072,054 on Sep. 11, 2018, which is continuation-in-part application of U.S. patent application Ser. No. 13/885,168, filed May 23, 2013, now abandoned, which is the National Stage of International Application No. PCT/US2011/059501, filed Nov. 7, 2011; which claims the benefit of priority from U.S. Provisional Application Ser. No. 61/413,681, filed Nov. 15, 2010; U.S. Provisional Application Ser. No. 61/449,954, filed Mar. 7, 2011; and U.S. Provisional Application Serial Ser. No. 61/522,079, filed Aug. 10, 2011, the contents of which are incorporated herein by reference in their entireties.

This invention was made with government support under contract number 5R01AI064745-04 awarded by the National Institutes of Health. The government has certain rights in the invention.

BACKGROUND

Lymphatic filariasis caused by the filarial nematodes *Wuchereria bancrofti*, *Brugia malayi*, and *Brugia timori*, affects more than 120 million people worldwide (WHO (1992) *World Health Organ. Tech. Rep. Ser.* 821:1-71). Mass drug administration program by the World Health Organization, is significantly reducing the incidence rate of lymphatic filariasis in many parts of the world (Hotez (2009) *Clin. Pharmacol. Ther.* 85(6):659-64). Nevertheless, lack of effectiveness to the mass drug administration has been reported from several endemic regions mainly due to non-compliance (Babu & (2008) *Trans. R. Soc. Trop. Med. Hyg.* 102(12):1207-13; El-Setouhy, et al. (2007) *Am. J. Trop. Med. Hyg.* 77(6):1069-73). In addition, drug resistance has been reported to at least one of the drugs in the mass drug combination (Horton (2009) *Ann. Trop. Med. Parasitol.* 103(1):S33-40; Schwab, et al. (2007) *Parasitology* 134(Pt 7):1025-40). Since yearly administration of the mass drugs is required for effective control, there is an alarming concern for selecting drug resistant parasites. Therefore, there is an immediate need for a multipronged approach in controlling this mosquito borne infection.

Vaccination is one strategy for controlling this infection and several subunit candidate vaccine antigens have been tested in laboratory animals with variable results (Bottazzi, et al. (2006) *Expert Rev. Vaccines* 5(2):189-98; Chenthamarakshan, et al. (1995) *Parasite Immunol.* 17(6):277-85; Dissanayake, et al. (1995) *Am. J. Trop. Med. Hyg.* 53(3):289-94; Li, et al. (1993) *J. Immunol.* 150(5):1881-5; Maizels, et al. (2001) *Int. J. Parasitol.* 31(9):889-98; Thirugnanam, et al. (2007) *Exp. Parasitol.* 116(4):483-91; Veerapathran, et al. (2009) *PLoS Negl. Trop. Dis.* 3(6):e457). Lymphatic filariasis is a multicellular organism with complex life cycle and produce large array of host modulatory molecules. Thus, fighting against this infection with a single antigen vaccine can be difficult. By screening a phage display cDNA expression library of the *B. malayi* parasite with sera from immune individuals, several potential vaccine candidates were identified (Gnanasekar, et al. (2004) *Infect. Immun.* 72(8):4707-15). However, a varying degree of protection was achieved with each of the candidate vaccine antigens when given as a DNA, protein or prime boost vaccine (Veerapathran, et al. (2009) supra).

SUMMARY OF THE INVENTION

The present invention is a fusion protein composed of (a) *Brugia malayi* Abundant Larval Transcript; and (b) *Brugia malayi* Small heat shock protein 12.6, *Brugia malayi* Tetraspanin, *Brugia malayi* Thioredoxin Peroxidase 2, or a combination thereof. In certain embodiments, the Abundant Larval Transcript comprises or consists of SEQ ID NO:37 or SEQ ID NO:39; the Small heat shock protein 12.6 comprises or consists of SEQ ID NO:49 or SEQ ID NO:64; the Tetraspanin comprises or consists of SEQ ID NO:45, SEQ ID NO:63 or SEQ ID NO:77; and the Thioredoxin Peroxidase 2 comprises or consists of SEQ ID NO:71. In other embodiments, the fusion protein comprises or consists of SEQ ID NO:70; SEQ ID NO:73 or SEQ ID NO:74. A recombinant vector encoding the fusion protein, a host cell containing said vector and a vaccine containing the fusion protein are also provided, as is a method for immunizing an animal against filariasis.

The invention also provides a vaccine containing (a) an Abundant Larval Transcript of SEQ ID NO:37 or SEQ ID NO:39; and (b) a Small heat shock protein 12.6 of SEQ ID NO:49 or SEQ ID NO:64; a Tetraspanin of SEQ ID NO:45, SEQ ID NO:63 or SEQ ID NO:77; a Thioredoxin Peroxidase 2 of SEQ ID NO:71; or a combination thereof. In one embodiment, the the proteins of (a) and (b) are expressed as a fusion protein. In another embodiment, the vaccine further includes an adjuvant. A method for using the vaccine to immunize an animal against filariasis is also provided.

This invention further provides an assay and kit for detecting a filarial nematode. The method of the invention includes the steps of contacting a biological sample, in vitro, with one or more binding agents against filarial nematode proteins selected from the group of ALT2, TSP, VAL-1, TPX2 and HSP or fragments thereof; and detecting binding between the binding agents and the filarial nematode proteins, wherein the presence of binding between the binding agents and the filarial nematode proteins indicates the presence of a filarial nematode. In some embodiments, the biological sample is from a human subject and the method further includes the step of treating the subject for filariasis. In addition to one or more binding agents against filarial nematode proteins selected from the group of ALT2, TSP, VAL-1, TPX2 and HSP or fragments thereof, the kit of the invention includes a device with a solid surface.

This invention also provides an assay and kit for determining the determining the presence of antibodies to filarial nematode proteins. The method of the invention includes the steps of contacting one or more filarial nematode proteins selected from the group of ALT2, TSP, VAL-1, TPX2 and HSP, or fragments thereof, with a biological sample suspected of containing antibodies to one or more of the filarial nematode proteins; and detecting binding between the one or more filarial nematode proteins and antibodies in the biological sample, wherein the presence of antibodies to the one or more filarial nematode proteins is indicative of efficacy of a vaccine to the filarial nematode, prior exposure to filarial proteins, or an existing infection with a filarial nematode. In one embodiment, the one or more of the filarial nematode proteins are present on one or more solid surfaces or particles. In addition to one or more filarial nematode proteins selected from the group of ALT2, TSP, VAL-1, TPX2 and HSP or fragments thereof, the kit of the invention includes a device with one or more solid surfaces.

DETAILED DESCRIPTION OF THE INVENTION

Figure 1:
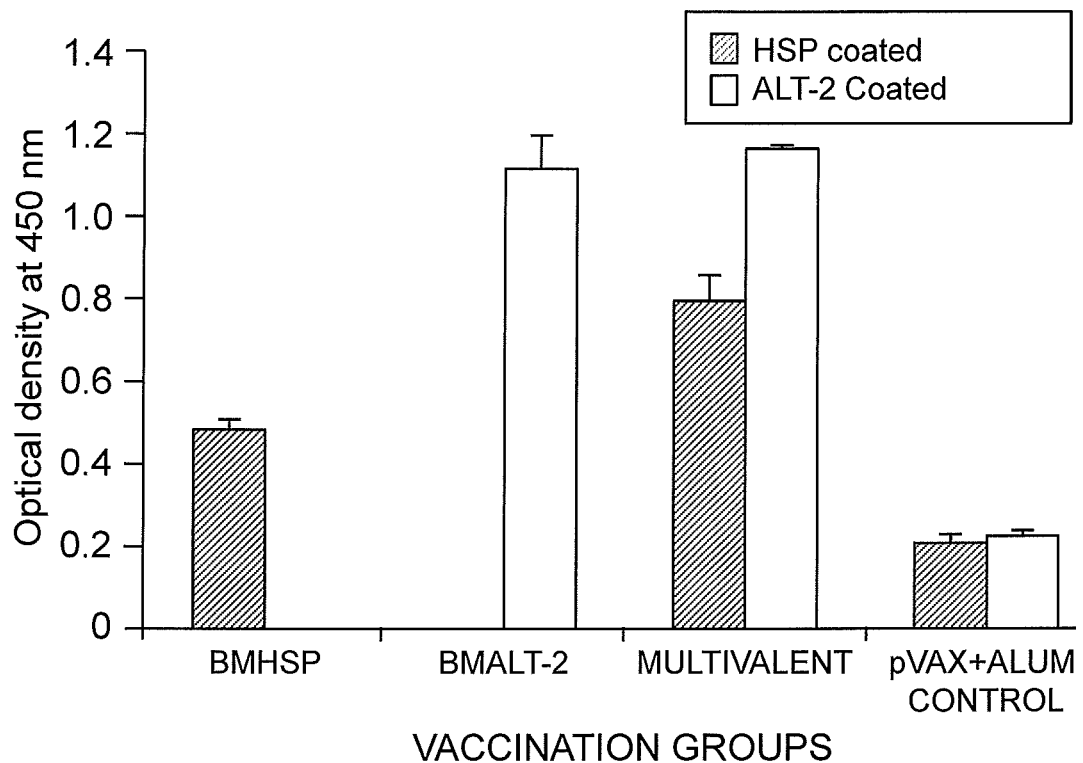
FIG. 1 shows the titer of anti-BmHSP and anti-BmALT2 IgG antibodies in the sera of vaccinated mice. 6-week-old balb/c mice were immunized using a prime boost approach with a monovalent vaccine (Bmhsp prime and rBmHSP boost or Bmalt2 prime and rBmALT2 boost) and multivalent vaccine (Bmhsp/Bmalt2 prime and rBmHSP and rBmALT2 boost). Titer of IgG antibodies were measured in the sera using an indirect ELISA. The data presented is the antibody titer 2 weeks after the last booster. Results show that both bivalent and multivalent vaccines induce significant IgG antibodies against each of the component antigens. The findings also show that the antigens in the monovalent and multivalent formulations act synergistically in boosting the immune responses. N=5. Statistically significant **$p<0.001$, *$p<0.05$. Values represented are mean±SD.

A multivalent vaccine for filariasis has now been developed. Combinations of antigens, such as Abundant Larval Transcript (ALT2), Tetraspanin (TSP), Small heat shock protein (HSP) 12.6, Vespid Venom Allergen homologue-Like protein (VAL-1), Glutathione S-Transferase (GST), and Thioredoxin Peroxidase 2 (TPX-2) were prepared into one hybrid DNA antigen or one fusion protein antigen. When tested in experimental animals (i.e., mouse, jirds, mastomys), the combination of hybrid DNA plus hybrid protein vaccination gave 100% protection. Hybrid protein alone vaccine gave >80% protection. Accordingly, the present invention features fusion protein-based and DNA-based vaccines composed of filarial nematode antigens or nucleic acids encoding the same and use of the vaccines to prevent or control filariasis in humans and animals. In addition to vaccination, the present invention also provides assays and kits for detecting the presence of a filarial nematode.

For the purposes of the present invention, a multivalent or polyvalent vaccine refers to a vaccine prepared from several antigens. According to some embodiments, the antigen is a nucleic acid molecule, which is referred to herein as a "DNA-based" antigen. According to other embodiments, the antigen is a protein or polypeptide, which is referred to herein as "protein-based" antigen. A multivalent vaccine of the invention can be composed of two, three, four, five, six or up to ten antigens or their fragments in various permutation combinations. In particular embodiments, the multivalent vaccine is composed of two, three or four antigens. In some embodiments, the multivalent vaccine is composed of solely of protein antigens. In other embodiments, the multivalent vaccine is composed solely of DNA-based antigens. In yet other embodiments, the multivalent vaccine is composed of a mixture of protein- and DNA-based antigens.

Antigens of the instant invention can be provided or expressed from a single nucleic acid molecule containing, e.g., internal ribosome entry sites between the antigens. Moreover, the antigens of the multivalent vaccine of this invention can be covalently attached to form a hybrid or chimeric molecule or fusion protein, wherein the antigens are immediately adjacent to one another (e.g., an in-frame fusion with or without a short spacer). Alternatively, antigens of the instant invention can be provided as a mixture of individual antigens. Moreover, it is contemplated that the instant vaccine can be composed of a hybrid molecule containing, e.g., two antigens, in admixture with a third non-covalently attached antigen. By way of illustration, a multivalent vaccine of the invention can be composed of a chimeric TSP-HSP protein in admixture with a nucleic acid molecule encoding ALT2.

In one embodiment, the antigens of the multivalent vaccine are different proteins from one species of filarial nematode. As an example of this embodiment, the multivalent vaccine is composed of ALT2, HSP, and TSP and/or TPX2 or GST antigens isolated from one or more strains of *B. malayi*. In another embodiment, the antigens are the same, but from different species of filarial nematodes. As an example of this embodiment, the multivalent vaccine is composed of the ALT2 antigen isolated from *W. bancrofti*, *B. malayi*, *B. timori*, *O. volvulus* and *L. loa*. In yet a further embodiment, the multivalent vaccine is composed of a combination of different antigens from different species of filarial nematodes. By way of illustration, the multivalent vaccine can be composed of the ALT2 antigen isolated from *W. bancrofti*, *O. volvulus* and *L. boa* and the HSP antigen isolated from *B. malayi* and *B. timori*.

For preparing multivalent DNA vaccines or multivalent recombinant DNA vaccines, the DNA sequence of the gene of interest (also used interchangeably as DNA molecule) need not contain the full length of DNA encoding the corresponding protein. Likewise, when preparing fusion protein vaccines or multivalent recombinant protein vaccines, the protein sequence need not contain the full length protein. In most cases, a fragment of the protein or gene which encodes an epitope region is sufficient for immunization. The DNA/protein sequence of an epitope region can be found by sequencing the corresponding part of the gene from various strains or species and comparing them. The major antigenic determinants are likely to be those showing the greatest heterology. Also, these regions are likely to lie accessibly in the conformational structure of the proteins. One or more such fragments of proteins or genes encoding the antigenic determinants can be prepared by chemical synthesis or by recombinant DNA technology. These fragments of proteins or genes, if desired, can be linked together or linked to other proteins or DNA molecules, respectively.

As described herein, the ALT2, TSP, VAL-1, GST and HSP antigens were identified as providing protection against infection by filaria larvae. Accordingly, in particular embodiments, the instant vaccine (e.g., fusion protein) includes the ALT2, TSP, VAL-1, TPX2, GST and/or HSP protein antigens and/or nucleic acid molecules encoding the ALT2, TSP, VAL-1, TPX2, GST and/or HSP protein, or fragments thereof. Protein and nucleic acid sequences for these antigens are available in the art under the GENBANK accession numbers listed in Table 1.

sequences for eliciting an immune response in an animal. In certain embodiments, the ALT2 protein of the invention is a *B. malayi* ALT2 protein or fragment comprising or consisting of the sequence VSESDEEFDDSAADDTDDSEA-GGGSEGGDEYVT (SEQ ID NO:78) and/or EFVETDGKKKECSSHEACYDQREPQ (SEQ ID NO:79), which, based upon the Bepipred Linear Epitope Prediction method (Larsen, et al. (2006) *Immunome Res.* 2:2), are predicted B-cell epitopes. In other embodiments, the HSP protein of the invention is a *B. malayi* HSP protein or fragment comprising or consisting of the sequence WSAEQWDWPLQH (SEQ ID NO:80) and/or KLPSDVDTKTL (SEQ ID NO:81), which are predicted B-cell epitopes. In further embodiments, the TSP protein of the invention is a *B. malayi* TSP protein or fragment comprising or consisting of the sequence KTGESEDEMQ (SEQ ID NO:82), which is a predicted B-cell epitope. In yet a further embodiment, the TPX2 protein of the invention is a *B. malayi* TPX2 protein or fragment comprising or consisting of the sequence FIGQPAPNFKT (SEQ ID NO:83)

TABLE 1

| Antigen | Source | Protein | SEQ ID NO: | Nucleic Acid | SEQ ID NO: |
|---|---|---|---|---|---|
| ALT2 | *B. malayi* | P90708 | 37 | BMU84723 | 38 |
|  |  | XP_001896203 | 39 | XM_001896168 | 40 |
|  | *W. bancrofti* | AAC35355 | 41 | AF084553 | 42 |
|  | *L. loa* | XP_003151340 | 43 | XM_003151292 | 44 |
| TSP | *B. malayi* | ABN55911 | 45 | EF397425 | 46 |
|  | *L. loa* | XP_003136177 | 47 | XM_003136129 | 48 |
| HSP | *B. malayi* | AAU04396 | 49 | AY692227 | 50 |
|  | *O. volvulus* | CAA48633 | 51 | X68669 | 52 |
|  | *L. loa* | XP_003139338 | 53 | XM_003139290 | 54 |
| VAL-1 | *B. malayi* | AAB97283 | 55 | AF042088 | 56 |
|  | *W. bancrofti* | AAD16985 | 57 | AF109794 | 58 |
|  | *O. volvulus* | AAB69625 | 59 | AF020586 | 60 |
|  | *L. loa* | XP_003146897 | 61 | XM_003146849 | 62 |
| TPX2 | *B. malayi* | Q17172 | 71 | U47100 | 72 |
| GST | *W. bancrofti* | AA045827 | 85 | AY195867 | 86 |

In addition, the nucleotide sequence encoding *O. volvulus* TSP can be found under GENBANK Accession No. JN861043. The protein antigens and nucleic acid molecules of the invention can be used as full length molecules or less than full length molecules. In this respect, the present invention further includes the use of fragments of the above-referenced protein antigens and nucleic acid molecules. Fragments are defined herein as 20, 30, 40, 50, 60, 70, 80, 90, 100, 150, or 200 amino acid residue portions of full-length protein antigens (e.g., those listed in Table 1) or 60, 90, 120, 150, 180, 210, 240, 270, 300, 350, or 600 nucleotide portion of full-length nucleic acid molecules (e.g., those listed in Table 1). Exemplary protein fragments include the large extracellular loop (LEL) domain of TSP (see, e.g., the LEL domain of *B. malayi* TSP of SEQ ID NO:63 or SEQ ID NO:77) and N-terminal deletion of HSP 12.6 (cHSP; see, e.g., the *B. malayi* HSP fragment of SEQ ID NO:64), as well as the nucleic acid molecules encoding the same (see, SEQ ID NO:65 and SEQ ID NO:66, respectively). An exemplary fusion protein containing ALT2, HSP and TSP protein sequences is set forth in SEQ ID NO:70. An exemplary fusion protein containing ALT2, HSP and TPX2 protein sequences is set forth in SEQ ID NO:73. An exemplary fusion protein containing ALT2, HSP, TSP and TPX2 protein sequences is set forth in SEQ ID NO:74.

In particular embodiments, the protein or protein fragments of this invention have one or more antigenic and/or GEVCPANWHPGSETIKPGVKESKA (SEQ ID NO:84), which are predicted B-cell epitopes.

With respect to certain embodiments of the invention, the multivalent vaccine of the invention includes other known antigens from *W. bancrofti*, *B. malayi*, *O. volvulus*, *L. loa* and *B. timori*. Examples of other suitable antigens include, but are not limited to, glutathione peroxidase (see Cookson, et al. (1992) *Proc. Natl. Acad. Sci. USA* 89:5837-5841; Maizels, et al. (1983) *Parasitology* 87:249-263; Maizels, et al. (1983) *Clin. Exp. Immunol.* 51:269-277); recombinant antigen (BmR1; see Noordin, et al. (2004) *Filaria J.* 3:10); class II aminoacyl-tRNA synthetase (see Kron, et al. (1995) *FEBS Lett.* 374:122-4); heat shock cognate 70 (hsc70) protein (see Selkirk, et al. (1989) *J. Immunol.* 143:299-308); and paramyosin (see Li, et al. (1991) *Mol. Biochem. Parasitol.* 49:315-23). In some embodiments, the antigen is obtained from a filarial nematode selected from the group of *W. bancrofti*, *B. malayi*, *O. volvulus*, *L. loa* and *B. timori*.

According to the present invention, the antigens of the fusion protein and vaccine are isolated from a filarial nematode. In this respect, an isolated nucleic acid molecule or protein is a nucleic acid molecule or protein that has been removed from its natural milieu (i.e., that has been subjected to human manipulation). As such, "isolated" does not reflect the extent to which the nucleic acid molecule or protein has been purified. In particular embodiments, the antigens are purified (e.g., purified to greater than 95% homogeneity). An isolated and optionally purified nucleic acid molecule or protein of the present invention can be obtained from its natural source or produced using recombinant DNA technology (e.g., polymerase chain reaction (PCR) amplification or cloning) or chemical synthesis. Isolated nucleic acid molecules and proteins can also include, for example, natural allelic variants or isomers that induce an immune response in the host.

One embodiment of the present invention includes a recombinant vector, which includes at least one isolated nucleic acid molecule of the present invention, inserted into a vector capable of delivering the nucleic acid molecule into a host cell. Such a vector contains heterologous nucleic acid sequences, that are nucleic acid sequences that are not naturally found adjacent to nucleic acid molecules of the present invention and that preferably are derived from a species other than the species from which the nucleic acid molecule(s) are derived. The vector can be either prokaryotic or eukaryotic, and typically is a virus or a plasmid. Recombinant vectors can be used in the cloning, sequencing, and/or otherwise manipulating the nucleic acid molecules of the present invention.

The present invention also includes an expression vector, which includes a nucleic acid molecule of the present invention in a recombinant vector that is capable of expressing the nucleic acid molecule when transformed into a host cell. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as *B. malayi* transcription control sequences.

Recombinant molecules of the present invention may also contain (a) secretory signals (i.e., signal segment nucleic acid sequences) to enable an expressed protein of the present invention to be secreted from the cell that produces the protein and/or (b) fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant host cell harboring one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS- 7) cells, and Vero cells. Particularly preferred host cells are *Escherichia coli*, including *E. coli* K-12 derivatives; *Salmonella typhi; Salmonella typhimurium; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention and one or more transcription control sequences, examples of which are disclosed herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein. Moreover, while non-codon-optimized sequences may be used to express fusion proteins in host cells such as *E. coli* (see Table 1), in embodiments pertaining to DNA vaccines, the nucleic acid molecule may be codon-optimized to facilitate expression in mammalian cells. In this respect, codon-optimized sequences for BmALT2, N-terminal deleted HSP 12.6 (cHSP) of *B. malayi*, and LEL domain of *B. malayi* Tetraspanin are set forth in SEQ ID NO:67, SEQ ID NO:68, and SEQ ID NO:69, respectively. Moreover, to facilitate expression of one or more of the recombinant proteins in a recombinant host cell, the protein sequence can be manipulated. By way of illustration, the insertion of a glycine residue after the N-terminal methionine residue of the *B. malayi* ALT2 protein was found to improve expression of this protein in *E. coli*.

Isolated protein-based antigens of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a protein of the present invention. Such medium typically includes an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

Recovery of proteins of invention can include collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in substantially pure form thereby allowing for the effective use of the protein as a therapeutic composition. A therapeutic composition for animals, for example, should exhibit no substantial toxicity and preferably should be capable of stimulating the production of antibodies in a treated animal.

One embodiment of the present invention is an immunogenic composition or vaccine that, when administered to an animal in an effective manner, is capable of protecting that animal from filariasis caused by a filarial nematode. Immunogenic compositions include two or more of the following protective molecules, an isolated antigenic protein of the present invention, an isolated nucleic acid molecule of the present invention, and hybrids and mixtures thereof. As used herein, the vaccine of the invention is protective in that, when administered to an animal in an effective manner, it is able to treat, ameliorate, and/or prevent disease caused by a filarial nematode including, but not limited to, *W. bancrofti, B. malayi, O. volvulus, L. loa, Mansonella streptocerca, Dracunculus medinensis, M. perstans, M. ozzardi*, and/or *B. timori*. Vaccines of the present invention can be administered to any animal susceptible to such therapy, preferably to mammals, and more preferably to humans, pets such as cats, and economic food animals and/or zoo animals. The preferred animals to protect against elephantiasis include humans.

In one embodiment, a vaccine of the present invention when administered to the host can develop antibodies that can kill the parasites in the vector in which the filarial nematode develops, such as in a mosquito when they feed the host.

In order to protect an animal from disease caused by a filarial nematode, an immunogenic composition of the present invention is administered to the animal in an effective manner such that the composition is capable of protecting that animal from a disease caused by the filarial nematode.

Compositions of the present invention can be administered to animals prior to infection in order to prevent infection (i.e., as a preventative vaccine) and/or can be administered to animals after infection in order to treat disease caused by the filarial nematode (i.e., as a therapeutic vaccine).

Compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the vaccine can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and *Leishmania* elongation initiating factor (LEIF)); bacterial components (e.g., endotoxins, in particular superantigens, exotoxins and cell wall components); toll-like receptor agonists (example TLR4 agonists); aluminum-based salts; calcium-based salts; silica; polynucleotides; toxoids; serum proteins, viral coat proteins; block copolymer adjuvants (e.g., Hunter's TITERMAX adjuvant (VAXCEL, Inc. Norcross, GA), Ribi adjuvants (Ribi ImmunoChem Research, Inc., Hamilton, MT); and saponins and their derivatives (e.g., QUIL A (Superfos Biosector A/S, Denmark). Protein adjuvants of the present invention can be delivered in the form of the protein themselves or of nucleic acid molecules encoding such proteins using the techniques described herein.

In one embodiment of the present invention, a vaccine can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation includes a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation is capable of releasing a vaccine of the present invention into the blood of the treated animal at a constant rate sufficient to attain therapeutic dose levels of the composition to protect an animal from disease caused by a filarial nematode. The vaccine is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Vaccines of the present invention can be administered to animals prior to infection in order to prevent infection and/or can be administered to animals after infection in order to treat disease caused by a filarial nematode. For example, proteins, nucleic acids and mixtures thereof can be used as immunotherapeutic agents. Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein-based vaccine is from about 1 microgram (pg) to about 10 milligrams (mg) of protein-based vaccine per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 µg to about 1 mg of the vaccine per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

Wherein the vaccine includes a nucleic acid molecule, the vaccine can be administered to an animal in a fashion to enable expression of that nucleic acid molecule into a protective protein in the animal. Nucleic acid molecules can be delivered to an animal in a variety of methods including, but not limited to, administering a naked (i.e., not packaged in a viral coat or cellular membrane) nucleic acid as a genetic vaccine (e.g., as naked DNA molecules, such as is taught, for example in Wolff, et al. (1990) *Science* 247:1465-1468); or administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can include one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, including intramuscular, subcutaneous, intradermal, transdermal, intranasal and oral routes of administration. Moreover, it is contemplated that the vaccine can be delivered by gene gun, skin patch, electroporation, or nano-based delivery. In this respect, DNA-based and protein-based vaccines can be administered at the same time. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate-buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. Examples of methods to produce and use alphavirus recombinant virus vaccines are disclosed in PCT Publication No. WO 94/17813.

When administered to an animal, a recombinant virus vaccine of the present invention infects cells within the immunized animal and directs the production of a protective protein that is capable of protecting the animal from filariasis caused by filarial nematodes. By way of illustration, a single dose of a recombinant virus vaccine of the present invention can be from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral as routes of administration.

A recombinant cell vaccine of the present invention includes recombinant cells of the present invention that express a protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can include whole cells, cells stripped of cell walls or cell lysates.

As is known in the art, there are three groups of filarial nematodes, classified according to the niche within the body that they occupy: lymphatic filariasis, subcutaneous filariasis, and serous cavity filariasis. Lymphatic filariasis is caused by the worms *W. bancrofti, B. malayi* and *B. timori*. These worms occupy the lymphatic system, including the lymph nodes, and cause fever, lymphadenitis (swelling of the lymph nodes), lymphangitis (inflammation of the lymphatic vessels in response to infection), and lymphedema (elephantiasis). Subcutaneous filariasis is caused by *Loa loa* (the African eye worm), *Mansonella stretocerca, O. volvulus* and *Dracunculus medinensis*. These worms occupy the subcutaneous layer of the skin, in the fat layer, and present with skin rashes, urticarial papules, and arthritis, as well as hyper- and hypopigmentation macules. *Onchocerca volvulus* manifests itself in the eyes, causing "river blindness." Serous cavity filariasis is caused by the worms *M. perstans* and *M. ozzardi*, which occupy the serous cavity of the abdomen. Serous cavity filariasis presents with symptoms similar to subcutaneous filariasis, in addition to abdominal pain, because these worms are also deep tissue dwellers.

The efficacy of a vaccine of the present invention to protect an animal from filariasis caused by filarial nematodes can be tested in a variety of ways including, but not limited to, detection of protective antibodies (using, for example, proteins of the present invention), detection of cellular immunity within the treated animal, and/or challenge of the treated animal with the a filarial nematode to determine whether the treated animal is resistant to disease and fails to exhibit one or more signs of disease. Challenge studies can include implantation of chambers including filarial nematode larvae into the treated animal and/or direct administration of larvae to the treated animal. In one embodiment, therapeutic compositions can be tested in animal models such as mice, jirds (*Meriones unguiculatus*) and/or mastomys (e.g., *Mastomys natalensis*). Such techniques are known to those skilled in the art.

To detect the presence/amount of anti-filarial nematode antibodies, e.g., protective or neutralizing antibodies resulting from the vaccination of an animal, this invention also provides a method and kit for efficacy evaluation, as well as for detecting prior exposure to filarial proteins and/or infection with a filarial nematode. In accordance with such a method, one or more antigenic proteins/epitopes is contacted with a biological sample from an animal and binding between the antigenic proteins/epitopes and antibodies in the biological sample is quantitively or qualitatively determined as described herein, wherein the presence and/or amount of antibodies to the antigenic proteins/epitopes is indicative of vaccine efficacy, as well as prior exposure to filarial proteins or an existing infection with a filarial nematode. In certain embodiments, the method and kit use an array-based format in which serial dilutions of one or more antigens or epitopes are printed. In some embodiments, the one or more of the filarial nematode proteins are present on one or more solid surfaces or particles. In other embodiments, the one or more of the filarial nematode proteins are in an array so that the presence of multiple antibodies can be assessed in a single assay due to the multiplexing capability of an array-based approach. In this respect, the array can contain one or more of ALT2, TSP, VAL-1, TPX2, GST or HSP protein or an epitope thereof. In other embodiments, the array at least contains each of the proteins used in the vaccine. For example, to assay for protective or neutralizing antibodies against a vaccine containing HSP, ALT2 and TSP, the array would contain HSP, ALT2 and TSP, or a fusion protein thereof.

For testing for the presence of a filarial nematode, this invention also provides a method and kit for detecting a filarial nematode. The assay method generally includes the steps of contacting, in vitro, a biological sample with one or more binding agents against filarial nematode proteins selected from the group of ALT2, TSP, VAL-1, TPX2, GST and HSP or fragments thereof. The bound binding agents are then detected. The bound binding agents can be detected using automated detection of binding such as an image reader of an ELISA assay, and if a bound binding agent is detected, the data indicating that a bound binding agent has been detected can be transferred, e.g., to a computer display or on a paper print out. Detection of a filarial nematode protein indicates that the sample or subject from which the sample was obtained has filariasis. Therefore, detection allows selection of treatment options for the subject. Thus, in one embodiment, if one or more of ALT2, TSP, VAL-1, TPX2, GST and HSP is detected, the patient will be given a treatment suitable for filariasis, including but not limited to treatment with diethylcarbamazine, mebendazole, flubendazole, albendazole, ivermectin or a combination thereof.

A biological sample is any material to be tested for the presence or amount of a protein of interest (e.g., an antibody or antigen/epitope). The sample can be a fluid sample, preferably a liquid sample. Examples of liquid samples that may be tested in accordance with this invention include bodily fluids including blood, serum, plasma, saliva, urine, ocular fluid, semen, and spinal fluid. Viscous liquid, semi-solid, or solid specimens (e.g., human tissue, or mosquito or fly tissue) may be used to create liquid solutions, eluates, suspensions, or extracts that can be samples. In some embodiments, the biological sample is undiluted. In other embodiments, the sample is diluted or concentrated depending on the detection application.

In certain embodiments, one can concentrate the proteins in the sample by using a solid surface coated with a monoclonal antibody to capture the protein. The recovered captured proteins can then be analyzed using any suitable method described herein. The solid surface can be, e.g., beads, such as magnetic beads, polystyrene beads, or gold beads, or in an array or a microarray format using a glass, a plastic or a silicon chip. Such protein capture can be also a part of a channel in a microfluidic device.

Binding agents of use in this invention include an antibody, an antibody fragment, or an antibody derivative (e.g., an aptamer) which specifically binds to a cognate filarial nematode protein. Specific binding between two entities generally refers to an affinity of at least $10^6$, $10^7$, $10^8$, $10^9$, or $10^{10}$ M$^{-1}$. Affinities greater than $10^8$ M$^{-1}$ are desired to achieve specific binding.

When the binding agent is an antibody, the antibody can be produced by natural (i.e., immunization) or partial or wholly synthetic means. Antibodies can be monoclonal or polyclonal and include commercially available antibodies. An antibody can be a member of any immunoglobulin class, including any of the human classes: IgG, IgM, IgA, IgD, and IgE. Bispecific and chimeric antibodies are also encompassed within the scope of the present invention. Derivatives of the IgG class, however, are desirable. Further, an antibody can be of human, mouse, rat, goat, sheep, rabbit, chicken, camel, or donkey origin or other species which may be used to produce native or human antibodies (i.e., recombinant bacteria, baculovirus or plants).

For example, naturally-produced monoclonal antibodies can be generated using classical cloning and cell fusion techniques or techniques wherein B-cells are captured and nucleic acids encoding a specific antibody are amplified (see, e.g., U.S. Patent Application No. 20060051348). In such methods, a collection of proteins or an individual protein (e.g., a peptide or polypeptide) can be used for the initial immunization and in the context of antibody production is referred to herein as the antigen. The antigen of interest is typically administered (e.g., intraperitoneal injection) to wild-type or inbred mice (e.g., BALB/c) or rats, rabbits, chickens, sheep, goats, or other animal species which can produce native or human antibodies. The antigen can be administered alone, or mixed with an adjuvant. After the animal is boosted, for example, two or more times, the spleen or large lymph node, such as the popliteal in rat, is removed and splenocytes or lymphocytes are isolated and fused with myeloma cells using well-known processes, for example, see Kohler and Milstein ((1975) *Nature* 256:495-497) or Harlow and Lane (Antibodies: A Laboratory Manual (Cold Spring Harbor Laboratory, New York (1988)). The resulting hybrid cells are then cloned in the conventional manner, e.g., using limiting dilution, and the resulting clones, which produce the desired monoclonal antibodies, are cultured (see Stewart, S. (2001) Monoclonal Antibody Production. In: *Basic Methods in Antibody Production and Characterization*, Howard and Bethell (eds.), CRC Press, Boca Raton, FL, pp. 51-67).

Alternatively, antibodies can be derived by a phage display method. Methods of producing phage display antibodies are known in the art, e.g., see Huse, et al. ((1989) *Science* 246(4935):1275-81). Selection of antibodies is based on binding affinity to a protein or proteins of interest.

An antibody fragment encompasses at least a significant portion of the full-length antibody's specific binding ability. Examples of antibody fragments include, but are not limited to, Fab, Fab', F(ab')$_2$, scFv, Fv, dsFv, diabody, Fd fragments or microbodies. An antibody fragment can contain multiple chains which are linked together, for instance, by disulfide linkages. A fragment can also optionally be a multi-molecular complex. A functional antibody fragment will typically include at least about 50 amino acid residues and more typically will include at least about 200 amino acid residues. The antibody fragment can be produced by any means. For instance, the antibody fragment can be enzymatically or chemically produced by fragmentation of an intact antibody or it can be recombinantly-produced from a gene encoding the partial antibody sequence. Alternatively, the antibody fragment can be wholly or partially synthetically-produced.

Peptide aptamers which specifically bind to a protein are, in general, rationally designed or screened for in a library of aptamers (e.g., provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range).

Recombinant production of binding agents of this invention can be achieved using conventional molecular biology techniques and commercially available expression systems. Furthermore, binding agents can be produced using solid-phase techniques (see, e.g., Merrifield J. (1963) *J. Am. Chem. Soc.* 85:2149-2154; Seeberger (2003) *Chem. Commun.* (*Camb*) (10):1115-21). Protein synthesis can be performed using manual techniques or by automation. Automated synthesis can be achieved, for example, using Applied Biosystems 431A Peptide Synthesizer (Perkin Elmer, Boston, MA). Various fragments of a binding agent can be chemically-synthesized separately and combined using chemical methods to produce a full-length molecule.

Moreover combinatorial chemistry approaches can be used to produce binding agents (see, e.g., Lenssen, et al. (2002) *Chembiochem.* 3(9):852-8; Khersonsky, et al. (2003) *Curr. Top. Med. Chem.* 3(6):617-43; Anthony-Cahill and Magliery (2002) *Curr. Pharm. Biotechnol.* 3(4):299-315).

The binding agents described herein can be labeled. In some embodiments, the binding agent is an antibody labeled by covalently linking the antibody to a direct or indirect label. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties.

Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall (1980) *Methods of Enzymology* 70:419-439.

The proteins described herein (i.e., antibodies or antigens/epitopes) can be attached to a surface. Examples of useful surfaces on which the protein can be attached for diagnostic purposes include nitrocellulose, PVDF, polystyrene, nylon or other suitable plastic. The surface or support may also be a porous support (see, e.g., U.S. Pat. No. 7,939,342).

Further, the proteins of the invention can be attached to a particle or bead. For example, antibodies to the filarial nematode proteins or the filarial nematode proteins themselves can be conjugated to superparamagnetic microparticles, e.g., as used in LUMINEX-based multiplex assays.

The filarial nematode proteins of this invention may be isolated and/or purified or produced synthetically or using recombinant nucleic acid technology. The purification may be partial or substantial. With reference to filarial nematode protein fragments, the term "fragment" refers to a protein having an amino acid sequence shorter than that of the proteins described herein. Preferably, such fragments are at least 5 consecutive amino acids long or up to 35 amino acids long. In certain embodiments, the protein fragment includes at least one epitope. An "epitope" is a feature of a molecule, such as primary, secondary and/or tertiary peptide structure, and/or charge, that forms a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. In some embodiments, the protein fragment of the invention is a fragment of *B. malayi* ALT2 comprising or consisting of the epitope of SEQ ID NO:78. In other embodiments, the protein fragment of the invention is a fragment of *B. malayi* or *W. bancrofti* ALT2 comprising or consisting of the epitope of SEQ ID NO:79. In further embodiments, the protein fragment of the invention is a fragment of *B. malayi*, *W. bancrofti*, or *L. loa* HSP comprising or consisting of the epitope of SEQ ID NO:80 or SEQ ID NO:81. In certain embodiments, the protein fragment of the invention is a fragment of *B. malayi* TSP comprising or consisting of the epitope of SEQ ID NO:82. In other embodiments, the protein fragment of the invention is a fragment of *B. malayi* or *W. bancrofti* TPX2 comprising or consisting of the epitope of SEQ ID NO:83. In further embodiments, the protein fragment of the invention is a fragment of *B. malayi*, *W. bancrofti*, or *L.* boa HSP comprising or consisting of the epitope of SEQ ID NO:84.

The fragments of the invention can be isolated, purified or otherwise prepared/derived by human or non-human means. For example, epitopes can be prepared by isolating the filarial nematode protein fragment from a bacterial culture, or they can be synthesized in accordance with standard protocols in the art. Synthetic epitopes can also be prepared from amino acid mimetics, such as D isomers of natural occurring L amino acids or non-natural amino acids such as cyclohexylalanine.

In some embodiments, the filarial nematode protein or protein fragment is conjugated or fused to a high molecular weight protein carrier to facilitate antibody production. In some embodiments, the high molecular weight protein is bovine serum albumin, thyroglobulin, ovalbumin, fibrinogen, or keyhole limpet hemocyanin. A particularly preferred carrier is keyhole limpet hemocyanin.

Any suitable immunoassay method may be used, including those which are commercially available, to determine the level of at least one of the specific filarial nematode proteins, protein fragments or protective/neutralizing antibodies according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc. Various of the known immunoassay methods are reviewed, e.g., in *Methods in Enzymology* (1980) 70:30-70 and 166-198.

In some embodiments, the immunoassay method or assay includes a double antibody technique for measuring the level of the filarial nematode proteins or protein fragments in the biological sample. According to this method one of the antibodies is a "capture" antibody and the other is a "detector" antibody. The capture antibody is immobilized on a solid support which may be any of various types which are known in the art such as, for example, microtiter plate wells, beads, tubes and porous materials such as nylon, glass fibers and other polymeric materials. In this method, a solid support, e.g., microtiter plate wells, coated with a capture antibody, preferably monoclonal, raised against the particular protein of interest, constitutes the solid phase. The biological sample, which may be diluted or not, typically at least 1, 2, 3, 4, 5, 10, or more standards and controls are added to separate solid supports and incubated. When the protein of interest is present in the sample it is captured by the immobilized antibody which is specific for the protein in question. After incubation and washing, a detector antibody, e.g., a polyclonal rabbit anti-marker protein antibody, is added to the solid support. The detector antibody binds to the protein bound to the capture antibody to form a sandwich structure. After incubation and washing an anti-IgG antibody, e.g., a polyclonal goat anti-rabbit IgG antibody, labeled with an enzyme such as horseradish peroxidase (HRP) is added to the solid support. After incubation and washing a substrate for the enzyme is added to the solid support followed by incubation and the addition of an acid solution to stop the enzymatic reaction.

The degree of enzymatic activity of immobilized enzyme is determined by measuring the optical density of the oxidized enzymatic product on the solid support at the appropriate wavelength, e.g., 450 nm for HRP. The absorbance at the wavelength is proportional to the amount of protein of interest in the sample. A set of marker protein standards is used to prepare a standard curve of absorbance vs. filarial nematode protein concentration. This method is useful because test results can be provided in 45 to 50 minutes and the method is both sensitive over the concentration range of interest for each filarial nematode protein and is highly specific.

The standards may be positive samples containing various concentrations of the protein to be detected to ensure that the reagents and conditions work properly for each assay. The standards also typically include a negative control, e.g., for detection of contaminants. In some aspects of the embodiments of the invention, the positive controls may be titrated to different concentrations, including non-detectable amounts and clearly detectable amounts, and in some aspects, also including a sample that shows a signal at the threshold level of detection in the biological sample.

The method of the invention can be carried out in various assay device formats including those described in U.S. Pat. Nos. 6,426,050, 5,910,287, 6,229,603, and 6,232,114 to Aurora Biosciences Corporation. The assay devices used according to the invention can be arranged to provide a quantitative or a qualitative (present/not present) result. In some embodiments, the method includes the use of a microtiter plate or a microfluidic device format. The assays may also be carried out in automated immunoassay analyzers which are known in the art and which can carry out assays on a number of different samples. These automated analyzers include continuous/random access types. Examples of such systems are described in U.S. Pat. Nos. 5,207,987, 5,518,688, 6,448,089, and 6,814,933. Various automated analyzers that are commercially available include the OPUS® and OPUS MAGNUM® analyzers.

Another assay format which can be used according to the invention is a rapid manual test which can be administered at the point-of-care at any location. Typically, such point-of-care assay devices will provide a result which is either "positive," i.e., showing the protein is present, or "negative" showing that the protein is absent. Typically, a control showing that the reagents worked in general is included with such point-of-care system. Point-of-care systems, assays and devices have been well described for other purposes, such as pregnancy detection (see, e.g., U.S. Pat. Nos. 7,569,397 and 7,959,875). Accordingly, the invention also provides devices, such as point-of-care test strips and microfluidic devices to perform the in vitro assays of the present invention.

It should be recognized also that the assay devices used according to the invention can be provided to carry out one single assay for a particular protein or to carry out a plurality of assays, from a single volume of body fluid, for a corresponding number of different filarial nematode proteins or antibodies thereto. In some embodiments, an assay device of the latter type is one which can provide a semi-quantitative result for the filarial nematode protein or antibodies measured according to the invention, i.e., one or more of ALT2, TSP, VAL-1, TPX2, GST and HSP, or antibodies thereto. These devices typically are adapted to provide a distinct visually detectable colored band at the location where the particular protein of interest is located when the concentration of the protein is above the threshold level. For additional detailed discussion of assay types which can be utilized according to the invention as well as various assay formats and automated analyzer apparatus see, e.g., U.S. Pat. No. 5,747,274. Filarial nematode protein detection can further be performed using multiplex technologies.

In other embodiments, the assays or immunoassays of the invention include beads coated with a binding agent against a filarial nematode protein or a fragment thereof, or antibody. Commonly used are polystyrene beads that can be labeled to establish a unique identity. Detection is performed by flow cytometry. Other types of bead-based immunoassays are known in the art, e.g., laser bead immunoassays and related magnetic bead assays (see, e.g., Fritzler, et al. (2009) *Expert Opinion on Medical Diagnostics* 3:81-89).

The methods of the invention can be automated using robotics and computer directed systems. The biological sample can be injected into a system, such as a microfluidic devise entirely run by a robotic station from sample input to output of the result. The step of displaying the result can also be automated and connected to the same system or in a remote system. Thus, the sample analysis can be performed in one location and the result analysis in another location, the only connection being, e.g., an internet connection, wherein the analysis is subsequently displayed in a format suitable for either reading by a health professional or by a patient.

In certain embodiments, the presence of any one or any combination of protective/neutralizing antibodies described herein identifies a subject as having been immunized with a vaccine against a filarial nematode. Thus, depending on antibody titer, the subject may or may not receive additional booster vaccinations.

In some embodiments, the presence of any one or any combination of the filarial nematode proteins described herein identifies a subject as having a filarial nematode infection. Thus, the subject is diagnosed as having filariasis and, in certain embodiments of this invention, treated with diethylcarbamazine, mebendazole, flubendazole, albendazole, ivermectin or a combination thereof. In one embodiment, the diagnosis can be made if the presence of any one of the filarial nematode proteins is detected in the subject's sample. In another embodiment, treatment is prescribed or administered if at least two of the filarial nematode proteins are identified positively in the biological sample.

Kits provided according to this invention include one or more binding agents, e.g., antibodies or antibody fragments, or filarial nematode proteins, and optionally a device with a solid surface. In some embodiments, the solid surface is a bead, slide, assay plate (e.g., a multiwell plate) or a lateral flow device, to which the binding agents/proteins are bound. In some embodiments, the kit further includes one or more standards or controls.

In some embodiments, the invention provides a microplate-based array for multiplex immunoassays. In accordance with some embodiments, each well can contain a single antibody against at least one of the listed filarial nematode proteins. In other embodiments, each well contains an array of antibodies against at least two or more of the listed filarial nematode proteins. In certain embodiments, each well of the plate includes an antibody to two, three, four, or five of the following proteins: ALT2, TSP, VAL-1, TPX2, GST and HSP. In particular embodiments, each well of the plate includes an antibody to each of ALT2, TSP, VAL-1, TPX2, GST and HSP.

In other embodiments, each well contains an array of at least two or more of the filarial nematode proteins of this invention. In certain embodiments, each well of the plate includes two, three, four, or five of the following proteins: ALT2, TSP, VAL-1, TPX2, GST and HSP. In particular embodiments, each well of the plate includes each of ALT2, TSP, VAL-1, TPX2, GST and HSP.

In other embodiments, the invention provides simple to use point-of-care diagnostic test strips akin to pregnancy detection strips, wherein the strip includes at least one antibody against at least one of the listed filarial nematode proteins. In alternative embodiments, the invention provides simple to use point-of-care diagnostic test strips, wherein the strip includes at least one of the instant filarial nematode proteins.

The test strip may include a positive and negative control to show the user that the reagents work properly and/or that the sample has been added to the strip properly. The strips may be provided with or without a casing and with or without additional reagents. Diagnostic test strips for lateral flow assays, such as the test strip assay described herein, may be constructed as described in the art, see, e.g., US 2010/0196200; US 2010/0129935; US 2009/0253119; and US 2009/0111171. Suitable materials for test strips include, but are not limited to, materials derived from cellulose, such as filter paper, chromatographic paper, nitrocellulose, and cellulose acetate, as well as materials made of glass fibers, nylon, dacron, PVC, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied sample, to ensure optimal test conditions.

The invention is described in greater detail by the following non-limiting examples.

Example 1: Small Heat Shock Protein Vaccine

Parasites.

*B. malayi* L3s were obtained from the NIAID/NIH Filariasis Research Reagent Resource Center (FR3) at the University of Georgia, Athens, GA Human Sera Samples.

About 10 ml of blood samples were collected from the following clinical groups of subjects (1) Endemic normal (EN) subjects, these were individuals who were asymptomatic and non-microfilaraemic; (2) asymptomatic microfilaraemic subjects (Mt) who had circulating microfilaria in their blood and were identified by microscopic examination of their night blood smears; (3) Chronic Pathology (CP) patients include those subjects who exhibited lymph edema and other chronic clinical symptoms of filariasis and (4) Non-endemic normal subjects (NEN) who lived in non-endemic areas and had no circulating parasites or antibodies and showed no evidence of any filarial disease. Sera were separated from these blood samples and were stored at −80° C. until use.

Expression and Purification of Recombinant *B. malayi* Heat Shock Protein.

To produce recombinant *B. malayi* small heat shock protein 12.6 (rBmHSP), the full-length gene sequence was cloned into pRSET-A (with an N-terminal hexahistidine tag) and was transformed into BL21(DE3) containing pLysS (Invitrogen, Carlsbad, CA) to minimize toxicity due to the protein. When absorbance of the cultures reached 0.6 OD value, 1 mM of IPTG (isopropyl thio-d-galactopyranoside) was added to the cultures and incubated for an additional 3 hours to induce gene expression. After lysing the cells, total proteins were separated in a 15% SDS-PAGE to confirm the expression of his-tagged protein. Subsequently, the histidine-tagged recombinant protein was purified using an immobilized cobalt metal affinity column chromatography (Clontech, Mountain View, CA) as per the manufacturer's recommendations. Recombinant protein was then separated in a 15% SDS-PAGE and stained with COOMASSIE brilliant blue R250. A single band was obtained after column purification.

Three-Dimensional Model of BmHSP.

A three-dimensional model of BmHSP protein was constructed by homology modeling. BLAST sequence homology searches were performed to identify template proteins in the PDB database. Human alpha-crystallin A, a recently crystallized protein, showed significant sequence identity and was therefore chosen as the template for modeling BmHSP. Model building was performed using MODELLER 9v6 (Sali & Blundell (1993) *J. Mol. Biol.* 234:779-815). The 3-D structure obtained was subsequently validated using PROCHECK program (Laskowski, et al. (1993) *J. Appl. Cryst.* 26:283-29). The best model predicted by PRO-CHECK had a score of −0.46 and was chosen for further modeling and for generating the 3-D structure using Rasmol program.

Analysis of the Structure of BmHSP.

The secondary structure and protein-protein interaction site of BmHSP was predicted at PDBsum and the Predict Protein E-mail server at the European Molecular Biology Laboratory, Heidelberg (Roos, et al. (1995) *Parasitol. Today* 11:148-150). Motif scanning was carried out via PROSITE pattern analysis to identify the functional motifs in BmHSP. B-cell, T-cell and CTL epitopes in BmHSP sequences were predicted using Immune Epitope Database and Analysis Resource (1EDB).

Phylogenetic Analysis of BmHSP.

Amino acid sequences of BmHSP were compared with members of other small heat shock family of proteins from different organisms. The following sequences were analyzed. Accession numbers are given in parenthesis. *Acontho-cheilonema vitae* (CAA48631); *Archaeoglobus fulgidus* (028308); *Artibeus jamaicensis* (P02482); *Aspergillus fumigatus* (Q4WV00); *Arabidopsis thaliana* (081822); *Artemia persimilis* (DQ310578); *Azotobacter vinelandii* (P96193); *Brugia pahangi* (CAA61152), *Brugia malayi* (AAU04396); *Buchnera aphidicola* (P57640); *Bombyx mori* (AF315318_1); *Bradyrhizobium japonicum* (P70918); *Caenorhabditis elegans* (Q7JP52); *Coccidioides immitis* (Q1E6R4); *Carica papaya* (Q69BI7); *Caenorhabditis remanei* (AAZ42349); *Dictyostelium discoideum* (Q54191); *Escherichia coli* (ibpA; P00054); *Escherichia coli* (ibpB; P00058); *Homo sapiens* (P02489); *Haemonchus contortus* (AAN05752); *Lygodactylus picturatus* (Q6EWI0); *Onchocercara volvulus* (CAA48633), *Ostertagia ostergi* (CAG25499); *Macaca mulatta* (P02488); *Mycobacterium tuberculosis* (P0A5B7); *Mus musculus* (AAA37861); *Nippostrongylus brasiliensis* (BA181970); *Plasmodium falciparum* (Q8IB02); *Rattus rattus* (CAA42910); *Saccharomyces cerevisiae* (P15992); *Solanum lycopersicum* (082545); *Streptococcus thermophilus* (P80485); *Trichinella spiralis* (ABJ55914); *Trypanosoma brucei* (Q57V53); *Toxoplasma gondii* (Q6DUA8). The alpha-crystallin domain from all sHSP sequences were aligned using ClustalW algorithm and the data set were used to build a phylogenetic tree with the PHYLIP software. The trees were made using the neighbor joining method, with Poisson-corrected amino acid distances.

Chaperone Assay.

One of the typical characteristics of chaperone is that they can bind to and protect cellular proteins from heat damage. When proteins are exposed to heat damage, they aggregate (thermal aggregation). Chaperones prevent this aggregation. To determine whether BmHSP could prevent thermal aggregation, a citruline synthase (CS) (Sigma, St. Louis, MO) thermal aggregation assay was used. CS was selected because this protein is highly sensitive to heat denaturation. An established method was used (Gnanasekar, et al. (2009) *Biochem. Biophys. Res. Commun.* 386:333-337). Briefly, 1 µM of CS was exposed to 45° C. in the presence or absence of BmHSP (2 µM) suspended in 50 mM of sodium phosphate pH 7.4 buffer containing 100 mM NaCl. BSA was used as a control. CS was incubated with BmHSP at a molar ratio of (1:2) for various time intervals from 0 to 40 minutes. Thermal denaturation (aggregation) was monitored spectrophotometrically at 360 nm.

In Vitro Peptide Binding Assay for Chaperone Activity.

Another characteristic of heat shock proteins is that they can bind to a variety of proteins. To determine whether BmHSP also possesses this function, CS and another protein, luciferase, were chemically denatured with 6M guanidine hydrochloride according to known methods (Gnanasekar, et al. (2009) supra). Native and chemically denatured proteins were then coated onto 96-well plates overnight at 4° C. After washing with PBS, wells were blocked with 3% BSA at room temperature. Following further washing, wells were incubated with his-tagged rBmHSP for 1 hour at 37° C. After washing again with PBS, optimally diluted anti-his-tagged HRP conjugate was added and incubated at 37° C. for 1 hour. After final washing, color was developed with ABTS [2,2'-azinobis(3-ethylbenzothiazoline-6-sulfonic acid)] and OD was measured at 405 nm.

Anti-BmHSP Antibody Levels in Human Sera.

A total of 20 sera samples belonging to different clinical groups such as Mf, CP, EN and NEN were analyzed for the presence and titer of anti-BmHSP IgG antibodies using an indirect ELISA (Cheirmaraj, et al. (1992) *J. Trop. Med. Hyg.* 95:47-51). Briefly, wells of a 96-well microtiter plate were coated with rBmHSP (1 µg/ml) in carbonate buffer, pH 9.6, overnight at 4° C. and blocked with 3% BSA for 1 hour at 37° C. Sera samples were added to the wells and the plates were incubated overnight at 4° C. After washing the wells, HRP-labeled mouse anti-human IgG was added (1:5000) and incubated further for 1 hour at 37° C. Color was developed using ABTS substrate. Absorbance was measured at 405 nm in a microplate reader (BIO-RAD, Hercules, CA). The isotype of anti-BmHSP IgG antibodies in the sera of subjects was also determined using an isotype-specific ELISA. Biotinylated mouse monoclonal antihuman IgG1, IgG2, IgG3 and IgG4 were used as the secondary antibodies and color was developed with avidin-HRP conjugate (Sigma, St. Louis, MO) as the secondary antibodies.

Cloning of Codon-Optimized BmHSP into pVAX Vector for DNA Vaccine.

Codon-optimized Bmhsp genes were cloned into eukaryotic expression vector pVAX (Invitrogen) using insert-specific primers (forward primer, 5'-CGC GGA TCC ATG GAA GAG AAG GTG GTG-3' (SEQ ID NO:1) containing BamHI site and reverse primer, 5'-CCG GAA TTC TCA CTT GTC GTT GGT G-3' (SEQ ID NO:2) containing EcoRI site). PCR parameters were as follows: 94° C. of denaturation for 30 seconds, 50° C. of primer annealing for 30 seconds, 72° C. of primer extension for 30 seconds for 30 cycles; and a final extension of 5 minutes was performed at 72° C. Insert DNA was sequenced to ensure authenticity of the cloned nucleotide sequence on both strands. Plasmids were maintained and propagated in *E. coli* TOP10F' cells. Subsequently, plasmids were purified using endotoxin-free plasmid extraction kit (Qiagen, Hilden, Germany). DNA was analyzed by agarose gel electrophoresis and quantified by spectrophotometry (OD 260/280, ratio>1.8).

Immunization of Mice.

Six-week-old male Balb/c mice purchased from Charles River Laboratories were used in these experiments. Humane use of animals in this study and the protocol was approved by the IACUC committee at the College of Medicine, University of Illinois Rockford. Each group was composed of five (5) mice and all mice were immunized intraperitoneally using three different immunization regimens. Group A mice were immunized using a prime-boost regimen. Mice were primed twice at two week intervals with 100 µg of endotoxin-free, codon-optimized pVAX Bmhsp DNA suspended in 50 µl volume. Following priming, all mice received two booster doses of 15 µg of rBmHSP protein (50 µl each) suspended in alum at two weeks interval. Group B mice were immunized with rBmHSP protein alone. These mice received four doses of 15 µg of rBmHSP protein suspended in alum given at two week intervals. Group C mice were immunized with DNA alone. These mice received four doses of 100 µg of pVAX Bmhsp DNA given at two week intervals. Group D animals received 100 µg of pVAX vector control and adjuvant at the same interval and remained as negative controls. Blood samples were collected from each mouse before immunization and one month after the last booster dose. After separating the sera, titer of circulating anti-BmHSP IgG antibodies and the respective isotypes were determined. Sera that showed high titer of antibodies against BmHSP were used in the Antibody Dependent Cellular Cytotoxicity (ADCC) assay described herein.

Anti-BmHSP Antibody Levels in the Sera of Mice.

Anti-BmHSP IgG antibody levels in the sera of immunized and control groups of mice were determined using an indirect ELISA (Veerapathran, et al. (2009) *PLoS Negl. Trop. Dis.* 3:e457). IgG1, IgG2a, IgG2b and IgG3 anti-BmHSP antibody levels were also determined using a mouse antibody isotyping ELISA kit (ThermoFisher Scientific, Rockford, IL). Color was developed with ABTS (2,2'-azinobis (3-ethyl benzothiazoline-6-sulfonic acid) chromogen substrate and the absorbance was measured at 405 nm in an ELISA reader (BIO-RAD).

Depletion Anti-BmHSP Antibodies from Human and Mice Sera.

Anti-BmHSP antibodies were depleted from pooled sera of EN subjects and immunized mice by incubating the pooled sera with cobalt IMAC resin coupled with his-tagged rBmHSP according to established methods (Veerapathran, et al. (2009) supra). Briefly, 1 mg of his-tagged rBmHSP was coupled to 2 ml bed volume of IMAC resin for 2 hours at 37° C. After washing the resin once with 10 ml of PBS (pH.8), 200 µl of pooled sera was added and incubated overnight at 4° C. After incubation, the resin mixture was centrifuged for 2 minutes at 750 rpm and the supernatant was collected. Depletion of anti-BmHSP antibodies in the supernatant was confirmed by ELISA as described herein.

Anti-BmHSP IgG1, anti-BmHSP IgG2a, anti-BmHSP IgG2b, anti-BmHSP IgG3 and anti-BmHSP IgG4 antibodies from pooled sera of EN subjects and pooled sera of immunized mice were depleted using NHS (N-hydroxysuccinimidyl) resin (Thermo fisher scientific). Briefly, 1 µg of respective monoclonal antibodies were coupled to NHS resin column. After washing the resin twice with PBS (pH.8), 100 µl of sera were passed through the column. The flow through was collected as the antibody depleted sera. Depletion of the specific isotype of antibody was confirmed by an isotype-specific ELISA as described herein. After washing the column three times with PBS (pH 7.4), bound antibodies were eluted using Glycine-HCl buffer (pH 2.7) from the resin and the pH was adjusted to 7.4 with 1 M Tris buffer (pH 8). The recovered elute contained the specific antibody as confirmed again by an ELISA. The antibody depleted sera was also reconstituted with the eluted antibodies. An aliquot of depleted sera was reconstituted with the eluted antibodies to its original concentration using values determined by an earlier ELISA on the neat serum samples. Antibody depleted sera, eluted antibodies and reconstituted sera samples were then used in an ADCC assay.

Antibody-Dependent Cellular Cytotoxicity (ADCC) Assay.

In vitro ADCC assay was performed according to known methods (Chandrasekhar, et al. (1985) *Parasite Immunol.* 7:633-641). Briefly, ten (10) L3 of *B. malayi* were incubated with $2 \times 10^5$ peritoneal cells (PEC) collected from normal mice, 50 µl of pooled mouse sera samples and 50 µl of RPMI 1640 media in a 96-well culture plate (Thermo Fisher Scientific). After 48 hours of incubation at 37° C. and 5% $CO_2$, larval viability was determined at 400× using a light microscope. Larvae that were limpid and damaged were counted as dead. In addition, dead larvae also had clumps of cells adhered to it and were more transparent than live. Larvae that were active, coiled and translucent were counted as live. ADCC was estimated as the percent larval death calculated using the formula:

Number of Dead larvae÷Total Number of Larvae× 100.

ADCC assay was also performed with pooled human sera samples as described herein except that the human sera samples were incubated with $2 \times 10^5$ PBMCs collected from normal health subjects and 6-12 *B. malayi* L3 for 48 hours at 37° C. and 5% $CO_2$. Larval viability and death was determined as described above.

Protection Studies in Mice.

Vaccine potential of BmHSP was evaluated in a mouse model of challenge infection. Mice were immunized as described above using prime-boost, DNA alone or protein alone approach. Vector and alum group served as negative controls. Immunized and control animals were challenged using a micropore chamber method as known in the art (Abraham, et al. (1986) *Immunology* 57:165-169). Briefly, micropore chambers were assembled using 14×2 mm PLEXIGLASS (acrylic) rings (Millipore Corporations, Bedford, MA) and 5.0 µm NUCLEOPORE polycarbonate membranes (Millipore Corporations). The membranes were attached to the PLEXIGLASS rings with cyanoacrylic adhesive and dental cement. The chambers were immersed overnight at 37° C. in sterile RPMI medium containing gentamycin and antimycotic solution. Before challenge experiments, 20 live, infective L3s suspended in RPMI 1640 medium supplemented with 15% heat-inactivated fetal calf serum (FCS) were introduced into the micropore chambers and the opening was sealed with dental cement. Micropore chamber containing the L3s were then surgically implanted into the peritoneal cavity of each mice under anesthesia. Aseptic conditions were followed for the surgical procedures. After 48 hours of implantation, animals were sacrificed and the chambers were recovered from peritoneal cavity. Contents of each chamber were emptied and larvae were examined microscopically for adherence of cells and for larval death. Dead and live larvae were identified as described above under ADCC. The percentage of protection was expressed as the number of dead parasites number of total parasites recovered×100.

Splenocyte Proliferation Assay.

Spleens were collected from all mice from the above experiment and single-cell suspension of spleen cells was prepared. Approximately $2 \times 10^5$ cells/well suspended in complete RPMI 1640 medium supplemented with 10% heat-inactivated FCS were incubated at 37° C. and 5% $CO_2$ for 72 hours with rBmHSP (1 µg/ml), ConA (1 µg/ml) or with medium alone. After incubation, cell proliferation was determined using cell counting kit (CCK-8) purchased from Dojindo Molecular Technologies, Inc. (Gaithersburg, MD). Stimulation index of spleen cell proliferation was calculated using the formula: Absorbance of stimulated cells÷Absorbance of unstimulated cells.

Cytokine Analysis.

Spleen cells from immunized and control mice were cultured at 37° C. and 5% $CO_2$ for 72 hours with rBmHSP (1 µg/ml), ConA (1 µg/ml) or with medium alone as described above. After 72 hours, culture supernatants and cell pellets were collected separately for cytokines analysis. For measuring cytokine mRNA, cell pellets were suspended in TRIZOL (phenol, guanidinium and thiocyanate) reagent (GIBCO-BRL, Life technologies, Carlsbad, CA) and total RNA was extracted as per the manufacturer's instructions. After ethanol washes, RNA pellets were dissolved in RNAse-free water (Sigma) and treated with DNase I before determining total RNA concentration using a Beckman spectrophotometer at 260 nm. Reverse transcription of total RNA was performed using first strand cDNA synthesis kit (SABiosciences, Frederick, MD) as per manufacturer's recommendations. Relative quantification of the expression of genes of interest was measured in an Applied BioSystem 7300 real-time PCR machine (Applied BioSystems, Foster City, CA). PCR amplifications were performed with the LIGHTCYCLER-DNA SYBR Green (cyanine dye) mix (SAbiosciences). The reaction was performed using the following PCR conditions: 15 minutes activation step at 95° C. for one cycle, 15 seconds denaturation step at 95° C., annealing of primers for 20 seconds at 50° C. and elongation step for 15 seconds at 72° C. DNA was amplified for 50 cycles. The fluorescent DNA binding dye SYBR Green (cyanine dye) was monitored. RT-PCR data array set was generated and analyzed using SABiosciences web-based data analysis system.

Culture supernatants were then collected from splenocyte cultures 72 hours after incubation with rBmHSP (1 µg/ml), ConA (1 µg/ml) or with medium alone. Secreted levels of IL-2, IL-4, IFN-γ and IL-10 protein in the culture supernatants were determined using a sandwich ELISA kit purchased from ThermoFisher Scientific. Concentration of each cytokine was determined from a standard curve plotted using recombinant mouse IL-2, IL-4, IFN-γ or IL-10.

Statistical Analysis.

Statistical analysis was performed using XL STAT software v.7.5.2 (Kovach Computing Services, Anglesey, UK). Statistical significance between comparable groups was estimated using appropriate non-parametric tests, with the level of significance set at $p<0.05$.

Expression of Recombinant BmHSP12.6 (BmHSP).

BmHSP was cloned in pRSET A vector and was expressed as a histidine-tagged (his-tagged) fusion protein in E. coli BL21 (DE3)PLysS. Recombinant BmHSP protein was subsequently purified using IMAC column. The molecular mass of the purified recombinant his-tag fusion protein was found to be approximately 18 kDa. The column-purified recombinant protein appeared as a single band in SDS-PAGE.

Predicted Three-Dimensional Structure of BmHSP.

Amino acid sequences of the human alpha crystalline A chain share 42% similarity with BmHSP. Since crystal structure of the human alpha crystalline A chain is already available, this was used that as a template to model the putative structure of BmHSP using the Modeller 9v6 program. PROCHECK analysis was used to select the best model that showed a score of −0.41 compared to the template (Laskowski, et al. (1993) *J. Appl. Cryst.* 26:283-29). A Ramachandran plot analysis was also performed on the BmHSP sequence. These analyses showed that 92% of residues were in the most favorable region with no steric hindrance. About 6.7% residues were found in the additional allowed region. Models that showed over 90% residues in the most favored regions were predicted as the most ideal three dimensional model as predicted by the Ramachandran plot (Balazs, et al. (2001) *Protein Eng. Des. Sci.* 14:875-880). Secondary structure prediction analysis was also performed on BmHSP protein using PDBsum server at EMBL. This analysis showed that each alpha-crystalline domain of BmHSP monomer had an immunoglobulin core composed of seven β-strands arranged in two anti-parallel sheets. The secondary structure prediction of BmHSP showed two sheets, four beta hairpins, one beta bulge, seven strands, two helices, seven beta turns and one gamma turn in the structure of BmHSP.

Previous studies showed that BmHSP binds to human IL-10 receptor I α chain (Gnanasekar, et al. (2008) *Mol. Biochem. Parasit.* 159:98-103). To identify the IL-10 receptor binding site on BmHSP, a predictive protein-protein interaction analysis was performed (Ofran & Rost (2007) *Bioinformatics* 23:e13-e16). Results from the prediction analysis showed that the N-terminal fragment of BmHSP (amino acids from Met1 to Asn26) had a strong protein-protein interaction region. Further sequence analysis of this region showed that the amino acid sequences from Val5 to Glu42 had significant sequence identity to human IL-10R binding region of human IL-10. These findings confirm that the N-terminal region of BmHSP may be involved in the binding of BmHSP to human IL-10 receptor I α chain.

Motif and Phylogenetic Analysis on BmHSP.

Motif analysis performed at PROSITE showed several putative post-translation modification sites such as N-glycosylation sites (residues 11 to 14 and 98 to 101), protein kinase-c phosphorylation sites (residues 83 to 85 and 100 to 102), casein kinase II phosphorylation sites (residues 68 to 71 and 88 to 91) and N-myristylation sites (residues 40 to 45) on BmHSP. Similar motifs were also observed in human IL-10 further indicating that BmHSP may mimic human IL-10 function (Gnansekar, et al. (2008) supra). Epitope mapping on BmHSP revealed the presence of B-cell, T-cell and CTL epitope regions, indicating that BmHSP is potentially a highly immunogenic protein (Table 2).

TABLE 2

| Epitope Predicted | Position of Epitope in the Amino Acid Sequence | Peptide Sequence | SEQ ID NO: |
|---|---|---|---|
| B-Cell Epitopes | 12-23 | WSAEQWDWPLQH | 3 |
|  | 26-35 | EVIKTNTNDK | 4 |
|  | 67-74 | SRAEHYGE | 5 |
|  | 84-94 | KLPSDVDTKTL | 6 |
| T-Cell Epitopes | 45-53 | FTPKEIEVK | 7 |
|  | 50-57 | IEVKVAGD | 8 |
|  | 38-45 | VGLDASFF | 9 |
|  | 39-47 | GLDASFFTP | 10 |
|  | 52-60 | VKVAGDNLV | 11 |
|  | 84-92 | KLPSDVDTK | 12 |
|  | 92-100 | KTLTSNLTK | 13 |
|  | 27-35 | VIKTNTNDK | 14 |
|  | 90-98 | DTKTLTSNL | 15 |
|  | 44-52 | FFTPKEIEV | 16 |
|  | 38-46 | VGLDASFFT | 17 |
|  | 100-108 | KRGHLVIAA | 18 |
|  | 73-81 | GEIKREISR | 19 |
|  | 43-51 | SFFTPKEIE | 20 |
| CTL Epitopes | 78-86 | REISRTYKL | 21 |
|  | 74-82 | GEIKREISR | 22 |
|  | 70-78 | AEHYGEIKR | 23 |

A phylogenetic analysis performed using representative sHSP sequences from different groups of organisms showed that BmHSP, *C. elegans* HSP and *C. remani* HSP form a monophyletic group, separated from the other groups of organisms.

BmHSP is a Chaperone. Most of the heat shock proteins reported to date have chaperone function. To determine whether BmHSP also has similar chaperone function, a thermal aggregation reaction was performed using a model substrate, Citrulline synthase (CS). Incubation of CS at 42° C. resulted in unfolding of the protein and subsequent aggregation within 10 minutes. Addition of BmHSP to CS protein (at a molar ratio of 1:2), before the heat treatment, significantly (P<0.01) inhibited the thermal aggregation of CS protein. A non-chaperone control protein, BSA, had no effect on the heat-induced aggregation of CS protein.

Another function of chaperone proteins is that they can specifically bind to denatured proteins. To determine whether BmHSP can specifically bind to denatured proteins, rBmHSP was incubated with native and denatured CS or native and denatured luciferase substrates. These studies showed that rBmHSP preferentially bound to denatured protein substrates compared to native or control protein. These findings thus confirmed that BmHSP can act as a molecular chaperone potentially protecting the parasite cellular proteins from the damaging effects of the host.

Antibody Responses in Human.

The results presented herein indicate that BmHSP has several T-cell and B-cell epitopes. Therefore, it was evaluated whether filariasis-infected individuals carry antibodies to BmHSP. Accordingly, the titer of anti-BmHSP IgG antibodies in the sera of EN, CP, Mf and NEN subjects was measured. The results showed that the EN subjects had the highest levels of anti-BmHSP antibodies (p<0.001). Subsequent isotype analysis of the IgG antibodies showed that compared to the infected groups (Mf and CP) of individuals, sera from EN subjects had high titers of IgG1 and IgG3 anti-BmHSP antibodies. Mf carriers had only significant levels of anti-BmHSP IgG2 antibodies in their sera. Similarly, CP individuals had only significant levels of anti- BmHSP IgG4 antibodies in their sera. Anti-BmHSP IgG1 and IgG3 levels were very low in the sera of these Mf and CP individuals. Anti-BmHSP antibodies were not detectable in the sera of NEN subjects.

Results of ADCC Assay.

Since antibodies to BmHSP were present in all infected groups of individuals (Mf and CP) and EN subjects, it was determined whether these antibodies were functional. Using an antibody-dependent cell cytotoxicity assay, it was tested if anti-BmHSP12.6 IgG antibodies had any protective function against *B. malayi*. These studies showed that pooled EN sera promoted adherence of PBMC's to L3 and induced significant (77.37%) death of *B. malayi* L3s in vitro (Table 3), whereas, pooled sera from Mf and CP failed to participate in the ADCC function. These findings indicated that EN sera have anti-parasitic activities. To determine if this function is associated with antibodies, antibody depletion studies were performed. Depletion of anti-BmHSP antibodies from EN sera resulted in significant reduction (21.42%) in larval death (Table 3) confirming that anti-BmHSP antibodies in the sera of EN subjects, but not Mf or CP subjects, participate in larval killing.

TABLE 3

| Groups | Dead L3 | Live L3 | Total L3 | % Larval Death (Mean ± SD*) |
|---|---|---|---|---|
| Endemic Normal (EN) sera | 5 | 1 | 6 | 77.37 ± 8.41 |
|  | 5 | 2 | 7 |  |
| EN sera depleted of anti-rBmHSP antibodies | 2 | 5 | 7 | 21.42 ± 10.12 |
|  | 1 | 6 | 7 |  |
| Non-Endemic Normal (NEN) sera | 1 | 5 | 6 | '19.44 ± 3.92 |
|  | 2 | 7 | 9 |  |

*Values represent mean ± SD of three wells.

Further depletion studies showed that the anti-parasitic effect of anti-BmHSP antibodies was associated with IgG1 isotype of antibodies. Depletion of IgG1 antibodies from EN sera significantly (40%) inhibited the ADCC function (Table 4). Reconstitution of anti-BmHSP antibody depleted EN sera with eluted anti-BmHSP IgG1 antibodies regained the ADCC function (Table 3). These findings thus indicated that anti-BmHSP IgG1 antibodies are critical for ADCC function.

TABLE 4

| EN Sera |  | % Larval Death |
|---|---|---|
| Neat Sera |  | 72 |
| Depleted of: | IgG1 | 40 |
|  | IgG2 | 71.43 |
|  | IgG3 | 60 |
|  | IgG4 | 62.5 |
| Reconstituted with: | IgG1 | 70 |
|  | IgG2 | 69.23 |
|  | IgG3 | 66.67 |
|  | IgG4 | 54.55 |

Values represent mean of three wells.

Antibody Responses in Mice.

Mice immunized with rBmHSP developed significant levels of anti-BmHSP IgG antibodies. More specifically, prime-boost vaccine regimen induced significantly higher titer of IgG antibodies compared to DNA vaccine alone group (p<0.05). However, rBmHSP protein vaccine induced the highest IgG antibody titer. Analysis of the isotype of anti-BmHSP IgG antibodies showed that predominantly IgG1, IgG2a and IgG2b anti-BmHSP antibodies were present in the sera of vaccinated animals. The ADCC assay was also performed with mouse sera. These studies showed that sera from BmHSP-vaccinated mice promoted adherence of peritoneal exudate cells to L3 and participated in ADCC function (83.02% larval killing) compared to control sera (13%) (p<0.002) (Table 5).

TABLE 5

| Immunization Regimen | % Larval Death |
|---|---|
| Bmhsp DNA prime and rBmHSP protein boost | 83.02 ± 3.62 |
| Bmhsp DNA | 43.7 ± 8.12 |
| rBmHSP protein | 55.08 ± 1.15 |
| pVAX & alum control | 13 ± 2.35 |

Values represent mean ± SD of three wells.

Similar to human sera, individual isotype of IgG antibodies were depleted from the sera of vaccinated mice to determine the isotype of anti-BmHSP antibodies that participate in the ADCC function. Results from these studies showed that, similar to that observed with EN sera, anti-BmHSP IgG1 antibodies were involved in ADCC-mediated killing of L3 in mice as well (Table 6).

TABLE 6

| Immunized Mice Sera |  | % Larval Death |
|---|---|---|
| Neat Sera of BmHSP prime-boost |  | 80.16 |
| Depleted of: | IgG1 | 37 |
|  | IgG2a | 72 |
|  | IgG2b | 71 |
|  | IgG3 | 80 |
| Reconstituted with: | IgG1 | 80 |
|  | IgG2a | 63 |
|  | IgG2b | 87 |
|  | IgG3 | 71 |

Values represent mean of three wells.

Vaccine Potential of BmHSP in Mice.

Vaccine potential of BmHSP was assessed in Balb/c mice using a micropore chamber method. Results showed that mice immunized using the prime-boost vaccination regimen and protein vaccine of BmHSP exhibited nearly 72% and 58% mortality, respectively, of L3s implanted into the peritoneal cavity of the immunized mice (Table 7). While chambers implanted in the control groups of animals showed only 7% mortality of the parasite, the difference between the protection of control group of mice and vaccinated mice was significant (P<0.001). On the other hand, mice immunized by DNA vaccine alone induced only 31% protection. Thus, the prime-boost vaccination regimen appeared to be highly efficient in conferring vaccine-induced protection against a challenge infection compared to DNA alone or protein alone immunization protocols.

TABLE 7

| Immunization Regimen | % Larval Death |
|---|---|
| Bmhsp DNA prime and rBmHSP protein boost | 72 ± 10.22 |
| Bmhsp DNA | 31 ± 5.23 |
| rBmHSP12.6 protein | 58 ± 7.76 |
| pVAX & alum control | 7 ± 5.2 |

Values represent mean ± SD. N = 5. Data is from one of two similar experiments showing comparable results.

Immune Responses in BmHSP Vaccinated Mice.

To determine cellular immune responses to BmHSP in the vaccinated mice, spleen cells collected from vaccinated and control mice were cultured in the presence of rBmHSP protein and their proliferative responses and cytokine profiles were evaluated. Proliferative response of spleen cells from animals immunized with the prime-boost vaccine regimen was significantly (P>0.05) higher (stimulation index of 3.35±0.176) compared to rBmHSP protein alone vaccination group (stimulation index of 2.22±0.018) or Bmhsp DNA vaccination alone group (stimulation index of 3.53±0.102). Spleen cells from the control group of animals failed to proliferate in response to rBmHSP (stimulation index of 0.98±0.013) and was similar to media alone controls. Since the spleen cells from vaccinated animals were proliferating significantly to recall response to rBmHSP, levels of cytokines in the culture supernatants were measured. These results showed that IFN-γ was the predominant cytokine secreted by spleen cells from vaccinated animals at 72 hours after stimulation with rBmHSP. A real time-PCR cytokine gene array was performed on mRNA collected from the spleen cells stimulated with rBmHSP. These results showed that both Th1 (IFN-γ, CD-28, IL-12, IL-2) and Th2 (IL-4, IL-5, IL-1R) cytokine genes were significantly increased in vaccinated animals.

Example 2: rBmALT2+rBmHSP Multivalent Vaccine

Parasite.

*Brugia malayi* L3s were obtained from the NIAID/NIH Filariasis Research Reagent Resource Center (FR3) at the University of Georgia, Athens, GA.

Construction of Monovalent and Multivalent DNA Vaccines.

Monovalent DNA vaccine was composed of Bmhsp or Bmalt2 in pVAX1 vector. To prepare the monovalent vaccine, codon optimized Bmhsp or BmALT2 genes were cloned into the eukaryotic expression vector pVAX1 (Invitrogen, Carlsbad, CA) using insert-specific primers (Gnanasekar, et al. (2004) supra). The multivalent vaccine was composed of Bmhsp and Bmalt2 genes in the same pVAX1 vector. Codon optimized Bmhsp gene was first cloned into pVAX1 vector with no stop codon in the reverse primer (5'-CCG GAA TTC TCA CTT GTC GTT GGT G-3'; SEQ ID NO:24) but contained a PstI site. Codon optimized Bmalt2 gene was then inserted into this clone using gene specific primers (Gnanasekar, et al. (2004) supra). PCR parameters for all the three constructs were: 94° C. denaturation for 30 seconds, 50° C. primer annealing for 30 seconds, 72° C. primer extension for 30 seconds for 30 cycles; a final extension of 5 minutes was performed at 72° C. Insert DNA was finally sequenced to ensure authenticity of the cloned nucleotide sequence on both strands. Plasmids were maintained and propagated in *E. coli* TOP10F' cells. Plasmids were purified using endotoxin-free plasmid extraction kit (Qiagen, Valencia, CA). DNA was analyzed by agarose gel electrophoresis and quantified in a spectrophotometer (OD 260/280, ratio>1.8).

Expression and Purification of Recombinant Proteins.

All the genes were cloned in pRSET-A vector (with an N-terminal hexahistidine tag) to produce recombinant proteins. Bmhsp and Bmalt2 constructs were transformed into BL21(DE3) containing pLysS *E. coli* host (Invitrogen) to minimize toxicity due to the protein. When absorbance of the cultures reached 0.6 OD value, 1 mM of IPTG (isopropyl thio-d-galacto pyranoside) was added to the cultures and incubated for an additional 3 hours to induce the gene expression. After lysing the cells, total proteins were separated in 15% and 12% SDS-PAGE to confirm the expression of his-tag recombinant BmHSP (rBmHSP) and rBmALT2 proteins. The recombinant proteins were then purified using an immobilized cobalt metal affinity column chromatography (Clontech, Mountain View, CA) as per the manufacturer's recommendations. Recombinant proteins were then separated in SDS-PAGE and stained with COOMASSIE brilliant blue R250 and silver stain. These studies showed that a single band was obtained after column purification. Endotoxins if any in the recombinant preparations were removed by passing the recombinant proteins through polymyxin B affinity columns (Thermo Fisher Scientific, Rockford, IL) and the levels of endotoxin in the final preparations were determined using an E-TOXATE kit (Sigma, St Louis, MO) as per manufacturer's instructions. Endotoxin levels were below detection limits in these recombinant protein preparations.

Immunization of Mice.

Six-weeks old male Balb/c mice purchased from Charles River Laboratories were used in these experiments. Humane use of animals in this study and the protocol was approved by the IACUC committee at the College of Medicine, University of Illinois Rockford. Mice were divided into four (4) groups of five (5) animals each. All mice were immunized subcutaneously using a DNA prime—protein boost vaccine regimen. All experimental groups of mice were primed with two injections of endotoxin-free codon optimized DNA given in 50 μl volume and boosted with two doses of recombinant proteins suspended in alum (50 μl each) given at two weeks interval.

Group A mice were primed with 100 μg of pVAXBmhsp and boosted with 15 μg of rBmHSP; Group B mice were primed with 100 μg of pVAX Bmalt2 and boosted with 15 μg of rBmALT2; Group C mice were primed with 100 μg of pVAXBmhsp/Bmalt2 DNA and boosted with 15 μg of rBmHSP and 15 μg of rBmALT2. Group D mice received 100 μg of pVAX1 vector plus 50 μl of alum and served as controls. Blood samples were collected from each mouse before immunization and one month after the last booster dose. Sera were separated and stored at −80° C.

Evaluation of Antibody Responses in Mice.

Levels of anti-BmHSP and anti-BmALT2 antibodies were measured in the sera of immunized and control groups of mice using an indirect ELISA according to established methods (Veerapathran, et al. (2009) supra; Gnanasekar, et al. (2004) supra). Briefly, wells of 96-well microtiter plates were coated with rBmHSP, rBmALT2 or rBmHSP (1 μg/ml) in carbonate buffer (pH 9.6) overnight at 4° C. After washing the wells, unbound sites were blocked with 3% BSA for 1 hour at 37° C. Diluted sera samples were then added to the wells and incubated further overnight at 4° C. After washing the wells, HRP-labelled rabbit anti-mouse IgG was added (1:5000) and incubated further for 1 hour at 37° C. Color was developed using ABTS (2, 2"-azinobis (3-ethylbenzothiazoline-6-sulfonic acid)) substrate. Absorbance was measured at 405 nm in a microplate reader (BIO-RAD, Hercules, CA).

Protection Studies in Mice.

Vaccine potential of the monovalent and multivalent vaccine formulations were then evaluated in a mice model. Mice were immunized as described above using the prime boost approach. Vector plus alum group served as negative controls. Immunized and control animals were challenged using a micropore chamber method known in the art (Abraham, et al. (1989) *Am. J. Trop. Med. Hyg.* 40(6):598-604). Briefly, micropore chambers were assembled using 14×2 mm PLEXIGLASS (acrylic) rings (Millipore Corporations, Bedford, MA) and 5.0 μm NUCLEOPORE polycarbonate membranes (Millipore Corporations) that were attached to the PLEXIGLASS (acrylic) rings with cyanoacrylic adhesive and dental cement. The chambers were immersed overnight at 37° C. in sterile RPMI medium containing gentamycin and antimycotic solution. Before challenge experiments, 20 live infective L3s suspended in RPMI1640 medium supplemented with 15% heat inactivated fetal calf serum (FCS), were introduced into the micropore chambers and the opening was sealed with dental cement. Micropore chamber containing the L3s were then surgically implanted into the peritoneal cavity of each mice under anaesthesia. Aseptic conditions were followed for the surgical procedures. After 48 hours of implantation, animals were sacrificed and the chambers were recovered from peritoneal cavity. Contents of each chamber were emptied and larvae were examined microscopically for adherence of cells and for larval death. Larval viability was determined microscopically at 100×. The percentage of protection was expressed as the number of dead parasites number of total parasites recovered×100.

Cytokine Analysis in Mice.

The percent of rBmHSP and rBmALT2 specific interferon-γ (IFN-γ) and interleukin-4 (IL-4) secreting cells were determined in the spleen of control and vaccinated mice using an ELISPOT assay. Briefly, MILLIPORE MULTI-SCREEN HTS Filter plates were coated with monoclonal rat anti mouse IFN-γ or monoclonal rat anti-mouse IL-4 antibodies (BD Pharmigen, San Diego, CA) at a concentration of 10 µg/ml in PBS buffer. After washing the plates, non-specific sites were blocked by incubating the wells in complete RPMI with 10% fetal calf serum for one hour at room temperature. Approximately $3 \times 10^6$ spleen cells suspended in complete RPMI1640 medium supplemented with 10% heat inactivated FBS were then added to each wells. Cells were stimulated with rBmHSP or rBmALT2 (1 µg/ml). Unstimulated cells served as controls. Forty-eight hours after incubation at 37° C. in humidified 5% $CO_2$, plates were washed and further incubated for 1 hour at room temperature with 2 µg of biotinylated rat anti-mouse IFN-γ or biotinylated rat anti-mouse IL-4 antibody (BD Pharmigen). After washing the plates, streptavidin-conjugated horseradish peroxidase (Thermo Fisher Scientific) was added (1:800) to each well and incubated at room temperature for one hour. Plates were washed and color developed using DAB substrate (Thermo Fisher Scientific). Total numbers of spots were counted under a dissection microscope.

Statistical Analysis.

Statistical analysis was performed using XL STAT software v.7.5.2 (Kovach Computing Services, Anglesey, UK). Statistical significance between comparable groups was estimated using appropriate non-parametric tests, with the level of significance set at $p<0.05$.

Antibody Responses in Mice.

It was first determined whether the multivalent vaccine could elicit significant antibodies against each of the antigenic components. Previous studies have shown that mice similarly vaccinated with *B. malayi* antigens elicited significant host protective IgG antibodies (Veerapathran, et al. (2009) supra). Therefore, IgG antibody titers were analyzed. The results of this analysis indicated that the monovalent immunization with Bmhsp+rBmHSP and Bmalt2+rBmALT2 elicited significant ($p<0.005$) titers of anti-BmHSp and anti-BmALT2 IgG antibodies (FIG. 1). The multivalent vaccine also elicited significant IgG antibody titers. Following multivalent vaccine, the mice produced IgG antibodies against both BmHSP and BmALT2 equally, suggesting that the antigens do not interfere or compete for dominance. An interesting finding was that the multivalent vaccine elicited 1.5- to 1.75-fold higher ($p<0.005$) titers of IgG antibodies compared to the monovalent vaccine (FIG. 1). These finding indicated that the two antigens in the multivalent formulation can act synergistically by increasing the vaccine-induced antibody responses against each antigens in the vaccinated mice. The findings also indicated that combining these two antigens in the vaccine formulation has a great advantage. Given the robust IgG antibody responses induced following vaccination, it is also possible that the concentration of the component antigens in the multivalent preparation can be reduced.

Multivalent Vaccine Induces Significant Protection in Mice.

The results herein showed that significant IgG antibodies were elicited following vaccination with monovalent and multivalent vaccine preparations. To test if the immune responses elicited following vaccination were protective, vaccinated animals were challenged with live third stage infective larvae (L3) of *B. malayi*. Since the parasites do not reach maturity in these animals, a better recovery of worms is obtained if the parasites are surgically implanted into the animals. A standard micropore chamber challenge method (Abraham, et al. (1989) supra). These studies showed that close to 61% protection could be achieved in mice immunized with a monovalent vaccine (Table 8). This was highly significant ($p<0.001$) compared to negative controls. This finding also showed that rBmHSP and rBmALT2 are of use in vaccines for lymphatic filariasis. Challenge experiments in mice immunized with multivalent vaccine showed that significantly ($p<0.005$) higher protection could be achieved compared to monovalent vaccination (Table 8). These findings also clearly correlated with the higher IgG antibody titer in these animals and support the above finding that rBmALT2 and rBmHSP can synergistically enhance the protective immune responses in vaccinated animals when given as a prime boost regimen (Table 8).

TABLE 8

| Vaccination regimen | Percent Larval Death[a] | Groups |
|---|---|---|
| Bmhsp DNA prime and rBmHSP protein boost | 61 ± 4.24 | Monovalent |
| Bmalt2 DNA prime and rBmALT2 protein boost | 76 ± 8.21 | Monovalent |
| Bmhsp + Bmalt2 prime and rBmHSP and rBmALT2 protein boost | 90 ± 7.53 | Multivalent |
| pVAX plus alum control | 22 ± 10.41 | Control |

[a]Values are mean + SD. N = 5. Data is from one of two similar experiments showing comparable results.

Figure 3:
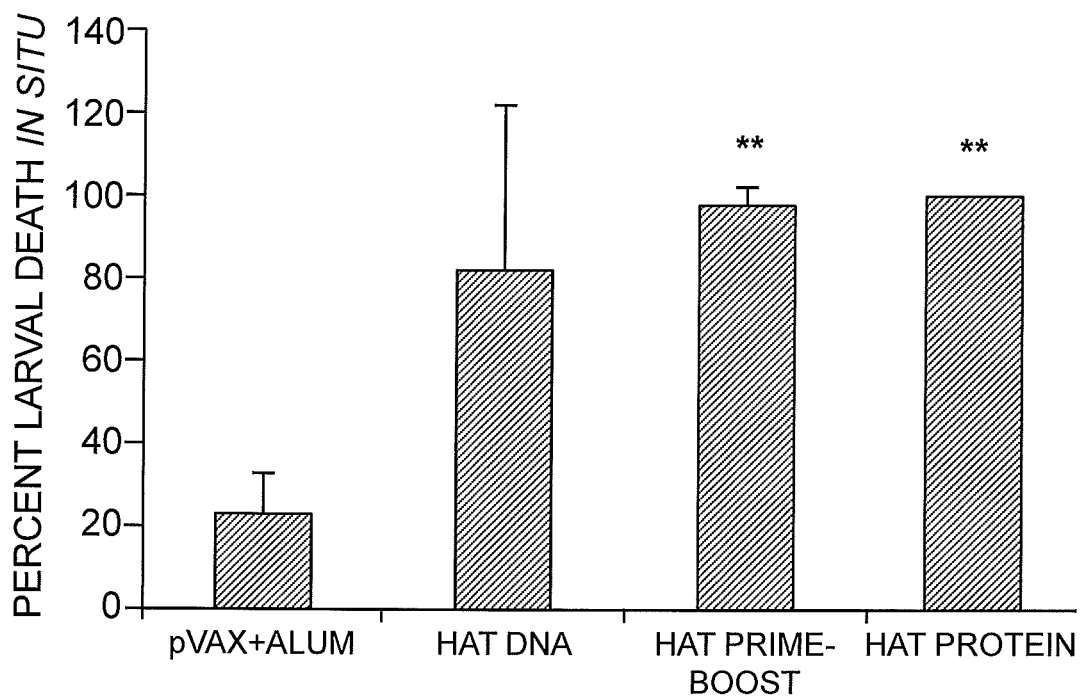
FIG. 3 shows the degree of protection conferred by a multivalent vaccine in a mouse model. Balb/c strain of mice were immunized with HAT (HSP/ALT2/TSP) hybrid DNA, with recombinant HAT protein or a combination of both using a prime boost approach. HAT hybrid DNA was used for priming. Two weeks following the priming, mice were boosted with HAT hybrid protein. Another group of mice were immunized with HAT hybrid DNA or with HAT hybrid protein. Control groups of mice received only blank vector or alum adjuvant. Two weeks after the last immunization, mice were challenged with 20 infective larvae of *Brugia malayi* by placing them in a micropore chamber in the peritoneal cavity of the immunized mice. After 48 hours, larval death was measured to determine the success of vaccination.

To further demonstrate efficacy, mice were immunized with various prime-boost combinations. As shown in FIG. 3, 100% protection can be achieved in mice following immunization with HAT hybrid protein or after prime boost immunization with HAT hybrid DNA and HAT hybrid protein.

Cytokine Responses.

Figure 2A:
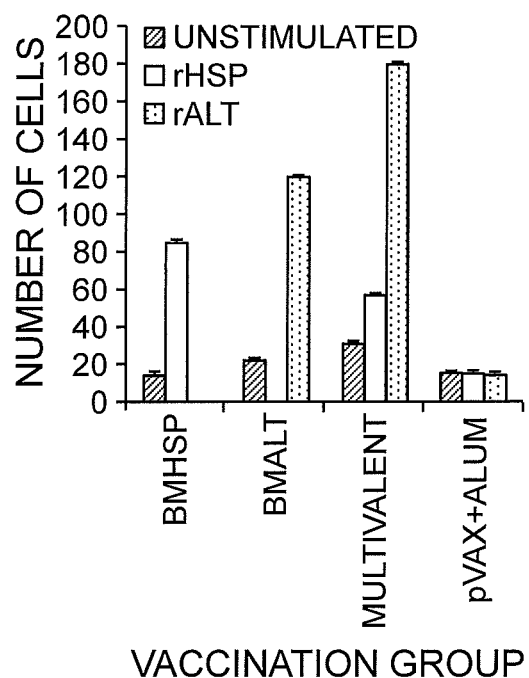
FIGS. 2A-2B show the number of IL-4 (FIG. 2A) and IFN-$\gamma$ (FIG. 2B) secreting cells in the spleen of mice vaccinated with monovalent (BmHSP or BmALT2) or multivalent vaccine. An ELISPOT assay was performed after stimulating the cells with rBmHSP or rBmALT (1 µg/ml). Single cell preparations of spleen cells were stimulated with respective antigens for 48 hours and spot forming cells were counted. Results show that both monovalent and multivalent vaccine promoted IL-4 secreting cells. Multivalent vaccination induced the higher number of IL-4 producing cells than controls. IFN-$\gamma$ producing cells were comparatively low. These findings further confirm that BmHSP and BmALT2 synergistically boost the immune responses in vaccinated animals following a multivalent vaccination. N=5. Results are expressed as mean number of spot forming units per $3\times10^6$ cells±SD.
Figure 2B:
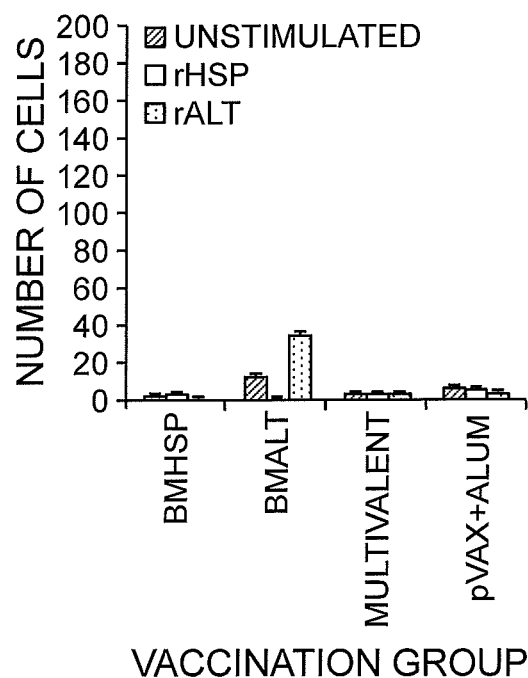

The immunological characteristics of the protective responses in vaccinated mice were determined by evaluating the secreted cytokine responses of spleen cells in response to the vaccine antigens. When spleen cells were stimulated with rBmHSP or rBmALT there was significant antigen-specific proliferation of spleen cells suggesting a strong recall cellular response to the antigens. To identify the cytokine profile of these antigen-responding cells, the IFN-γ and IL-4 secreting cells were counted using an ELISPOT assay. Results from these studies showed that spleen cells from mice vaccinated with multivalent vaccine were predominantly secreting IL-4 (FIG. 2). The numbers of IFN-γ secreting cells were very low. Overall, these findings indicated that vaccine-induced protection was largely mediated by Th2 type responses.

Example 3: BmVa1-1+BmALT2 Multivalent Vaccine

Sera.

Sera samples used in this study were from archived samples stored at the Mahatma Gandhi Institute of Medical Sciences, Sevagram, India. These samples were collected as part of epidemiological surveys in and around Wardha, an area endemic for lymphatic filariasis.

No demographic data was available to this study except that the sera samples were classified into microfilaremic (MF), chronic pathology (CP) or Endemic normals (EN) based on the detection of circulating parasites, parasite antigens or by evaluating clinical symptoms of lymphatic filariasis. Circulating microfilariae were detected in the blood of subjects according to known methods (Haslbeck, et al. (2005) *Nat. Struct. Mol. Biol.* 12:842-846; Yoo, et al. (2005) *Biotechnol. Lett.* 27:443-448). The presence of circulating antigen was detected using an Og4C3 kit and a WbSXP-based enzyme-linked immunosorbent assay (ELISA). Subjects with no circulating antigen or microfilariae were classified as EN, whereas subjects with circulating microfilariae and/or circulating antigen, as detected by ELISA, were considered as MF. Subjects showing lymphedema and other visible clinical symptoms of filariasis were grouped into CP. Control non-endemic normal (NEN) sera were collected at the University of Illinois Clinic at Rockford, IL Parasites.

*Brugia malayi* L3s were obtained from the NIAID/NIH Filariasis Research Reagent Resource Center (FR3) at the University of Georgia, Athens, GA.

Construction of Monovalent and Multivalent DNA Vaccines.

To prepare monovalent vaccine, codon optimized BmVAL-1 or Bmalt2 genes were cloned into the eukaryotic expression vector pVAX1 (Invitrogen, Carlsbad, CA) using insert-specific primers (Yoo, et al. (2005) supra; Huang, et al. (2005) *Immunol. Lett.* 101:71-80). To prepare multivalent vaccine, codon-optimized BmVAL-1 gene was first cloned into pVAX1 vector with no stop codon using already published primer sequences with a PstI site. Codon-optimized Bmalt2 gene was then inserted into this clone using gene-specific primers. PCR parameters for all the constructs were: 94° C. denaturation for 30 seconds, 50° C. primer annealing for 30 seconds, 72° C. primer extension for seconds for 30 cycles; and a final extension of 5 minutes was performed at 72° C. Insert DNA was sequenced to ensure authenticity of the cloned nucleotide sequence on both strands. Plasmids were maintained and propagated in *E. coli* TOP10F' cells. Plasmids were purified using endotoxin-free plasmid extraction kit (Qiagen, Valencia, CA). DNA was analyzed by agarose gel electrophoresis and quantified in a spectrophotometer (OD 260/280, ratio>1.8).

Expression and Purification of Recombinant Proteins.

Recombinant BmVAL-1 and rBmALT2 were expressed in pRSET-A vector and purified using an immobilized cobalt metal affinity column chromatography according to published methods (Norimine, et al. (2004) *Infect. Immun.* 72:1096-1106; Shinnick, et al. (1988) *Infect. Immun.* 56:446-451). Endotoxin in the recombinant preparations were removed by passing the recombinant proteins through polymyxin B affinity columns (Thermo Fisher Scientific, Rockford, IL) and the levels of endotoxin in the final preparations were determined using an E-TOXATE kit (Sigma, St Louis, MO) as per manufacturer's instructions. Endotoxin levels in the final preparations (0.005 EU/ml) were below detection limits in these recombinant protein preparations.

Immunoreactivity of Human Sera.

To determine if the human sera samples carried antibodies against BmVAL-1 or BmALT2, an ELISA was performed (Haslbeck, et al. (2005) supra; Yoo, et al. (2005) supra). For isotype-specific ELISA, alkaline phosphatase-conjugated goat anti-human IgG1, anti-human IgG2, anti-human IgG3, and anti-human IgG4 antibodies (Sigma) were used as the secondary antibodies.

Immunization Protocol for Mice and Jirds.

Six-week old male Balb/c mice and 35-40 gm outbred male mongolian gerbils (jirds) purchased from Charles River Laboratories (Wilmington, MA) were used in these experiments. Animals were treated as per the guidelines in the Guide for the Care and Use of Laboratory Animals. Two different animal models were used because *B. malayi* parasite does not mature into adults in mouse, so vaccine-induced protection against the L3 stages can be evaluated in the mouse model. In addition, significant immunological parameters can be measured in mice. Conversely, *B. malayi* parasite develops into mature adult worms in jirds. Therefore, vaccine-induced protection can be evaluated against adult worm establishment in jirds.

Three sets of experiments were performed: (1) monovalent BmVAL-1 vaccination, (2) monovalent BmALT2 vaccination and (3) multivalent mVAL-1/BmALT2 vaccination. Each experimental set had four groups (a) DNA prime plus DNA boost (homologous), (b) protein prime plus protein boost (homologous), (c) DNA prime plus protein boost (heterologous) and pVAX plus alum controls. Each group included ten (10) animals each. All animals were immunized subcutaneously with codon-optimized DNA (100 μg) in 50 μl volume or with recombinant protein (150 μg) plus alum in 50 μl volume. Control group received 100 μg of pVAX1 blank vector or 50 μl of alum. Blood samples were collected at frequent intervals, sera separated and stored at −80° C. The protocol used for immunizing mice and jirds was as follows. Animals were prebled and given a first dose on day 0. A second dose was administered on day 14 and subsequently bled. Third and fourth doses were administered on days 28 and 42, respectively, and the animals were subsequently bled. Mice were challenged on day 56 and protection was determined on day 58. Jirds were challenged on day 60 and protection was determined on day 155.

Protection Studies in Mice.

Challenge studies were conducted in mice by surgically implanting twenty live, infective *B. malayi* L3s into the peritoneal cavity in a micropore chamber (Veerapathran, et al. (2009) supra; Abraham, et al. (1988) supra). Aseptic conditions were followed for the surgical procedures. Forty-eight hours after implantation, chambers were recovered from the peritoneal cavity and viability of the larvae was determined under a light microscope. The percentage of protection was expressed as the number of dead parasites+ number of total parasites recovered×100.

Splenocyte Proliferation and Cytokine Assays.

Single-cell suspension of spleen cells ($0.5 \times 10^6$ cells per well suspended in 200 μl media) were prepared from each mouse and cultured in triplicate wells with either (1) 1 μg/ml rBmVAL-1, (2) 1 μg/ml rBmALT2, (3) 1 μg/ml rBmVAL-1+BmALT2, (4) a nonspecific recombinant protein (1 μg/ml of *Schistosoma mansoni* G-binding protein) or (5) were left unstimulated in the media. All cells were incubated for 3 days at 37° C. with 5% $CO_2$. After 3 days, $^3$H-Thymidine (0.5 lCi per well, Amersham Biosciences) was added to each well and further incubated. Cells were harvested 16 hours later and $^3$H-thymidine uptake was measured in a liquid scintillation counter and expressed as stimulation index (SI)=(counts per minute of stimulated cultures counts per minute of unstimulated cultures). Cell culture supernatants collected from the spleen cultures were assayed for IFN-γ, IL-4, IL-5 and IL-10 using an ELISA kit purchased from eBioscience Inc. (San Diego, CA).

BmVAL-1 and BmALT2 Specific IgG Antibodies in the Sera of Immunized Mice.

Titer of anti-BmVAL-1- and anti-BmALT2-specific antibodies was determined in the sera of immunized mice using an ELISA (Veerapathran, et al. (2009) supra; Gnanasekar, et al. (2004) Infect. Immun. 72:4707-15). Pre-immune sera served as controls. HRP-conjugated goat anti-mouse IgG was used as the secondary antibody (Thermo Fisher Scientific) for mouse assays. OPD (Sigma) was used as the substrate and optical density (OD) was measured at 405 nm.

Anti-BmVAL-1- and anti-BmALT2-specific IgG1, IgG2a, IgG2b, IgG3 and IgG4 antibodies were determined in the sera of mouse using a mouse antibody isotyping kit purchased from Thermo Fisher Scientific. All ELISAs were performed as per the manufacturer's recommendation and absorbance was read at 405 nm. Respective HRP-labeled goat anti-IgG isotype antibody was used as the secondary antibodies and color was developed using OPD substrate.

Challenge Studies in Jirds.

Jirds were challenged with 100 *B. malayi* L3s and worm establishment was determined on day 95 after challenge according to established methods (Weil, et al. (1992) supra). Jirds are permissive hosts for *B. malayi* and the worms mature into adult males and females in about 75 days. Presence of mature worms in the control group of jirds was confirmed by demonstrating microfilariae in their blood on day 80 after challenge. Percent reduction in the worm establishment was calculated using the formula: average number of worms recovered from control worms–average number of worms recovered from vaccinated animals/average number of worms recovered from control animals×100.

Statistical Analysis.

Statistical analysis was performed using SIGMASTAT program (Jandel Scientific, San Rafel, CA) and STATVIEW (SAS Institute, Cary, NC) software. Wilcoxon signed rank test was used to compare paired data; comparison between the groups was performed using the Mann-Whitney U test. p value of $p<0.05$ was considered statistically significant.

EN Individuals Carry High Titer of Antibodies Against BmVAL-1 and BmALT2.

Significant anti-BmVAL-1 and anti-BmALT2 IgG antibodies were present in the sera of EN subjects compared to MF subjects ($p<0.01$) and CP subjects ($p<0.005$). NEN subjects did not carry IgG antibodies against either of the antigens. Subsequent analysis of the IgG isotype of antibodies in the sera of EN subjects showed that anti-BmVAL-1 and anti-BmALT2 antibodies were predominantly of IgG1 and IgG3 isotypes.

High Titer of Antibody Responses in the Sera of Immunized Mice.

It has been shown that mice vaccinated with *B. malayi* antigens elicit significant host protective IgG antibodies. Therefore, IgG antibody titers in the sera of immunized mice were determined. Monovalent immunization with BmVa1-1 and monovalent immunization with BmAlt2 both elicited significant ($p<0.005$) titers of anti-BmVAL-1 and anti-BmALT2 IgG antibodies in the sera of mice. Compared to controls, the prime boost immunized group gave the maximum titer of antibodies followed by protein immunized and DNA immunized groups. Immunization with the multivalent vaccine formulation (BmVAL-1+BmALT2) also elicited significant IgG antibody titers against both rBmVAL-1 and rBmALT2 and the titers were comparable, indicating that the antigens do not interfere with each other or compete for dominance. An interesting finding was that the multivalent vaccine elicited significantly higher ($p<0.001$) titer of IgG antibodies in mice compared to any of the monovalent vaccines. These finding indicated that the two antigens in the multivalent formulation synergistically increased the vaccine-induced antibody responses.

Overall, protein vaccination elicited higher titer of IgG antibodies compared to DNA vaccines, indicating that protein vaccinations were highly immunogenic. Another observation was that a heterologous prime boost approach gave a higher seroconversion than homologous prime boost approach. Thus, overall heterologous prime boost approach appeared to stimulate the highest titer of antibodies.

IgG antibody subset analysis showed that BmVAL-1 vaccination elicited primarily IgG1 and IgG2a isotype of antibodies, whereas, BmALT2 vaccination induced IgG1, IgG2a and IgG3 isotype of antigen-specific antibody responses. Antigen-specific IgG4 antibody responses were not evident. The prime boost approach significantly amplified the IgG isotype responses. Following multivalent vaccination regimen IgG1, IgG2a and IgG3 subset of antigen specific antibodies were present in the sera of mouse.

Antigen-Specific Responses in the Spleen of Mice.

Spleen cells from immunized mice stimulated with either rBmVAL-1 or rBmALT2 proliferated significantly (SI 10.8±1.1 and SI 14.6±1.2, respectively) compared to the media control (SI 2.1±0.9). Spleen cells from mice immunized with the multivalent construct responded to both rBmVAL-1 (SI 18.9±2.6) and rBmALT2 (SI 23.5±3.1), indicating that a strong recall cellular response was generated to both BmVAL-1 and BmALT2 following vaccination with the multivalent construct.

Cytokine Analysis from Proliferated Culture Supernatants.

To identify the cytokine profile of the antigen-responding cells, the culture supernatant of mouse spleen cells stimulated with respective antigen (rBmVAL-1 or rBmALT2) was collected and the level of IFN-γ, IL-4, IL- and IL-10 was measured. These results showed that significant levels of IL-5 and IFN-γ were secreted by the spleen cells in response to rBmVAL-1. Spleen cells stimulated with rBmALT2 predominantly secreted IL-4 and IL-5.

Multivalent Vaccine Induces Significant Protection in Mice and Jirds.

The results herein indicated that significant IgG antibodies were elicited following vaccination with monovalent and multivalent vaccine preparations. To test if the immune responses elicited following vaccination were protective, vaccinated animals were challenged with live, third stage infective larvae (L3) of *B. malayi*. Since the parasites do not reach to maturity in mice, a standard micropore chamber challenge method was used (Gnanasekar, et al. (2004) supra). These studies showed that 39% to 74% protection was achieved in mice following immunization with monovalent vaccine (Table 9).

TABLE 9

| Vaccination Group | Mean ± SD Live L3s | Percent Protection |
|---|---|---|
| pVAXBmVAL-1 DNA monovalent homologous | 12.2 ± 4.5 | 39.0 ± 1.7%** |
| rBmVAL-1 protein monovalent homologous | 10.4 ± 3.1 | 48.0 ± 2.1%* |
| pVAXBmVAL-1 DNA plus rBmVAL-1 monovalent heterologous | 9.2 ± 2.2 | 54.0 ± 3.1%* |
| pVAXBmALT2 DNA monovalent homologous | 9.8 ± 2.1 | 51.0 ± 2.5%* |
| rBmALT2 protein monovalent homologous | 7.0 ± 1.1 | 65.0 ± 4.2%* |
| pVAXBmALT2 DNA plus rBmALT2 monovalent heterologous | 5.1 ± 0.5 | 74.5 ± 3.1%* |
| pVAXBmVAL-1/ALT2 DNA multivalent homologous | 8.6 ± 0.1 | 57.0 ± 2.2%* |
| rBmVAL-1/rBmALT2 protein multivalent homologous | 5.2 ± 1.1 | 74.0 ± 3.3%* |
| pVAXBmVAL-1/BmALT2 DNA plus rBmVAL-1/rBmALT2 multivalent heterologous | 4.4 ± 0.4 | 82.0 ± 2.2%* |
| pVAX + Alum control | 20 ± 0 | 0% |

Significance,
*p < 0.01,
**p < 0.05 compared to control.

Protein vaccination gave better results than DNA vaccination. The prime boost regimen gave the best results overall. Vaccination with BmALT2 gave higher percent of protection compared to BmVAL-1. Similarly, multivalent vaccination regimen gave the 57% to 82% protection compared to the monovalent vaccination regimen. These finding indicated that BmVAL-1 and BmALT2 synergistically enhance the protective immune responses in vaccinated animals when given as a multivalent vaccine.

Analysis of the thick blood smear prepared from the control group of jirds on day 80 after challenge showed that all five jirds were positive for microfilaria, whereas, microfilaria were not detected in the peripheral blood of vaccinated jirds. Fifteen (15) days later the animals were sacrificed and the male and female worms in the peritoneal, pelvic and pleural cavities were counted and the results between controls and vaccinated groups were compared (Table 10). Findings from vaccination of jirds also confirmed that the multivalent prime boost regimen gave the highest rate of protection. No female worms were recovered from the multivalent vaccinated animals.

TABLE 10

| Vaccination Group | Percent Production |
|---|---|
| pVAXBmVAL-1 DNA monovalent homologous | 50 ± 3.7% |
| rBmVAL-1 protein monovalent homologous | 40.0 ± 3.1% |
| pVAXBmVAL-1 DNA plus rBmVAL-1 monovalent heterologous | 52.4 ± 2.5% |
| pVAXBmALT2 DNA monovalent homologous | 58.3 ± 2.1% |
| rBmALT2 protein monovalent homologous | 72.0 ± 5.5% |
| pVAXBmALT2 DNA plus rBmALT2 monovalent heterologous | 78.5 ± 3.2% |
| pVAXBmVAL-1/ALT2 DNA multivalent homologous | 77.1 ± 2.0% |
| rBmVAL-1/rBmALT2 protein multivalent homologous | 79.9 ± 3.5% |
| pVAXBmVAL-1/BmALT2 DNA plus rBmVAL-1/rBmALT2 multivalent heterologous | 85.0 ± 1.4% |
| pVAX + Alum control | 0 |

Significance, p < 0.01 compared to control.

Example 4: BmHSP+BmALT2+BmTSP Multivalent Vaccine

Parasites.

*Brugia malayi* L3s were obtained from the NIAID/NIH Filariasis Research Reagent Resource Center (FR3) at the University of Georgia, Athens, GA.

Construction of pVAX Bmhp+Bmalt2-1-Bmtp DNA Vaccine.

The codon-optimized DNA sequence coding for Bmhsp was amplified with the forward primer 5'-CGC GGA TCC ACC GTG ATC CAT TGT CG-3' (SEQ ID NO:25) containing BamHI restriction site and the reverse primer 5'-AAC TGC AGC TGT TTT CCA TTT CCA TTC-3' (SEQ ID NO:26) containing PstI restriction site without the stop codon and cloned into pVAX vector. The resulting plasmid was designated as pVAX Bmhsp*. Codon-optimized Bmalt2 gene was amplified with the forward primer 5'-AAC TGC AGA TGG GTA ACA AGC TCC TCA TCG-3' (SEQ ID NO:27) and the reverse primer without the stop codon 5'-CGC GAA TTC GGC GCA CTG CCA ACC TGC-3' (SEQ ID NO:28). Underlined sequences indicate PstI and EcoRI restriction sites in the forward and reverse primers, respectively. The amplified Bmalt2 DNA insert was then subcloned into pVAX Bmhsp* plasmid at the PstI and EcoRI restriction sites, resulting in pVAX Bmhsp+Bmalt2* plasmid. To clone the final product of pVAXBmhsp+Bmalt2+Bmtsp plasmid, the gene sequence encoding Bmtsp ECL domain alone was amplified with the forward primer 5'-CGC GAA TTC ACC ATG GTC CTG GAG-3' (SEQ ID NO:29) containing EcoRI restriction site and the reverse primer with stop codon 5'-GCT CTA GAT CAG TCC TTC TGG CTA G-3' (SEQ ID NO:30) containing XbaI restriction site and cloned into pVAX Bmhsp+Bmalt2* plasmid. Bivalent constructs of HSP+TSP, TSP+ALT and HSP+ALT were also constructed with their respective primers.

Construction of pRSETA Bmhsp+Bmalt2+Bmtsp, a Multivalent Fusion Protein.

The Bmhsp+Bmalt2+Bmtsp fusion protein was constructed in the same manner as above. The primer sequences of HSP, ALT2 and TSP were as follows. Bmhsp, forward primer, 5'-CGG GAT CCA TGG AAG AAA AGG TAG TG-3' (SEQ ID NO:31) containing BamHI and reverse primer, CCC TCG AGT GCT TTC TTT TTG GCA GC-3' (SEQ ID NO:32) containing XhoI. Bmalt2, forward primer, 5'-OCC TCG AG A TGA ATA AAC TTT TAA TAG CAT-3' (SEQ ID NO:33) containing XhoI or 5'-AAC TGC AGA TGG GTA ACA AGC TCC TCA TCG-3' (SEQ ID NO:27) and reverse primer, 5'-GGG TAC CCG CGC ATT GCC AAC CC-3' (SEQ ID NO:34) containing KpnI. Bmtsp, forward primer, 5'-GGG GTA CCC CGG CAA GGA TCA ATT TAA AA-3' (SEQ ID NO:35) containing KpnI and reverse primer, 5'-CGG AAT TCT CAA TCT TTT TGA GAT GAA T-3' (SEQ ID NO:36) containing EcoRI were used to amplify the Bmtsp fragment of SEQ ID NO:77. Primers were also designed to amplify a Tetraspanin Large Extracellular Loop (LEL) fragment of SEQ ID NO:63. Bivalent constructs (HA, HT and TA) were also cloned individually into a pRSETA vector.

Immunization of Animals.

Six-week-old Balb/C mice were immunized with 100 µg of DNA intradermally (i.d.) as DNA vaccine or with 15 µg of recombinant protein subcutaneously (s.c.) as protein vaccine or with two doses of DNA and two doses of protein as prime-boost vaccine. Mice were randomly divided into 15 groups with 5 mice per group. Animals from groups 1-3 were immunized with HSP+ALT2 (HA). Groups 4-6 were immunized with HSP+TSP (HT), and 7-9 were immunized with TSP+ALT2 (TA). Mice from groups 10-12 were immunized with the multivalent vaccine HSP+ALT2+TSP (HAT). Control group of animals received pVAX vector and/or alum (Infectious Disease Research Institute (IDRI)). This experiment was repeated twice with all the groups.

Analysis of Antibody Response in Immunized Animals.

IgG antibody levels in the sera of immunized and control groups of animals against all the three proteins were determined using an indirect ELISA (Anandharaman, et al. (2009) supra). Briefly, wells of a 96-well microtiter plate were coated with recombinant proteins (rHSP, rALT2 or rTSP; 1 µg/ml) in carbonate buffer, pH 9.6, overnight at 4° C. and blocked with 3% BSA for 1 hour at 37° C. Sera samples were added to the wells and the plates were incubated overnight at 4° C. After washing, HRP-labeled mouse anti-human IgG was added (1:5000) and incubated further for 1 hour at 37° C. The color was developed with OPD (o-phenylene diamine) substrate (Sigma Aldrich, USA). Absorbance was measured at 450 nm in a microplate reader (BIO-RAD, Hercules, CA).

Immunoblot analysis was also performed with the immunized mice sera. Sera samples from the mice immunized with the recombinant proteins (rHAT, rALT2, rTSP or rBmHAT) were used for the immunoblot study. The color of the blot was developed with the diaminobenzidine (DAB) substrate.

ADCC Assay.

To evaluate the protection efficacy of the antigen combinations, in vitro ADCC was performed with the sera from the mice immunized with bivalent and trivalent vaccine constructs. The in vitro ADCC assay was performed according to known methods (Chandrasekhar, et al. (1990) supra). Briefly, Peritoneal Exudates Cells (PEC) were collected from normal Balb/c mice by washing the peritoneal cavity with sterile RPMI 1640 media. The cells were washed and suspended in RPMI 1640 medium supplemented with 10% Fetal Calf Serum (FCS). Ten $L_3$ of $B.$ $malayi$ were added to $2 \times 10^5$ peritoneal exudates cells (PEC)/well in 96-well culture plates (Thermo Fisher Scientifics, USA.), 50 µl of immunized mice sera and 50 µl of RPMI 1640 media were added to the wells in triplicates and incubated for 48 hours in 5% $CO_2$ at 37° C. Larval viability was determined microscopically after 48 hours of incubation. Larvae that were limpid, damaged and with the clumps of cells adhered to it were counted as dead. ADCC was estimated as the percent larval death calculated using the formula: Number of Dead larvae÷Total number of larvae×100.

Depletion of IgG Antibodies from the Sera Samples.

Sera from mice immunized with multivalent vaccine was depleted of recombinant antigen specific IgG antibodies using cobalt IMAC resin coupled with his-tagged recombinant antigens (Anandharaman, et al (2009) supra). Briefly, 1 mg of his-tagged recombinant protein (rHSP) was coupled to 2 ml bed volume of IMAC resin for 2 hours at 37'C. The cobalt column was washed with ten bed volumes of PBS (pH.8) and incubated overnight at 4° C. with 200 µl of pooled sera from the mice immunized with multivalent vaccine. Supernatant containing the depleted sera was collected by centrifugation. Anti-HSP-depleted serum was incubated overnight at 4° C. in rALT2-coupled column. The supernatant containing anti-HSP- and anti-ALT2-depleted serum was collected and incubated in rTSP-coupled column. Anti-HSP-, anti-ALT2-, and anti-TSP-depleted serum was collected and used. Depletion of IgG antibodies against specific antigens was confirmed by ELISA as described above. Antibody-depleted sera were then used in an ADCC assay.

Analysis of In Situ Cytotoxicity Against L3 Larvae in Immunized Mice (Micropore Chamber Technique).

The protective efficacy of vaccination was analyzed by challenging the immunized animals with infective L3 using micropore chamber method (Abraham, et al. (1989) supra). Micropore chambers were assembled using 14×2 mm PLEXIGLASS (acrylic) rings and 5.0 µm NUCLEOPORE polycarbonate membranes (Millipore Corporations, Bedford, MA). After 48 hours of implantation, animals were sacrificed and the chambers were recovered from peritoneal cavity. Contents of each chamber were examined microscopically for cell adherence and death of infective L3. The parasite was considered dead if it was not motile and limpid, and had several adherent cells on the surface. The percentage protection was calculated using the formula: number of dead parasites number of recovered parasites×100. This experiment was repeated twice with five animals in each group.

Splenocyte Proliferation.

Vaccinated and control mice were sacrificed on day 60 and the spleens were removed aseptically. Single-cell suspensions were prepared in RPMI 1640 medium supplemented with 10% heat-inactivated FCS, passed through a NYLON (aliphatic polyamide) mesh (BD Biosciences, Bedford, USA). After determining the viability of cells using trypan blue dye exclusion, approximately $2 \times 10^6$ cells per well in triplicates were plated in 96-well culture plates (ThermoFisher, USA). The splenocytes were stimulated with 1 µg/100 µl/well of recombinant proteins (rHSP, rALT2 or rTSP) or ConA or with medium alone (Unstimulated) for 72 hours at 37° C. in the atmosphere of 5% $CO_2$. Cell proliferation was determined using cell counting kit (CCK-8) purchased from Dojindo Molecular Technologies, Inc. (Gaithersburg, MD). Stimulation index of spleen cell proliferation was calculated using the formula: Absorbance of stimulated cells Absorbance of unstimulated cells. All cultures were taken in triplicates and the results expressed as mean S.I.±SEM.

Real Time-PCR (RT-PCR).

Cytokine levels in the mRNA of the spleen cell pellets were analyzed by real time-PCR. The spleen cells of vaccinated and control group mice were cultured as above at a concentration of $2 \times 10^6$ cells/100 µl/well in 96-well plates and stimulated with recombinant antigens (1 µg/ml). After 72 hours, cells were centrifuged (1000 rpm for 5 minutes) and total RNA was extracted from the cell pellets using TRIZOL (phenol, guanidinium and thiocyanate) reagent (Invitrogen) as per description of the manufacturer. Followed by RNA extraction, first-strand cDNA was synthesized by $RT^2$ First Strand Kit (SuperArray Bioscience Corporation, Frederick, MD). PCR array analysis was performed according to the manufacturer protocol with the $RT^2$ Real-Time™ SYBR Green (cyanine dye) PCR Master Mix. Aliquots from this mix were added to a 96-well plate, where each well contained predispensed gene-specific primer sets. Relative quantification of the genes of interest that expressed was measured in an Applied BioSystem 7300 real-time PCR machine (Applied BioSystems, Foster City, CA). Cycling parameters were as follows: 95° C. for 10 minutes for activation of HOTSTART DNA polymerase, followed by 40 cycles of denaturation at 95° C. for 15 seconds and primer extension at 60° C. for 1 minute. RT-PCR data array set was generated and analyzed using SABiosciences web-based data analysis system. Results were expressed in terms of fold change of immunized mice compared to control mice by normalizing the expression of housekeeping genes.

Cytokine Assay.

Splenocyte cell culture supernatants were collected after 72 hours incubation stimulated with recombinant antigens (1 µg/ml) or with medium alone. Secreted levels of IL-4 and IFN-γ cytokines in the culture supernatants were determined using a sandwich ELISA kit purchased from Thermo Scientifics, USA. All concentrations were derived from standard curves and data expressed in pg/ml.

Construction of cHAT Plasmid and Expression of Fusion Proteins.

Since the N-terminal region of HSP is involved in IL-10 binding, this region was deleted and cHAT recombinant protein was prepared as 37 KDa His-tagged protein.

Construction of Recombinant Plasmids and Expression of Fusion Proteins. The full-length hsp, alt2 and tsp genes of B. malayi L3 stage were constructed with the expected size (850 bp). These fragments were further directionally cloned into the expression vectors pVAX1 and pRSETA with the specified restriction enzyme cutting sites. Results of the DNA sequence analysis confirmed gene insertion direction. rBmHAT was expressed as a 45 KDa His-tagged fusion protein, which was purified and analyzed in SDS-PAGE. The results indicated that the fusion protein was pure without any contaminating proteins. The presence of antibodies against all the three antigens was confirmed by immunoblot analysis.

Antibody Titer in the Immunized Mice Sera.

The mean peak antibody titer of the sera samples from the mice immunized with prime-boost or protein vaccine was significantly higher (p<0.001) compared to the DNA group. Sera collected from rBmHAT-immunized animals showed the maximum titer of 30,000 against rALT2 antigen, while the antibody titer against rHSP or rTSP antigen was in the range of 18,000-20,000. Similarly, the mice immunized with the bivalent vaccine showed the maximum titer of 30,000 against ALT2 antigen while anti-HSP and anti-TSP antibodies were in the range of 8,000-15,000.

Antibody-Dependent Cell-Mediated Cytotoxicity.

Antibody-mediated adherence and cytotoxicity of immune cells to B. malayi L3 larvae was observed after 48 hours of incubation of parasites, with the sera and normal immune cells. ADCC showed maximum cytotoxicity of approximately 90% (p<0.001) in the sera of mice immunized with rBmHAT or rWbHA vaccine constructs (Table 11). Bivalent vaccine constructs of rWbHT and rWbTA also gave better protection of 82% and 87%, respectively, which was significant compared to monovalent-vaccinated and control animals (p<0.001). To evaluate the protection mediated by the antibodies generated against HSP, ALT and TSP antigens, IgG antibodies were depleted from the immunized sera and used in ADCC. Depleted antibodies showed only 6% protection against L3.

TABLE 11

| Groups | % Cytotoxicity |
| --- | --- |
| H + A | 90 ± 2.4* |
| H + T | 82.30 ± 12.9* |
| T + A | 87.06 ± 9.8* |
| H + A + T | 88.69 ± 7.5* |
| anti-HSP + anti-ALT + anti-TSP antibodies depleted from HAT immunized sera | 5.55 ± 1.5 |

Values represent mean ± SD of three wells.
*Significant larval death (P < 0.001) compared to other mice groups.

In Situ Protection Study.

Two weeks after the final immunization, the ability of the vaccine candidates, to kill the filarial parasites in the immunized animals was evaluated by in situ micropore chamber studies. The data was combined from the two similar experiments and represented as mean count±SEM. The analysis of percentage reduction in worm burden compared with control showed that multivalent vaccine (HAT) conferred the maximum protection of 100% and 94% for protein and prime-boost vaccine, which was very significant protection (Table 12) (P<0.0001) compared to control groups (5%). Interestingly, the percentage worm reduction of bivalent vaccines HA, TA and HT were 90%, 80% and 82%, respectively, which was also significantly high compared to the control. In the entire bivalent vaccine group, prime-boost vaccination was more protective compared to DNA and protein vaccination.

TABLE 12

| Trial 1 DNA Vaccine | | Trial 2 Protein Vaccine | | Trial 3 Prime-Boost Vaccine | |
| --- | --- | --- | --- | --- | --- |
| Group | % Cytotoxicity | Group | % Cytotoxicity | Group | % Cytotoxicity |
| pVAX | 5 ± 4.23 | Alum | 3 ± 4.23 | pVAX + Alum | 5.9 ± 4.23 |
| H + A | 81 ± 11.23* | H + A | 78 ± 11.23* | H + A | 90 ± 11.23* |
| H + T | 72 ± 12.03* | H + T | 69 ± 12.03* | H + T | 80 ± 12.03* |
| T + A | 74 ± 11.21* | T + A | 66 ± 11.21* | T + A | 82 ± 11.21* |
| H + A + T | 91 ± 11.92* | H + A + T | 100 ± 0* | H + A + T | 94 ± 11.92* |

Values are mean ± SD. N = 5. Data is from one of two similar experiments showing comparable results.
*Significant larval death (P < 0.001) compared to other mice groups.

Splenocyte Proliferation.

Spleen cells isolated from vaccinated and control animals were stimulated in vitro individually with rHSP, rALT2 or rTSP to analyze the protein-specific T-cell proliferation in vaccinated animals. Mice immunized with the prime-boost regimen in all the vaccine combinations and HAT as protein vaccine gave the highest protection. Hence the splenocytes were collected only from these animals analyzed for the immune response. Splenocytes from bivalent- and trivalent-vaccinated animals stimulated with respective recombinant proteins showed significantly high (P<0.001) proliferation (mean S.I.=4.25-5.8) when compared to monovalent and unstimulated controls. The proliferation index of spleen cells immunized with the monovalent construct showed significant proliferation. The stimulation of cells was comparable to the positive controls.

RT-PCR Array.

To determine the cellular immune responses to multivalent constructs in the vaccinated mice, spleen cells collected from vaccinated and control mice were cultured in the presence of respective recombinant proteins and their proliferative responses and cytokine profiles were evaluated. Since the spleen cells from vaccinated animals were proliferating significantly to recall response, levels of cytokine mRNA were measured. An RT-PCR cytokine gene array was performed on mRNA collected from the spleen cells stimulated with recombinant proteins. These results showed that both Th1 (IFN-γ, IL-2) and Th2 (IL-4) cytokine genes were significantly increased in vaccinated animals.

Cytokine Levels.

After identifying the presence of IFN-γ and IL-4 cytokine expression in the mRNA isolated from the vaccinated spleen cells, the secretion of same cytokines in the supernatant was investigated. The data were normalized with the unstimulated controls. Interestingly, the cytokine profiles observed in the supernatant exhibited significantly higher levels of IFN-γ showing a Th1-biased immune response. These results demonstrated that recombinant proteins stimulated the production of IFN-γ and induced a Th1-mediated protective response.

Example 5: Analysis of cHAT Vaccine in Various Adjuvant Formulations

Preparation of cHAT.

Previous studies showed that the N-terminal sequence of BmHSP12.6 can bind to human IL-receptor and trigger IL-10-mediated responses (Gnanasekar, et al. (2008) *Mol. Biochem. Parasitol.* 159(2):98-103). Since IL-10 is an immunosuppressive agent, the IL-10 receptor binding sequences were deleted from HSP. The truncated sequence was referred to as cHSP. The cHSP was then used to replace the HSP gene and HSP protein in the multivalent HAT hybrid vaccine. Thus, the resulting new vaccine was called cHAT.

Protection Studies Using cHAT-Fusion Protein Vaccine in Mice.

Mice were immunized with four doses of cHAT fusion protein at two week intervals. One month after the final immunization, the ability of the vaccine candidates to kill the filarial parasites was evaluated by in situ micropore chamber studies. Results showed that when mice were immunized with cHAT fusion protein with alum as the adjuvant, the vaccine conferred 81% protection (Table 13) (P<0.0001) compared to control groups (2%) that received only phosphate-buffered saline (PBS) and alum. Different adjuvants were then tested to see if changing the adjuvant would improve the protection ability of cHAT. Two additional adjuvants were tested: alum containing a TLR4 agonist (purchased from Infectious Disease Research Institute, Seattle, WA) and ALHYDROGEL (purchased from Sigma, St. Louis, MO). cHAT with no adjuvants remained as a control. Results from these studies (Table 13) showed that 78% protection was achieved with alum plus TLR4 agonist and cHAT given in ALHYDROGEL adjuvant gave 70% protection. An interesting finding in these studies was that cHAT without any adjuvant also gave 72% protection indicating that the cHAT fusion protein vaccine could be administered without any adjuvant and still obtain significant protection.

TABLE 13

| Group | % Larval Death (Mean ± SD) |
| --- | --- |
| cHAT + Alum | 81 ± 7.8 |
| PBS + Alum Control | 1.7 ± 1.3 |
| cHAT + Alum with TLR4 agonist | 78 ± 8.4 |
| cHAT + ALHYDROGEL | 70 ± 13 |
| cHAT With No adjuvant | 72 ± 12 |

Values are mean ± SD. N = 5. Data is from one of two similar experiments showing comparable results.
*Significant larval death (P < 0.001) compared to other mice groups.

Example 6: Homologues of HSP, ALT2 and TSP

Homologues of the vaccine antigens, HSP, ALT2 and Tetraspanin are present in *O. volvulus* and *L. boa*. Comparison of the nucleotide sequence of HSP, ALT2 and Tetraspanin from *O. volvulus* and *L. boa* show that there is significant sequence homology (>90%) between the proteins from all filarial parasites. These findings indicate that the cHAT fusion protein vaccine developed in Example 5 can be used as a vaccine against *O. volvulus* and *L. loa*.

Figure 4:
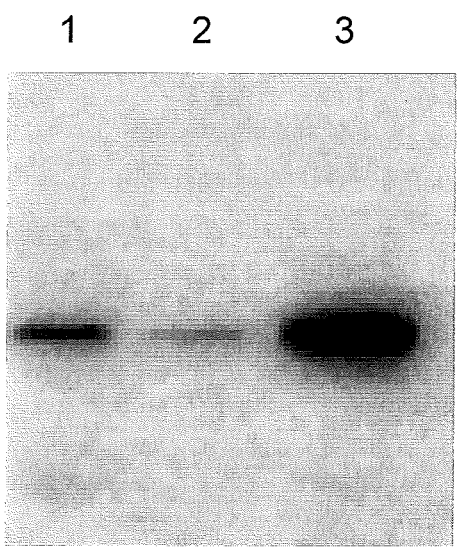
FIG. 4 shows a western blot of recombinant BmTSP (lane 1) and two different fractions of isolated, recombinant *O. volvulus* TSP (lanes 2 and 3) probed with sera from cHAT-vaccinated mice.

As an example, *O. volvulus* tetraspanin was cloned from *O. volvulus* L3 cDNA library and recombinant proteins were prepared. Sera sample from mice vaccinated with cHAT vaccine that gave the 81% protection in Table 13 was used to probe the recombinant *O. volvulus* tetraspanin after separating the protein in a 12% SDS-PAGE gel. *B. malayi* tetraspanin was used as a positive control. Results showed that the sera sample significantly reacted with *O. volvulus* tetraspanin (FIG. 4) thereby indicating that the cHAT vaccine developed in Example 5 is of use as a vaccine against *O. volvulus*.

Example 7: Multivalent Vaccine Against Lymphatic Filariasis in Rhesus Macaque Model Parasites. *B. malayi* infective third stage larvae (L3) were obtained from the NIAID/NIH Filariasis Research Reagent Resource Center (University of Georgia, Athens, GA).

Multivalent Fusion Protein rBmHAT.

The multivalent fusion protein rBmHAT expressed in *Escherichia coli* BL21 (pLysS), was purified and endotoxin removed by Pierce High Capacity Endotoxin removal resin column (Thermo Fisher Scientific, Rockford, IL) as described herein.

Immunizations of rBmHAT.

Five macaques each received 200 pg of rBmHAT vaccine mixed with 100 µg of AL007 alum (IDRI, Seattle, WA) under ABSL-2 conditions. Five (5) macaques that received alum (AL007) only remained as controls. Each animal was anesthetized with ketamine/xylazine and the vaccine was administered intramuscularly in each thigh (one injection site per thigh per vaccination). Animals were immunized at 4-week intervals on days 0, 28 and 56. Intramuscular route is commonly used for clinical vaccine trials and hence the same procedure was followed for macaques. The injection sites were monitored daily for signs of fever, any adverse reactions (redness, swelling, etc.) for up to 7 days post immunization.

B. malayi L3 Challenge.

On day 84, one month after the final dose of vaccine, macaques were anesthetized with ketamine HCl and challenged subcutaneously with 400-500 B. malayi L3. To facilitate the production of the relatively large number of L3 (500 L3/animal) required for challenging immunized macaques, the animals were divided into 2 subgroups within each group. The subgroups were challenged one week apart. Before challenge, B. malayi L3 were counted and examined for viability under a microscope. Only viable parasites were used for challenge.

Monitoring of Each Animal after Challenge.

All animals were monitored daily for clinical signs after the challenge. Behavioral observations were similarly conducted during the entire post-challenge period. Clinical monitoring included serum chemistry, hematology, complete blood count (CBC) analysis (IDEXX) and CD4+/CD8+ T cell flow cytometry analysis. Body weights, body condition, lymphoedema and lymph node measurements were also recorded each time the animal was sedated for procedures (like immunizations, challenge, and blood collections).

Sample Collection.

Blood samples and peripheral blood mononuclear cells (PBMC) were collected. Whole blood was collected into BD VACUTAINER SST tubes according to manufacturer's instructions. Heparinized blood (1 ml) was collected from the femoral vein of each animal during the immunization period and from the saphenous vein during the challenge period. The shift in blood collection site was to eliminate any potential interference with the inguinal lymph node measurements or assessments of edema. Blood samples were obtained at multiple time points during the entire follow-up period.

Isolation of PBMC.

The blood pellets after plasma separation was diluted in phosphate-buffered saline (PBS; 1:2) and subjected to gradient density centrifugation for 30 minutes at 2200 rpm using a 90% HISTOPAQUE separation solution (Sigma, St. Louis, MO). The opaque interface containing mononuclear cells was collected, washed three times in PBS by centrifugation at 800 rpm. PBMC were enumerated using Trypan blue dye exclusion method and resuspended in RPMI 1640 medium containing 10% FBS (100 U/ml Penicillin/Streptomycin, and 2 mM L-glutamine). PBMC collected before the challenge was analyzed for T cell proliferation and IFN-γ secretions. PBMC collected after the challenge experiments were tested for T cell proliferation and ELISPOT assays. Proliferation assay was performed with PBMC isolated on the same day of blood collection. PBMC suspended in RPMI media with 10% FBS were used for ADCC assay and for cytokines analysis.

T Cell Proliferation and Flow Cytometry.

Carboxyfluorescein diacetate succinimidyl ester (CFSE)-based assay was used for assessment of antigen-specific proliferation within the T cell population (Parish, et al. (2009) Curr. Protoc. Immunol. Chapter 4: Unit 49). A 5 mM CFSE stock solution (Invitrogen, Grand Island, NY) was prepared according to manufacturer's instructions. PBMC collected four weeks after the final immunization were gently resuspended at $10^7$ cells/ml in 5 µM CFSE and incubated in the dark at 37° C. for 15 minutes. Cells were centrifuged and washed with RPMI containing 10% FBS (100 U/ml Penicillin/Streptomycin, and 2 mM L-glutamine) and incubated for an additional 30 minutes at 37° C. Cells were then washed, resuspended in RPMI containing FBS, plated in a 24-well plate at $2 \times 10^6$ cells/ml per well and incubated overnight at 37° C. The medium (~500 µl) was removed the following day and cells were stimulated with 1 µg/mL of rBmHAT. Samples incubated only with RPMI medium served as negative controls. As a positive control for each animal, cells were stimulated with phytohemagglutinin (PHA). Cells were cultured and harvested after 5 days of stimulation. Following a washing step with PBS/0.2% FBS, cells were surface stained with an antibody cocktail of CD3-APC-Cy, CD4-PE and CD8-PerCP and incubated for 20 minutes at room temperature. After an additional washing step with PBS/0.2% FBS the cells were acquired on BD FACS CANTO II flow cytometer (BD, San Jose, CA) and analyzed on a BD FACS DIVA Software v6.1.2. At least 50,000 events within the live lymphocyte gate were acquired.

Cell Counts, Serum Chemistry and Complete Blood Count (CBC) Analysis.

CBC, serum chemistries and eosinophil counts were analyzed using commercial automated hematology and serum chemistry analyzers by IDEXX. Samples collected prior to the initiation of the study served as a normal reference baseline for each animal.

Measurement of Secreted Levels of IFN-γ.

PBMC ($1 \times 10^6$ cells) were stimulated in vitro with 1 µg/ml of rBmHAT for days at 37° C. Following stimulation, the supernatants were harvested and assayed for secreted levels of IFN-γ using an ELISA kit (Mabtech AB, Ashburn, VA) according to manufacturer's instructions.

ELISPOT Assay.

An ELISPOT assay was performed to determine the antigen-specific IFN-γ and IL-10 secreting cells in the PBMC of vaccinated and control macaques. A monkey ELISPOT kit purchased from U-Cytech biosciences (Yalelaan, The Netherlands) was used to determine the spot forming units as per the manufacturer's instruction. PBMC collected 20 weeks post challenge were plated in 96-well plates at $1 \times 10^6$ cells/ml and were stimulated with 100 ng/well of B. malayi adult soluble antigen (BmA) for 24 hours at 37° C. and 5% $CO_2$. Wells of ELISPOT plates were coated with 100 µl/well of capture antibodies (anti-IL-10 or anti-IFN-γ) diluted in sterile coating buffer and incubated overnight at 4° C. Plates were washed 2 times with sterile coating buffer. After blocking the plates with 200 µl/well of blocking buffer for 1 hour at room temperature, PBMC that were already stimulated with BmA antigens or only media (negative control) were added to the wells of the ELISPOT plates at 100 µl/well and incubated for 24 hours at 37° C. and 5% $CO_2$. All the cells were removed from the plates and the membrane was washed 3 times with sterile PBS. Following wash, 100 µl of detection antibodies were added to each well and incubated at room temperature for 2 hours. After washing the plate 4 times with wash buffer, avidin-HRP reagent was added (100 µl/well) and incubated for 45 minutes at room temperature. After a final wash with PBS, freshly prepared 3-amino-9-ethylcarbazole (AEC) substrate solution was added (100 µl/well) and monitored for the development of spots at room temperature for 10-60 minutes. The substrate reaction was stopped by washing wells 3 times with 200 µl/well ultrapure water. The plates were air dried.

Spots were counted using a dissecting microscope. The plates were stored in the dark prior to reading. Antigen-specific responses were determined by subtracting the number of spots in the negative control wells from the wells containing antigens. Results are shown as the mean value of spots obtained from triplicate wells.

Analysis of Serum Antibody Titers in Macaques.

Levels of IgG, IgG1, IgG2, IgG3, IgA and IgE antibodies against rBmHSP, rBmALT2, rBmTSP or rBmHAT were determined in the sera (collected one month after the final dose of vaccine) of each rhesus macaque using an indirect ELISA as described herein. Briefly, wells of a 96-well microtiter ELISA plates were coated with 100 ng/well of antigens (rBmHSP, rBmALT2, rBmTSP or rBmHAT) in 0.05 M carbonate-bicarbonate buffer, pH 9.6. The wells were blocked with 3% BSA in 0.05% PBS-TWEEN 20 (PBS-T), and 100 μl of sera samples (diluted in the range of 1:100-1:50,000 in PBS-T) from each macaque were added to each well. Goat anti-monkey IgG antibodies conjugated to peroxidase (Rockland Immunochemicals, Gilbertsville, PA) was used as secondary antibodies to determine IgG titer antibodies. The color was developed using OPD substrate and absorbance was read at 492 nm in the ELISA reader (BioRad, Hercules, CA). To determine the levels of isotype antibodies, biotinylated anti-monkey IgG1 (1:2000), IgG2 (1:200), IgG3 (1:2000), IgA (1:2000) and IgE (1:1000) antibodies (NHP Reagent Resources, Boston, MA) were used as secondary antibodies. After washing the plates, optimally diluted streptavidin conjugated horse radish peroxidase (HRP) was added and further incubated for 60 minutes at room temperature and the color was developed.

ADCC Assay.

PBMC were prepared from heparinized whole blood from a naive healthy animal as described above. Briefly, ten $B. malayi$ L3 (suspended in 50 μl RPMI 1640 medium containing 10% FBS) were incubated with $2\times10^5$ PBMC (in 50 μl RPMI 1640) and 50 μl of serum from each animal (collected one month after the final dose of vaccine) in a 96-well round bottom tissue culture plate. Five replicates were performed for each serum sample. Control wells contained $B. malayi$ L3 incubated in media, with sera alone or cells alone. The plates were incubated at 37° C. with 5% $CO_2$ for 48 hours. Following incubation, $B. malayi$ L3 were examined under a microscope at 24 and 48 hours to determine larval viability. Dead L3 were defined as those having a limpid or straight appearance with no movements for an additional observation period of 8 hours at 37° C. Live larvae were active, coiled and motile. The percentage larval death was expressed as the ratio of the number of dead L3 to that of the total number recovered within the experimental period multiplied by 100. Average larval death in 5 wells were calculated and expressed as percent protection in each animal.

Knott Test to Determine Microfilaremia (Mf) in Macaques.

The presence of Mf in the blood of macaques was detected using the Knott technique as described previously (Liu, et al. (1989) $J. Trop. Med. Hyg.$ 92:93-96). Peripheral blood of macaques was screened weekly for Mf starting from 5 weeks to 20 weeks post challenge. Briefly, whole blood was mixed with 9 ml of a 2% formalin solution (prepared in PBS) in a 15 ml conical centrifuge tube. The tubes were gently rocked for 2 minutes at room temperature and centrifuged at 1,500 rpm for 5 minutes. The supernatant was then thoroughly decanted by turning the tube completely upside down to remove all the liquid. Following this 5 ml of ACK lysis buffer (Quality Biologicals, Gaithersburg, MD) was added to the pellet and the tube was vortexed. Two to three drops of methylene blue solution (Fisher Scientific, Hannover Park, IL) was then added to the tubes, gently mixed, and smeared onto five glass slides. The samples were allowed to dry and read under a microscope using 40× lens objective. A comparison of Mf counts in blood collected from the saphenous and femoral veins showed similar results.

Detection of Mf in the Peripheral Blood by PCR.

PCR-based assays are more sensitive in detecting the presence of Mf in the blood samples (Mishra, et al. (2005) $Acta Trop.$ 93:233-7; Tao, et al. (2006) $J. Clin. Microbiol.$ 44:3887-93). Therefore, the PCR based assay was also used to confirm the presence of Mf in the blood samples of all macaques 20 weeks after challenge. Whole blood samples were centrifuged at 10,000 rpm for 5 minutes and the supernatant containing serum was stored at −20° C. DNA was isolated from the pellet using DNEASY Blood & Tissue Kit (Qiagen, Valencia, CA) according to the manufacturer's instruction. Primers were synthesized at Integrated DNA Technologies Inc., (Coralville, IA) for HhaI tandem repeats. Primer sequences for HhaI tandem repeats were: Forward 5'-GCG CAT AAA TTC ATC AGC-3' (SEQ ID NO:75) and Reverse 5'-GCG CAA AAC TTA ATT ACA AAA GC-3' (SEQ ID NO:76). PCR parameters were initial denaturation of 94° C. for 5 minutes, followed by 40 cycles of 1 minute at 94° C., 1 minute at 56° C., 1 minute at 72° C. and a final extension of 10 minutes at 72° C. Following PCR reaction, 10 μl of each PCR product was analyzed on a 1% agarose gel.

PBMC Proliferations Assay.

PBMC collected 10 weeks post-challenge were cultured in 96-well tissue culture plates at a concentration of $1\times10^6$ cells/well in RPMI 1640 supplemented with 10% FCS. Cells were stimulated either with rBmHAT antigen (1 mg/ml) or Concanavalin A (1 mg/ml) or with medium alone (unstimulated) in triplicate wells. PBMC were stimulated in triplicate wells and the plates were incubated at 37° C. in 5% $CO_2$. After 72 hours, cell proliferation was measured using cell counting kit (CCK-8) (Dojindo Molecular Technologies, Inc., Gaithersburg, MD). Stimulation index of PBMC proliferation was calculated using the formula: Absorbance of stimulated cells/Absorbance of unstimulated cells.

Statistical Analysis.

Data are represented as the mean±standard error. One-way ANOVA tests (Kruskal-Wallis) was performed for the antibody titer and T cell proliferation using GraphPad Prism software. Student T test was performed for protection studies. A probability (P) value of ≤0.001 was considered statistically significant.

rBmHAT Vaccination does not Induce any Adverse Reactions in Macaques.

The injection sites were monitored closely for signs of any adverse reactions (redness, swelling, etc.) for 7 days post-immunization. There were no adverse reactions in any of the vaccinated or control animals. Clinical monitoring showed no dramatic loss of body weight (>10% of the original weight), changes in eating habits or any other behavioral changes. Temperature measurements obtained daily following immunizations did not show any significant variations. Temperature measurements were also performed at regular intervals using implanted transponders. There were no significant variations in the body temperature in vaccinated and control animals.

The lymph nodes in the left and right leg of all animals were monitored weekly starting approximately 2 weeks prior to challenge (to establish a baseline) and throughout the challenge period. The lymph nodes were measured with a caliper and observed for edema. The measurements showed an overall increase in the mean size of the inguinal lymph nodes in both legs during the 5-8 week post-challenge period in all groups. Compared to the baseline (14.5 mm) the lymph node size in control animals were 22±1 mm and rBmHAT group were 26.2±1 mm. Following this period, the sizes of the lymph nodes decreased to near pre-challenge levels in all macaques.

Challenge with B. malayi L3 did not alter the body temperature in macaques. Analyses of the serum chemistry and hematology (CBC) values showed that they were all in the normal range for all cell types except for a slight increase in the eosinophil counts following L3 challenge in infected animals.

All Three Antigens in the Multivalent Vaccine Construct were Immunogenic in Macaques.

Analysis of the IgG antibody titer in vaccinated macaques showed that all the macaques developed high titers (1:40,000) of IgG antibodies after third immunization against rBmHAT. The titer of antibodies against each of the three component antigens in the vaccine construct was then analyzed. All macaques developed high titers of IgG antibodies against rBmHSP12.6 (1:16,000), rBmALT2 (1:24,000) and rBmTSP-LEL (1:16,000). There were slight individual variations in the titer of antibodies between each vaccinated macaques. On a comparative basis, macaque #5242, #5258 and #5259 showed the highest titer of IgG antibodies against the component antigens (except anti-rBmHSP12.6 antibodies in macaque #5258 and anti-rBmTSP antibodies in macaque #5259). Macaque #4996 and 5254 developed only low titers of antibodies to rBmALT2 and rBmTSP (Table 14).

TABLE 14

| | Antibody Titer | | | |
|---|---|---|---|---|
| Animal ID | rBmHSP12.6 | rBmALT2 | rBmTSP | rBmHAT |
| 4996 | 6400 | 3200 | 16000* | 40000 |
| 5242 | 16000* | 24000** | 16000* | 40000 |
| 5254 | 6400 | 800 | 12800* | 40000 |
| 5258 | 6400 | 24000** | 16000* | 40000 |
| 5259 | 16000* | 24000** | 6400 | 40000 |

Macaques were immunized with 200 µg of rBmHAT with alum adjuvant. Anti-rBmHAT antibodies against rBmHSP12.6, rBmALT2, rBmTSP LEL or rBmHAT were evaluated. Each animal differed in the antibody titer against each antigen.
*$P < 0.05$ and
**$P < 0.001$ statistically significant antibody IgG antibody titer compared to other animals.

Isotype analysis showed that nearly all of the antibodies were of IgG1 isotype against all the four antigens tested (rBmHSP, rBmALT2, rBmTSP and rBmHAT). Levels of IgG2, IgG3, IgA and IgE did not show any significant difference from the background values.

rBmHAT Responding Cells were Present in the PBMC of Immunized Rhesus Macaques.

To determine the antigen specific proliferative responses, PBMC was collected four weeks after the final vaccination. Cell proliferation was determined after stimulating CFSE labeled PBMC with rBmHAT proteins for 5 days and counting the labeled cells in a flow cytometer. These results showed that the proliferation frequency of antigen-responding cells in the immunized animals were 3-fold higher (stimulation index 6.1±0.86) compared to the control animals (stimulation index 2.2±1.42). As expected, PBMC from all the animals showed robust proliferative responses (stimulation index 87.4±0) upon stimulation with pan-T mitogen, PHA. PBMC cultured in control medium had only low-level proliferation following 5-day incubation. The proliferation frequency value for each sample was obtained by subtracting the medium alone control value.

Frequency of CFSE-labeled CD3+, CD4+ and CD8+ PBMC proliferating in response to antigen stimulation were determined by flow cytometry. These studies showed that there was an increase in the proliferation of antigen-responding T cells in all immunized macaques compared to control macaques. Subset analysis showed that in immunized animals approximately 12.7% of the antigen responding T cells were CD4+ cells and 7.9% of T cells were CD8+ subsets. Background proliferation in the presence of rBmHAT antigen in the PBMC of control animals were 1.4% for CD4+ cells and 2.3% for CD8+ cells.

Antigen Responding Cells in the PBMC of Immunized Monkeys Secrete IFN-γ.

Antigen responding cells in the spleen of rBmHAT immunized mice and gerbils predominantly secreted high levels of IFN-γ. Therefore, it was determined whether macaques also show a similar response after immunization but before challenge. These studies showed that PBMC from three immunized macaques (#5242, #5258 and #5259) all secreted significant amounts of IFN-γ when stimulated with rBmHAT antigen (Table 15). Culture supernatants of PBMC from macaque #4996 and #5254 only had background levels of IFN-γ similar to that of the PBMC from control macaques.

TABLE 15

| IFN-γ Secretion (pg/ml) | | | |
|---|---|---|---|
| Animal ID | Control (alum only) | Animal ID | rBmHAT + alum |
| 4995 | 0 | 4996 | 0 |
| 5240 | 0 | 5242 | 62.5 |
| 5249 | 0 | 5254 | 0 |
| 5252 | 0 | 5258 | 62.5 |
| 5253 | 0 | 5259 | 62.5 |

Anti-rBmHAT Antibodies in the Sera of Immunized Macaques can Participate in the Killing of B. malayi L3.

To determine the protective ability of anti-rBmHAT antibodies in the sera of immunized macaques, an in vitro ADCC assay was performed. Results showed that the PBMC from vaccinated macaque were able to participate in the killing of 35% of B. malayi L3 (Table 16). When sera from individual macaques were evaluated maximum killing potential in the ADCC was 45% in the sera of macaque #5258. Sera from macaque #5242 and #5259 also showed significant killing potential with 38% and 35% killing respectively. Sera from macaque #4996 and #5259 had the least ADCC property with 25% and 31% killing respectively. No larval death occurred when sera from control macaques were used in these assays.

TABLE 16

| Animal ID | Live L3$^a$ | Dead L3$^a$ | % Larval Death$^a$ | Mean % Larval Death |
|---|---|---|---|---|
| 4995 | 10 | 0 | 0 | 0 (control) |
| 5240 | 10 | 0 | 0 | |
| 5249 | 10 | 0 | 0 | |
| 5252 | 10 | 0 | 0 | |
| 5253 | 10 | 0 | 0 | |
| 4996 | 7.5 ± 0.6 | 1.5 ± 0.6 | 25 ± 5.2* | 35% ± 6.1* (immunized) |
| 5242 | 6.5 ± 0.6 | 4 ± 0.6 | 38 ± 6.9* | |

TABLE 16-continued

| Animal ID | Live L3[a] | Dead L3[a] | % Larval Death[a] | Mean % Larval Death |
|---|---|---|---|---|
| 5254 | 6.5 ± 1 | 3 ± 0.6 | 31 ± 7.4* | |
| 5258 | 6.5 ± 1.5 | 5 ± 0.6 | 45 ± 6.3* | |
| 5259 | 7 ± 1.2 | 3.5 ± 1.2 | 35 ± 11.5* | |

[a]Results are presented as Mean ± SD of five wells.
Significant larval death *(P < 0.05) compared to other macaques. Control wells were L3 incubated with media, cells alone or sera alone.

Immunization with rBmHAT Conferred Partial Protection in Macaques.

One month after the final vaccination, all 10 monkeys were challenged with 500 B. malayi L3 and screened for the appearance of Mf in the peripheral blood circulation. A Knott test and PCR analysis was used to detect Mf. The Knott test was performed weekly from week 5 post-challenge until the animals became positive. In these studies, challenged macaques became positive for Mf starting from week 10 post-challenge. During weeks 11-20 post challenge, three of the control macaques became positive for Mf. Unfortunately, the remaining two control macaques remained negative through the end of the study. In the vaccinated group, three of the macaques (#5242, #5254 and #5259) remained negative throughout the study. However, two of the vaccinated macaques (#4996 and #5258) became positive for Mf. To further confirm the infection, a PCR analysis was performed, where Hha1 antigen-specific primers were used to amplify for the presence of Mf-specific DNA in the blood of infected monkeys. PCR analysis confirmed infections in macaque #5249 and #4996. The other three positive animals identified by Knott technique were negative by PCR.

rBmHAT Responding Cells were Present in the PBMC of Immunized Rhesus Macaques after Challenge.

PBMC collected weeks post challenge was stimulated with rBmHAT to determine the antigen-specific T cell response. PBMC of three animals #5242 (S.I.—0.928±0.01), #5258 (S.I.—1.091±0.16) and #5256 (S.I.—1.0181±0.13) from the vaccinated group that were negative for Mf showed significant proliferation upon rBmHAT stimulation. Whereas, two of the vaccinated animals #4996 (S.I.—0.258±0.12) and #5254 (S.I.—0.379±0.03) positive for Mf did not show significant proliferation upon rBmHAT stimulation. No significant proliferation was observed in any of the control animals #4995 (S.I.—0.280±0.03), 5240 (S.I.—0.415±0.09), 5249 (S.I.—0.300±0.26), 5252 (S.I.—0.507±0.03) or 5253 (S.I.—0.475±0.25). S.I of PBMC stimulated with Concanavalin was in the range of 2.0-3.8.

Eosinophil Numbers were High in Infected Macaques Showing Mf.

Microfilaremic individuals show high eosinophil counts in their blood (Pearlman, et al. (1993) Exp. Parasitol. 76:200-8; Pearlman, et al. (1993) J. Immunol. 151:4857-64). A similar finding was observed in rhesus macaques as well. Absolute counts of eosinophils were determined on weeks 13, 9, and 5 prior to challenge, on the day of challenge and on weeks 1, 5, 10, and 14 post-challenge. The results showed that there was an increase in the frequency of eosinophil numbers in the peripheral blood of microfilaremic macaques around 10 weeks post-challenges. One macaque (#5259) that was negative for Mf also showed some eosinophilia. Eosinophil counts were 10-fold higher in control macaques that had microfilariae in their peripheral blood.

High Titer of Antigen-Specific IgG Antibodies and Elevated Antigen-Specific Secretion of IFN-γ from PBMC Correlated with Protection in the Immunized Macaques.

Since two of the macaques in the immunized group showed presence of infection following challenge, vaccine-induced immune responses were compared in the two infected macaques with similar responses in the three uninfected macaques within the immunized group. Values before and after challenge were compared. Values before challenge eliminated any bias due to the challenge of parasites. Comparative immunological values are presented in Table 17.

TABLE 17

| Macaque Group | Animal ID | PBMC Proliferation, Mean S.I. ± S.D. (n = 3) | |
|---|---|---|---|
| | | Stimulated with ConA | Stimulated with rBmHAT |
| Control (immunized with alum) | 4995 | 3.260 ± 0.01 | 0.280 ± 0.03 |
| | 5240 | 3.090 ± 0.58 | 0.415 ± 0.09 |
| | 5249 | 2.982 ± 0.24 | 0.300 ± 0.26 |
| | 5252 | 3.674 ± 0.83 | 0.507 ± 0.03 |
| | 5253 | 2.582 ± 0.72 | 0.475 ± 0.25 |
| rBmHAT (immunized with rBmHAT + alum) | 4996 | 3.874 ± 0.47 | 0.258 ± 0.12 |
| | 5242 | 2.170 ± 0.43 | 0.928 ± 0.001** |
| | 5254 | 2.068 ± 0.18 | 0.379 ± 0.03 |
| | 5258 | 3.304 ± 0.64 | 1.091 ± 0.16** |
| | 5259 | 2.883 ± 0.27 | 1.0181 ± 0.13** |

**Significant proliferation of PBMC
**(P < 0.001) compared to PBMC from other macaques.

Results showed that the titer of IgG antibodies was significantly high in the three immunized macaques that did not develop the infection after the challenge. Similarly, PBMC from the same three macaques secreted higher levels of IFN-γ when stimulated with the rBmHAT antigen. PBMC from the two immunized macaques that developed the infection after challenge were unable to secrete similar levels of IFN-γ in response to rBmHAT stimulation. An ELISPOT assay was performed using PBMC from vaccinated and control macaques. Results showed that in all the infected macaques there was a significant increase in the number of antigen-specific IL-10 secreting cells compared to IFN-γ secreting cells. When the ratios of IFN-γ to IL-10 secreting cells in the PBMC of immunized macaques were compared, there was a significant increase in the IL-10 secreting cells in the two vaccinated macaques that showed infection (Table 18). These findings suggest a clear correlation between the type immune responses elicited and the failure to establish infection in the vaccinated macaques.

TABLE 18

| | Immunological values before L3 challenge | | | | Immunological values after L3 challenge | |
|---|---|---|---|---|---|---|
| | Antibody titer of >12,000 | | | | | Ratio of IFN-γ:IL-10 |
| Animal ID | rBmHSP | rBmALT2 | rBmTSP LEL | IFN-γ | Mf | secreting cells |
| 4995[a] | − | − | − | − | + | 1:3 |
| 5240[a] | − | − | − | − | − | 1:1 |
| 5249[a] | − | − | − | − | + | 1:11 |
| 5252[a] | − | − | − | − | − | 1:0.01 |
| 5253[a] | − | − | − | − | + | 1:13 |
| 4996[b] | − | − | + | − | + | 1:4 |
| 5242[b] | + | + | + | + | − | 1:0.003 |
| 5254[b] | − | − | + | − | + | 1:2 |

TABLE 18-continued

| | Immunological values before L3 challenge | | | | | Immunological values after L3 challenge |
|---|---|---|---|---|---|---|
| | Antibody titer of >12,000 | | | | | Ratio of IFN-γ:IL-10 |
| Animal ID | rBmHSP | rBmALT2 | rBmTSP LEL | IFN-γ | Mf | secreting cells |
| 5258[b] | + | + | + | + | − | 1:0.001 |
| 5259[b] | + | + | − | + | − | 1:0.02 |

[a]Control, immunized with alum.
[b]rBmHAT, immunized with rBmHAT + alum.

Example 8: Valency Comparisons

Monovalent, bivalent and trivalent vaccination trials of recombinant heat shock protein 12.6 (rHSP12.6), abundant larval transcript-2 (rALT-2) and tetraspanin large extracellular loop (rTSP-LEL) proteins were compared. Recombinant proteins were prepared as described herein. The bivalent vaccines and multivalent vaccine (SEQ ID NO:70) were produced as fusion proteins. Mice (N=5) were immunized subcutaneously using a protein prime-boost vaccine regimen. Immunized and control animals were challenged with live third stage infective larvae (L3) of *B. malayi* using a micropore chamber method. After 48 hours of implantation, animals were sacrificed and the chambers were recovered from peritoneal cavity. Contents of each chamber were emptied and larvae were examined microscopically at 100× to assess larval death. The results of this analysis are presented in Table 19.

TABLE 19

| Group | Protein Vaccine | Percent Larval Death (protection) |
|---|---|---|
| Control | Alum | 9 ± 3.4 |
| Monovalent | rHSP12.6 (rH) | 58 ± 7.8 |
| | rALT-2 (rA) | 78 ± 3.7 |
| | rTSP LEL (rT) | 49 ± 2.2 |
| Bivalent | rHA | 81 ± 6.5 |
| | rAT | 72 ± 1.1 |
| | rHT | 68 ± 4.4 |
| Multivalent | rHAT | 95 ± 3.1 |

The results indicate that the multivalent vaccine synergistically enhanced the protective immune responses in vaccinated animals compared to monovalent and bivalent vaccines.

*B. malayi* parasite does not mature into adults in mice. However, vaccine-induced protection against adult worm establishment can be determined in jirds. Therefore, monovalent, bivalent and trivalent vaccines were evaluated in jirds. Animals (N=10) were immunized subcutaneously with recombinant proteins. Jirds were challenged with 100 *B. malayi* L3s and worm establishment was determined on day 95 after challenge. Percent protection values were calculated as the percent reduction in worm establishment compared with control jirds. The results of this analysis are presented in Table 20.

TABLE 20

| Group | Protein Vaccine | Percent Protection |
|---|---|---|
| Control | Alum | 15.2 ± 3.3 |
| Monovalent | rHSP12.6 (H) | 70.0 ± 12.6 |
| | rALT-2 (A) | 72.7 ± 8.8 |
| | rTSP LEL (T) | 68.1 ± 2.4 |
| Bivalent | rHA | 83.3 ± 3.3 |
| | rAT | 77.1 ± 12.3 |
| | rHT | 70.2 ± 11.8 |
| Multivalent | rHAT | 90.2 ± 9.1 |

The results indicate that the multivalent vaccine synergistically enhanced the protective immune responses in vaccinated animals compared to monovalent and bivalent vaccines.

Example 8: Vaccine Comparisons

Monovalent, bivalent and multivalent vaccines of this disclosure were compared in mice, jirds and mastomys. Animals were immunized as described, challenged with *B. malayi* L3 and worm establishment was determined. The results of these analyses are presented in Table 21. Of note, rBmHAX immunization gave 98% protection in mice and 97% protection in jirds. These findings show that both rBmHAT and rBmHAX are excellent vaccine candidates for lymphatic filariasis.

TABLE 21

| | Mice* | | Jirds | | Mastomys | |
|---|---|---|---|---|---|---|
| Group | Test | Control | Test | Control | Test | Control |
| rWbALT2[a] | 73 ± 3.7% | 2 ± 0% | 73 ± 1% | 0 ± 1% | 71.66 ± 8.8% | 4.2 ± 1.3% |
| rBmHSP[a] | 58 ± 7.8% | 0 ± 0% | 61 ± 0% | 4 ± 0% | 69.97 ± 12.6% | 2.1 ± 0.2% |
| rWbTSP[a] | 49 ± 2.2% | 3 ± 1% | 33 ± 2% | 1 ± 1% | 68.13 ± 2.4% | 1.1 ± 1.1% |
| rBmTPX[a] | 48 ± 2.1% | 0 ± 0% | 52 ± 2.5% | 0 ± 0% | ND | ND |
| rWbGST[a] | 49 ± 3.1% | 2 ± 1% | 61 ± 1% | 0 ± 0% | ND | ND |
| rWbHA[b] | 81 ± 6.5% | 3 ± 3.2% | ND | ND | 83.25 ± 3.3% | 7.2 ± 1.1% |
| rWbAT[b] | 72 ± 1.1% | 1 ± 2.1% | ND | ND | 77.13 ± 12.3% | 5.4 ± 2.3% |
| rWbHT[b] | 68 ± 4.4% | 6 ± 3.8% | ND | ND | 70.23 ± 11.8% | 7.1 ± 3.3% |
| rBmAX[b] | 74 ± 3.3% | 0 ± 0% | 80 ± 3.5 | 0 ± 0% | ND | ND |
| rWbGA[b] | 68 ± 2.5% | 2 ± 4.1% | 72 ± 3.3% | 0 ± 0% | ND | ND |

TABLE 21-continued

| | Mice* | | Jirds | | Mastomys | |
|---|---|---|---|---|---|---|
| Group | Test | Control | Test | Control | Test | Control |
| rBmHAT[c] | 98 ± 2.1% | 4 ± 3.3% | 95 ± 3.5% | 2 ± 1% | 95.23 ± 9.1% | 4.4 ± 1.2% |
| rBmHAX[c]** | 98 ± 1.2% | 3 ± 1.0% | 97 ± 2.1% | 0 ± 0% | ND | ND |

[a]Monovalent vaccine. Wb, *W. bancrofti*. Bm, *B. malayi*.
[b]Bivalent vaccine. H, HSP. A, ALT2. T, TSP. X, TPX. G, GST.
[c]Trivalent vaccine.
*Animals were immunized s/c with four injections of 15 μg of the vaccine antigen plus 15 μg of alum at 2 week intervals. Test animals were challenged with 100 L3 and worm establishment was determined on day 90 post-challenge. The micropore chamber challenge method was used in mice. In this method, 20 L3 were placed in a micropore chamber, which was implanted into the peritoneal cavity. After 48 hours the chambers were removed to determine live and dead larvae.
Data mean + SD.
N = 10.
**Mice and jirds were immunized with 15 μg of rBmHAX plus 15 μg of alum with a total of four immunizations at 2 weeks interval. Blood was collected on day 0, 14, 28, 42, 49 and 70 to monitor the titer of antibodies against each of the component antigens. The following titers were observed on day 49 (ALT-2 1:60,000; HSP 1:40,000, TPX 1:40,000). All the animals were challenged on day 49 with 20 *B. malayi* L3 for mice and 100 *B. malayi* L3 for jirds. Worm establishment or worm death in immunized animals was observed at 48 hours after surgical implantation of L3 in mice or 90 days after infection in jirds. Percent protection was calculated as described herein.

---

What is claimed is:

1. A method for immunizing an animal against filariasis administering to an animal in need thereof a vaccine comprising
   (a) *Brugia malayi* Abundant Larval Transcript protein comprising SEQ ID NO: 78; and
   (b) a *Brugia malayi* Small heat shock protein 12.6 comprising SEQ ID NO: 81; a *Brugia malayi* Tetraspanin protein comprising SEQ ID NO: 82; a *Brugia malayi* Thioredoxin Peroxidase 2 protein comprising SEQ ID NO:83, or a combination thereof,
   wherein each of the proteins of (a) and (b) elicits an immune response in an animal thereby immunizing the animal against filariasis.

2. The method of claim 1, further comprising administering an adjuvant.

3. The method of claim 1, wherein the filariasis is caused by a *Brugia* filarial nematode.

\* \* \* \* \*

SEQUENCE LISTING

<160> NUMBER OF SEQ ID NOS: 86

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1
cgcggatcca tggaagagaa ggtggtg                                        27

<210> SEQ ID NO 2
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 2
ccggaattct cacttgtcgt tggtg                                          25

<210> SEQ ID NO 3
<211> LENGTH: 12
<212> TYPE: PRT
<213> ORGANISM: Brugia malayi

<400> SEQUENCE: 3

Trp Ser Ala Glu Gln Trp Asp Trp Pro Leu Gln His
1               5                   10

<210> SEQ ID NO 4
<211> LENGTH: 10
<212> TYPE: PRT
<213> ORGANISM: Brugia malayi

<400> SEQUENCE: 4

Glu Val Ile Lys Thr Asn Thr Asn Asp Lys
1               5                   10

<210> SEQ ID NO 5
<211> LENGTH: 8
<212> TYPE: PRT
<213> ORGANISM: Brugia malayi

```
<400> SEQUENCE: 5

Ser Arg Ala Glu His Tyr Gly Glu
1               5

<210> SEQ ID NO 6
<211> LENGTH: 11
<212> TYPE: PRT
<213> ORGANISM: Brugia malayi

<400> SEQUENCE: 6

Lys Leu Pro Ser Asp Val Asp Thr Lys Thr Leu
1               5                   10

<210> SEQ ID NO 7
<211> LENGTH: 9
<212> TYPE: PRT
<213> ORGANISM: Brugia malayi

<400> SEQUENCE: 7

Phe Thr Pro Lys Glu Ile Glu Val Lys
1               5

<210> SEQ ID NO 8
<211> LENGTH: 8
<212> TYPE: PRT
<213> ORGANISM: Brugia malayi

<400> SEQUENCE: 8

Ile Glu Val Lys Val Ala Gly Asp
1               5

<210> SEQ ID NO 9
<211> LENGTH: 8
<212> TYPE: PRT
<213> ORGANISM: Brugia malayi

<400> SEQUENCE: 9

Val Gly Leu Asp Ala Ser Phe Phe
1               5

<210> SEQ ID NO 10
<211> LENGTH: 9
<212> TYPE: PRT
<213> ORGANISM: Brugia malayi

<400> SEQUENCE: 10

Gly Leu Asp Ala Ser Phe Phe Thr Pro
1               5

<210> SEQ ID NO 11
<211> LENGTH: 9
<212> TYPE: PRT
<213> ORGANISM: Brugia malayi

<400> SEQUENCE: 11

Val Lys Val Ala Gly Asp Asn Leu Val
1               5

<210> SEQ ID NO 12
<211> LENGTH: 9
<212> TYPE: PRT
<213> ORGANISM: Brugia malayi

<400> SEQUENCE: 12
```

Lys Leu Pro Ser Asp Val Asp Thr Lys
1               5

<210> SEQ ID NO 13
<211> LENGTH: 9
<212> TYPE: PRT
<213> ORGANISM: Brugia malayi

<400> SEQUENCE: 13

Lys Thr Leu Thr Ser Asn Leu Thr Lys
1               5

<210> SEQ ID NO 14
<211> LENGTH: 9
<212> TYPE: PRT
<213> ORGANISM: Brugia malayi

<400> SEQUENCE: 14

Val Ile Lys Thr Asn Thr Asn Asp Lys
1               5

<210> SEQ ID NO 15
<211> LENGTH: 9
<212> TYPE: PRT
<213> ORGANISM: Brugia malayi

<400> SEQUENCE: 15

Asp Thr Lys Thr Leu Thr Ser Asn Leu
1               5

<210> SEQ ID NO 16
<211> LENGTH: 9
<212> TYPE: PRT
<213> ORGANISM: Brugia malayi

<400> SEQUENCE: 16

Phe Phe Thr Pro Lys Glu Ile Glu Val
1               5

<210> SEQ ID NO 17
<211> LENGTH: 9
<212> TYPE: PRT
<213> ORGANISM: Brugia malayi

<400> SEQUENCE: 17

Val Gly Leu Asp Ala Ser Phe Phe Thr
1               5

<210> SEQ ID NO 18
<211> LENGTH: 9
<212> TYPE: PRT
<213> ORGANISM: Brugia malayi

<400> SEQUENCE: 18

Lys Arg Gly His Leu Val Ile Ala Ala
1               5

<210> SEQ ID NO 19
<211> LENGTH: 9
<212> TYPE: PRT
<213> ORGANISM: Brugia malayi

<400> SEQUENCE: 19

Gly Glu Ile Lys Arg Glu Ile Ser Arg

<210> SEQ ID NO 20
<211> LENGTH: 9
<212> TYPE: PRT
<213> ORGANISM: Brugia malayi

<400> SEQUENCE: 20

Ser Phe Phe Thr Pro Lys Glu Ile Glu
1               5

<210> SEQ ID NO 21
<211> LENGTH: 9
<212> TYPE: PRT
<213> ORGANISM: Brugia malayi

<400> SEQUENCE: 21

Arg Glu Ile Ser Arg Thr Tyr Lys Leu
1               5

<210> SEQ ID NO 22
<211> LENGTH: 9
<212> TYPE: PRT
<213> ORGANISM: Brugia malayi

<400> SEQUENCE: 22

Gly Glu Ile Lys Arg Glu Ile Ser Arg
1               5

<210> SEQ ID NO 23
<211> LENGTH: 9
<212> TYPE: PRT
<213> ORGANISM: Brugia malayi

<400> SEQUENCE: 23

Ala Glu His Tyr Gly Glu Ile Lys Arg
1               5

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 24
ccggaattct cacttgtcgt tggtg                                    25

<210> SEQ ID NO 25
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 25
cgcggatcca ccgtgatcca ttgtcg                                   26

<210> SEQ ID NO 26
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 26
aactgcagct gttttccatt tccattc                              27

<210> SEQ ID NO 27
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 27
aactgcagat gggtaacaag ctcctcatcg                           30

<210> SEQ ID NO 28
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 28
cgcgaattcg gcgcactgcc aacctgc                              27

<210> SEQ ID NO 29
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 29
cgcgaattca ccatggtcct ggag                                 24

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 30
gctctagatc agtccttctg gctag                                25

<210> SEQ ID NO 31
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 31
cgggatccat ggaagaaaag gtagtg                               26

<210> SEQ ID NO 32
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 32
ccctcgagtg ctttctttt ggcagc                                26

<210> SEQ ID NO 33
<211> LENGTH: 30
<212> TYPE: DNA

<213> ORGANISM: Artificial sequence
<220> FEATURE:
<223> OTHER INFORMATION: Synthetic oligonucleotide

<400> SEQUENCE: 33
ccctcgagat gaataaactt ttaatagcat         30

<210> SEQ ID NO 34
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 34
gggtacccgc gcattgccaa ccc         23

<210> SEQ ID NO 35
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 35
ggggtacccc ggcaaggatc aatttaaaa         29

<210> SEQ ID NO 36
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 36
cggaattctc aatcttttg agatgaat         28

<210> SEQ ID NO 37
<211> LENGTH: 129
<212> TYPE: PRT
<213> ORGANISM: Brugia malayi

<400> SEQUENCE: 37

Met Gly Asn Lys Leu Leu Ile Ala Phe Gly Leu Val Ile Leu Phe Val
1               5                   10                  15

Thr Leu Pro Cys Val Ser Glu Ser Asp Glu Glu Phe Asp Asp Ser Ala
            20                  25                  30

Ala Asp Asp Thr Asp Asp Ser Glu Ala Gly Gly Gly Ser Glu Gly Gly
        35                  40                  45

Asp Glu Tyr Val Thr Lys Gly Glu Phe Val Glu Thr Asp Gly Lys Lys
    50                  55                  60

Lys Glu Cys Ser Ser His Glu Ala Cys Tyr Asp Gln Arg Glu Pro Gln
65                  70                  75                  80

Ala Trp Cys Arg Leu Ser Glu Asn Gln Ala Trp Thr Asp Arg Gly Cys
                85                  90                  95

Phe Cys Glu Asp Lys Leu His Ser Cys Val Ile Glu Arg Thr Asn Asn
            100                 105                 110

Gly Lys Leu Glu Tyr Ser Tyr Cys Ala Pro Glu Ala Gly Trp Gln Cys
        115                 120                 125

Ala

```
<210> SEQ ID NO 38
<211> LENGTH: 572
<212> TYPE: DNA
<213> ORGANISM: Brugia malayi

<400> SEQUENCE: 38
ggtttattac cccaagtttg agggaggaga aaatgaataa acttttaata gcattcggtt      60
tggtaattct ttttgtgaca ctcccgtgtg tatcagaatc agacgaagag ttcgatgact     120
ccgcagccga tgacaccgac dacagcgagg ccggaggtgg tagtgaagga ggtgatgaat     180
atgtaaccaa aggggaattt gttgaaactg atggcaaaaa gaaagagtgc tcttcgcacg     240
aagcttgcta cgatcaacgt gaaccacaag cgtggtgcag actgagcgag aatcaggcat     300
ggactgacag aggctgcttc tgcgaagata agttgcattc gtgcgtcatc gaaagaacga     360
acaatggtaa attggagtat tcgtactgtg caccgaagc aggttggcaa tgcgcatagg      420
aatgaatcag tctttgatac taccaacttt ccatccattt cctacacttt tcaaatttaa     480
ttctttctaa caaataacat ttaactttgg ttttaccgtt attttattaa atattggaaa     540
tatgtgcgac aaaaaaaaaa aaaaaaaaaa aa                                  572

<210> SEQ ID NO 39
<211> LENGTH: 126
<212> TYPE: PRT
<213> ORGANISM: Brugia malayi

<400> SEQUENCE: 39

Met Asn Asn Leu Leu Ile Ala Ile Ser Leu Val Ile Leu Val Ile
1               5                   10                  15

Phe Pro Ser Lys Ser Asp Leu Glu Ile Asp Asp Ser Ser Asp Ser Asp
            20                  25                  30

Tyr Ala His Ser Asn Asp Asp Tyr Asn Glu Glu Asp Glu Tyr
        35                  40                  45

Thr Thr Lys Gly Glu Phe Val Glu Thr Asp Gly Lys Trp Lys Asn Cys
    50                  55                  60

Ser Ser His Ala Asp Cys Tyr Asp Tyr Arg Glu Pro Ile Ala Trp Cys
65                  70                  75                  80

Lys Pro Thr Ala Asn Gln Phe Trp Thr Asp Lys Gly Cys Phe Cys Glu
                85                  90                  95

Asp Met Leu Tyr Ser Cys Val Ile Glu Arg Thr Asn Asn Gly Lys Leu
            100                 105                 110

Glu Tyr Ser Tyr Cys Thr Ser Lys Glu Asn Trp Gln Cys Leu
        115                 120                 125

<210> SEQ ID NO 40
<211> LENGTH: 381
<212> TYPE: DNA
<213> ORGANISM: Brugia malayi

<400> SEQUENCE: 40
atgaataatc tattgatagc aatcagttta gtaattcttc ttgtgatatt cccatcaaaa      60
tcagatttag aaattgatga ttcctcagac agtgattatg ctcatagcaa tgacgacgat     120
tacaatgaag aagaagatga atatacgacc aaaggagaat ttgttgaaac tgatggcaaa     180
tggaagaatt gcagttctca tgcagattgc tatgattatc gtgaaccaat agcttggtgc     240
aaacccactg caaatcaatt ttggacagac aaaggttgct tctgtgaaga tatgttgtat     300
tcatgtgtga tcgaaagaac gaacaatggc aaattagaat attcatattg tacatccaaa     360
```
gaaaactggc aatgtttata a 381

<210> SEQ ID NO 41
<211> LENGTH: 128
<212> TYPE: PRT
<213> ORGANISM: Wuchereria bancrofti

<400> SEQUENCE: 41

Met Asn Lys Leu Leu Ile Ala Phe Gly Leu Val Ile Leu Leu Val Thr
1 5 10 15

Leu Pro Cys Ala Ser Glu Ser Asp Glu Glu Phe Asp Asp Gly Ser Asn
20 25 30

Asp Glu Thr Asp Asp Lys Glu Asp Glu Gly Asn Ser Glu Gly Gly Asp
35 40 45

Glu Tyr Val Thr Lys Gly Glu Val Val Glu Thr Asp Gly Lys Lys Lys
50 55 60

Glu Cys Ser Ser His Glu Ala Cys Tyr Asp Gln Arg Glu Pro Gln Ala
65 70 75 80

Trp Cys Arg Pro Asn Glu Asn Gln Ser Trp Thr Asp Lys Gly Cys Phe
85 90 95

Cys Glu Asp Lys Leu His Ser Cys Val Ile Glu Arg Lys Asn Asn Gly
100 105 110

Lys Leu Glu Tyr Ser Tyr Cys Ala Pro Glu Ala Gly Trp Gln Cys Ala
115 120 125

<210> SEQ ID NO 42
<211> LENGTH: 387
<212> TYPE: DNA
<213> ORGANISM: Wuchereria bancrofti

<400> SEQUENCE: 42
atgaataaac ttttaatagc attcggttta gtaattcttc ttgtgacact tccgtgtgca 60
tcagaatcag acgaagagtt cgatgacggc tcaaatgatg agaccgacga caaagaggac 120
gaaggtaata gtgaaggagg tgatgaatat gtaaccaaag gagaagttgt tgaaactgat 180
ggcaagaaga aagagtgctc ttcgcacgaa gcttgttacg atcaacgtga accacaagcg 240
tggtgtagac cgaacgagaa tcagtcgtgg actgacaaag gttgcttctg cgaagataag 300
ttgcattcgt gcgtcatcga aagaaagaac aacggtaaat tggagtattc gtattgcgca 360
cctgaagcgg gttggcaatg cgcgtag 387

<210> SEQ ID NO 43
<211> LENGTH: 83
<212> TYPE: PRT
<213> ORGANISM: Loa loa

<400> SEQUENCE: 43

Met Ile His Asn Gly Gly Tyr Gln Lys Leu Lys Val Lys Leu Arg Lys
1 5 10 15

Lys Glu Cys Lys Ser His Glu Ala Cys Tyr Asp Gln Arg Glu Pro Gln
20 25 30

Asp Trp Cys Arg Leu Asn Glu Asn Gln Ser Trp Thr Asp Lys Gly Cys
35 40 45

Tyr Cys Asp Asp Lys Leu His Ser Cys Ile Ile Glu Arg Lys Asn Gly
50 55 60

Gly Lys Leu Glu Tyr Ala His Cys Ala Pro Glu Gln Gly Trp Lys Cys
65 70 75 80

-continued

Pro Ser Lys

<210> SEQ ID NO 44
<211> LENGTH: 252
<212> TYPE: DNA
<213> ORGANISM: Loa loa

<400> SEQUENCE: 44

```
atgattcata acggtggata ccaaaaatta aaagtcaaat tgaggaagaa agaatgcaag      60
tctcatgaag cttgctacga tcaacgtgaa ccacaagact ggtgcagatt gaacgaaaat     120
caatcgtgga cagacaaagg ttgctactgt gacgataagt tgcattcatg cattattgag     180
cgcaagaacg gtggcaagtt ggaatatgcg cactgtgcgc tgaacaagg atggaaatgt      240 ccaagcaagt aa                                                         252
```

<210> SEQ ID NO 45
<211> LENGTH: 229
<212> TYPE: PRT
<213> ORGANISM: Brugia malayi

<400> SEQUENCE: 45

```
Met Val His Gly Cys Gly Asn Arg Thr Leu Lys Phe Leu Phe Phe Thr
1               5                   10                  15

Ala Asn Leu Leu Thr Cys Ala Phe Gly Ala Leu Leu Phe Gly Ile Ser
            20                  25                  30

Leu Trp Ala Tyr His Asp Glu Asn Phe Leu Gln Lys Leu Glu Lys Val
        35                  40                  45

Gln Glu Ile His Lys Glu Tyr Ser Pro Glu Leu Thr Gln His Gln Ile
    50                  55                  60

Gly Leu Trp Leu Leu Ile Ile Ile Gly Ala Ser Ile Phe Leu Val Gly
65                  70                  75                  80

Phe Leu Gly Cys Cys Gly Ala Ile Cys Glu Ser Thr Lys Leu Leu Ala
                85                  90                  95

Leu Phe Ser Ile Ile Val Leu Ile Leu Ala Ile Leu Glu Val Ala Ser
            100                 105                 110

Ile Val Leu Ile Ile Ala Gly Lys Asp Gln Phe Lys Asn Ala Leu Tyr
        115                 120                 125

Asn Leu Leu Ser Lys Thr Gly Glu Ser Glu Asp Glu Met Gln His Phe
    130                 135                 140

Lys Pro Ile Glu Asp Leu Phe Gln Cys Cys Gly Pro Thr Asn Glu Thr
145                 150                 155                 160

Met Val Arg Tyr Ile Glu Asn Gly Leu Cys Glu Asp Glu Leu Arg Asn
                165                 170                 175

Lys Pro Asn Cys Phe Ala Val Ile Ser Asp His Phe Asp Ser Ser Gln
            180                 185                 190

Lys Asp Ile Ile Lys Ile Ser Val Val Leu Ile Ile Asp Leu Leu
        195                 200                 205

Ala Leu Phe Ser Thr Ser Met Leu Tyr Lys Ala Phe Arg Tyr Gln Thr
    210                 215                 220

Pro Tyr Tyr Tyr Ala
225
```

<210> SEQ ID NO 46
<211> LENGTH: 690
<212> TYPE: DNA
<213> ORGANISM: Brugia malayi

<400> SEQUENCE: 46

```
atggttcacg gctgtggtaa tcgaacattg aaattttat ttttcactgc aaatttatta      60
acttgtgcat ttggtgcact tcttttggc atttcattat gggcttatca tgatgaaaat     120
tttttgcaaa aattagaaaa agtacaggaa atacataaag aatattctcc tgaactaaca    180
caacatcaaa taggattgtg ttattaata attattggtg catccatatt tcttgttggt    240
tttctcggtt gttgtggtgc gatatgtgaa agtaccaagc tattggcttt attttctatt    300
attgtattaa ttcttgcaat acttgaagtt gcttcgatag tacttataat tgctggcaag    360
gatcaattta aaaatgcttt atataattta ctatcaaaaa ctggcgaatc agaagatgaa    420
atgcaacatt ttaaacctat cgaagattta ttccaatgtt gtggtccaac aaatgaaaca    480
atggttcgat acatcgagaa tggcttatgt gaggatgaat taagaaataa accgaattgt    540
ttcgcagtaa tatccgatca ttttgattca tctcaaaaag atatcattaa aatttccgtc    600
gttttaataa ttattgattt gcttgcatta ttttctacat ctatgcttta taaagcattt    660
cgctatcaaa caccatacta ttatgcttaa                                     690
```

<210> SEQ ID NO 47
<211> LENGTH: 230
<212> TYPE: PRT
<213> ORGANISM: Loa loa

<400> SEQUENCE: 47

```
Met Val His Gly Cys Gly Asn Arg Met Val Lys Phe Leu Phe Phe Thr
1               5                   10                  15

Ala Asn Leu Leu Ile Cys Leu Phe Gly Ala Leu Ile Phe Gly Phe Ser
                20                  25                  30

Leu Trp Ala Asn Leu Asp Glu Asp Phe Ala Leu Lys Leu Glu Glu Thr
            35                  40                  45

Arg Lys Ile His Lys Glu Asp Phe Asn Val Leu Ala Arg Tyr Gln Ala
        50                  55                  60

Ala Phe Trp Val Leu Val Ile Gly Ala Phe Leu Phe Leu Val Gly
65                  70                  75                  80

Phe Leu Gly Cys Cys Gly Ala Met Cys Glu Asn Ile Met Leu Leu Thr
                85                  90                  95

Ala Phe Phe Ile Ile Ile Leu Ile Leu Thr Thr Ile Glu Val Gly Ala
            100                 105                 110

Val Ile Phe Ala Ile Thr Ser Lys Gly Gln Phe Lys Ser Val Leu His
        115                 120                 125

Arg Leu Leu Ser Glu Ala Gly Lys Ala Glu Asp Lys Tyr Leu Pro Asn
    130                 135                 140

Leu Lys Pro Ile Glu Asp Leu Phe Tyr Cys Cys Gly Ala Thr Gln Glu
145                 150                 155                 160

Thr Met Asn Arg Tyr Met Glu His Gly Leu Cys Glu Gly Glu Leu Lys
                165                 170                 175

Asn Lys Pro Asp Cys Phe Thr Ala Ile Ser Asp Tyr Leu Glu Ser Thr
            180                 185                 190

Gly Glu Ala Val Val Val Phe Ala Phe Phe Leu Leu Ile Ile Glu Leu
        195                 200                 205

Phe Ala Leu Val Ser Thr Cys Ile Leu Cys Lys Ala Phe Arg Tyr Gly
    210                 215                 220

Arg Pro Tyr Tyr Tyr Ala
225                 230
```

<210> SEQ ID NO 48
<211> LENGTH: 693
<212> TYPE: DNA
<213> ORGANISM: Loa loa

<400> SEQUENCE: 48

| | | |
|---|---|---|
| atggttcacg gttgtggcaa tcgaatggtg aaatttttat ttttcactgc aaatttactg | 60 |
| atctgtttat ttggcgcact tattttggc ttctcattat gggctaattt ggatgaagat | 120 |
| tttgcgctaa agctggaaga acgagaaaa atacataaag aagattttaa tgtgctggca | 180 |
| agatatcaag cagcattttg ggtattggtt gttattgggg cattcttgtt tctcgttggt | 240 |
| ttcctcggct gttgtggtgc aatgtgtgaa aatatcatgt tgttgactgc atttttcatc | 300 |
| ataatactaa ttcttacaac aatcgaagtt ggcgcggtaa tatttgcaat cactagcaag | 360 |
| ggccaattta aaagtgtttt acataggcta ctatcagaag ctggtaaagc agaagacaaa | 420 |
| tacttgccga atttaaaacc catcgaagat ctgttttatt gctgtggtgc aacgcaagaa | 480 |
| acgatgaacc ggtacatgga acatggctta tgtgaaggaa aattgaagaa taagccggac | 540 |
| tgcttcacgg caatatcgga ttatttggag tcaaccggag aagcggtcgt cgtatttgca | 600 |
| ttcttttttgc taattatcga gttgtttgct ttagttccca catgtatact atgtaaagca | 660 |
| ttccgttatg gaaggccata ctactatgct taa | 693 |

<210> SEQ ID NO 49
<211> LENGTH: 113
<212> TYPE: PRT
<213> ORGANISM: Brugia malayi

<400> SEQUENCE: 49

Met Glu Glu Lys Val Val Glu Leu Thr His Asn Trp Ser Ala Glu Gln
1               5                   10                  15

Trp Asp Trp Pro Leu Gln His Asn Asp Glu Val Ile Lys Val Thr Asn
            20                  25                  30

Thr Asn Asp Lys Phe Glu Val Gly Leu Asp Ala Ser Phe Phe Thr Pro
        35                  40                  45

Lys Glu Ile Glu Val Lys Val Ala Gly Asp Asn Leu Val Ile His Cys
    50                  55                  60

Arg His Glu Ser Arg Ala Glu His Tyr Gly Glu Ile Lys Arg Glu Ile
65                  70                  75                  80

Ser Arg Thr Tyr Lys Leu Pro Ser Asp Val Asp Thr Lys Thr Leu Thr
                85                  90                  95

Ser Asn Leu Thr Lys Arg Gly His Leu Val Ile Ala Ala Lys Lys Lys
            100                 105                 110

Ala

<210> SEQ ID NO 50
<211> LENGTH: 342
<212> TYPE: DNA
<213> ORGANISM: Brugia malayi

<400> SEQUENCE: 50

| | | |
|---|---|---|
| atggaagaaa aggtagtgga actaacgcac aactggagtg cggagcagtg ggattggccc | 60 |
| ttacagcaca cgatgaggt gattaaagta accaacacga atgataagtt tgaagtcggt | 120 |
| ttggatgcat cattcttcac gccgaaggaa atcgaggtaa aagttgctgg cgataatctg | 180 |
| gtcattcact gcagacatga atcacgtgcc gagcattatg gagaaattaa acgtgaaatt | 240 |

-continued

```
agtcgtacct ataagcttcc gtcggatgta gatacgaaga ctctgacatc aaatttgacc    300
aagcgaggac atttggtcat cgctgccaaa aagaaagcat ga                        342

<210> SEQ ID NO 51
<211> LENGTH: 165
<212> TYPE: PRT
<213> ORGANISM: Onchocerca volvulus

<400> SEQUENCE: 51

Gln Thr Ser Pro Met Glu Arg Phe Ile Val Asn Leu Leu Asp Ser Thr
1               5                   10                  15

Phe Asp Asp Arg Ser Ser Arg Pro Leu His Ser Val Ala Pro Tyr Trp
            20                  25                  30

Leu His Gln Pro Glu Leu Asn Glu Cys Asn Ile Gly Asn Ser Leu Gly
        35                  40                  45

Glu Val Ile Asn Glu Lys Asp Lys Phe Ala Val Arg Ala Asp Val Ser
    50                  55                  60

His Phe His Pro Lys Glu Leu Ser Val Ser Val Arg Asp Arg Glu Leu
65                  70                  75                  80

Val Ile Glu Gly His His Glu Glu Arg Thr Asp Pro Ala Gly His Gly
                85                  90                  95

Ser Ile Glu Arg His Phe Ile Arg Lys Tyr Val Leu Pro Glu Glu Val
            100                 105                 110

Gln Pro Asp Thr Ile Glu Ser His Leu Ser Asp Lys Gly Val Leu Thr
        115                 120                 125

Ile Ser Ala Asn Lys Thr Ala Ile Gly Thr Thr Ala Ser Arg Asn Ile
    130                 135                 140

Pro Ile Arg Ala Ser Pro Lys Glu Pro Glu Ala Asn Gln Lys Ser Ala
145                 150                 155                 160

Ile Asn Asp Ala Lys
                165

<210> SEQ ID NO 52
<211> LENGTH: 574
<212> TYPE: DNA
<213> ORGANISM: Onchocerca volvulus

<400> SEQUENCE: 52
caaacttcac cgatggaacg tttcatagtg aaccttcttg acagtacatt cgatgacaga     60
tcatctcgac cgctccattc tgttgcacca tattggcttc atcaaccgga actgaatgaa    120
tgtaatatcg gaaattctct cggcgaggta ataaatgaga aagacaagtt tgcagttcga    180
gctgatgttt ctcatttcca tccgaaggaa ctttcggtgt cggttcgaga tcgtgaacta    240
gttattgaag gtcaccatga agagcgtacc gatccggcag gacatggtag tattgaacgt    300
cacttcattc gaaaatatgt cttgccagaa gaagtgcagc ctgacacgat cgaatcacat    360
ttgtccgata aaggagtgtt gacaattagc gcaaacaaaa cagctattgg cacgactgca    420
tcacgaaaca ttccaattcg agcatctcca aaagaaccgg aagcaaatca gaaatcggca    480
ataaatgatg caaagtaaaa agaagtagaa attccggata tatttcattc tttattttat    540
acgctttttt tttcttttt tgttcatttt aaag                                  574

<210> SEQ ID NO 53
<211> LENGTH: 113
<212> TYPE: PRT
<213> ORGANISM: Loa loa
```

<400> SEQUENCE: 53

```
Met Glu Glu Lys Val Leu Glu Leu Thr His Asn Trp Ser Ala Glu Gln
1               5                   10                  15

Trp Asp Trp Pro Leu Gln His Asn Asp Val Ile Lys Val Thr Asn
                20                  25                  30

Thr Asn Asp Lys Phe Glu Val Ser Leu Asp Ala Ser Phe Thr Pro
            35                  40                  45

Lys Glu Ile Glu Val Lys Val Ala Gly Asp Asn Leu Val Ile His Cys
        50                  55                  60

Arg His Glu Ser Arg Ala Asp Gln Tyr Gly Glu Ile Lys Arg Glu Ile
65                  70                  75                  80

Ser Arg Thr Tyr Lys Leu Pro Ser Asp Ile Asp Thr Lys Thr Leu Thr
                85                  90                  95

Ser Thr Leu Thr Lys Arg Gly His Leu Val Ile Val Ala Lys Lys Lys
            100                 105                 110

Ala
```

<210> SEQ ID NO 54
<211> LENGTH: 342
<212> TYPE: DNA
<213> ORGANISM: Loa loa

<400> SEQUENCE: 54

| | |
|---|---:|
| atggaagaaa aggtattgga actaacgcat aattggagtg ccgagcagtg ggattggccc | 60 |
| ttgcagcata acgatgacgt gattaaagtg accaatacga atgataagtt tgaagtcagt | 120 |
| ctggatgctt cattcttcac accgaaggaa atcgaggtga agttgctgg tgataatctg | 180 |
| gtcattcact gcagacatga atcacgtgcc gaccaatacg gtgaaattaa acgtgaaatt | 240 |
| agtcgtacct ataagcttcc gtcggatatt gatacgaaga ccctgacatc aactttgacc | 300 |
| aaaagaggac atctggtcat cgttgccaaa aagaaggcat ga | 342 |

<210> SEQ ID NO 55
<211> LENGTH: 220
<212> TYPE: PRT
<213> ORGANISM: Brugia malayi

<400> SEQUENCE: 55

```
Met Leu Phe Phe Val Ile Phe Ser Ile Thr Ile Ala Val Val Ala Gly
1               5                   10                  15

Phe Glu Cys Pro Gly Gly Arg Leu Thr Pro Gln Gln Arg Lys Asp Ile
                20                  25                  30

Val Arg Gln Asn Asn Lys Phe Arg Ser Leu Leu Ile His Gly Lys Leu
            35                  40                  45

Lys Asn Arg Asn Gly Thr Tyr Met Pro Arg Gly Lys Asn Met Leu Leu
        50                  55                  60

Leu Lys Trp Ser Cys Gln Leu Glu Asn Ser Ala Gln Arg Trp Ala Asn
65                  70                  75                  80

Gln Cys Val Phe Gly His Ser Pro Arg Asn Gln Arg Gln Gly Ile Gly
                85                  90                  95

Glu Asn Val Tyr Ala Tyr Trp Ser Ser Glu Ser Val Glu Lys Leu Arg
            100                 105                 110

Asn Thr Ala Gly Thr Glu Ala Gly Lys Ser Trp Trp Ser Glu Leu Pro
        115                 120                 125

Lys Leu Tyr Lys Gln Asn Pro Ser Asn Asn Leu Thr Asp Asp Val Ala
        130                 135                 140
```

Arg Gln Gly Val Leu His Phe Thr Gln Met Ala Trp Gly Lys Thr His
145                 150                 155                 160

Lys Ile Gly Cys Gly Ile Ala Thr Asn Cys Asp Gly Arg Thr Leu
            165                 170                 175

Ile Ala Ile Cys His Tyr Ser Pro Ala Gly Asn Met Leu Lys Glu Leu
            180                 185                 190

Ile Tyr Glu Leu Gly Glu Pro Cys Lys Thr Asp Ser Asp Cys Asn Thr
            195                 200                 205

Lys Lys Cys Ala Lys Lys Ser Gly Leu Cys Arg Lys
            210                 215                 220

<210> SEQ ID NO 56
<211> LENGTH: 897
<212> TYPE: DNA
<213> ORGANISM: Brugia malayi

<400> SEQUENCE: 56
gcacgagata ttttcaaagc taacagtata cattccacca aaaaactcgg caaaatgtta      60
tttttcgtta tattttccat cacgattgct gttgtggcag gttttgaatg tccaggaggt     120
cgactaacac cacagcaacg taaagatatc gttcgtcaga acaataaatt tcgttcatta     180
ctaattcatg gaaaacttaa aaataggaat ggtacatata tgccacgcgg caagaatatg     240
ttgctactga agtggagttg tcagttagaa aattctgcgc aaagatgggc aaatcaatgc     300
gtctttgggc actctccgag aaatcaaaga caaggaatcg gtgaaaatgt ctatgcctac     360
tggtcatcag aaagcgtcga aaagcttaga ataccgctg gtacggaagc cggcaaaagt     420
tggtggtcag aacttccgaa actgtacaaa cagaatcctt cgaacaatct gactgatgat     480
gttgccagac aaggtgtttt acatttcaca cagatggcct ggggtaaaac gcataaaatt     540
ggttgtggta tagcaacaaa ctgcgatggt ggtcgcacac tcatagctat tgccattat      600 tcacccgctg gaaatatgct aaaagaactg atatatgagc ttggcgaacc atgcaaaacg     660
gatagcgatt gtaacacaaa gaaatgtgcc aaaaaatctg gattgtgtag aaaatgaaag     720
agagtttaaa gtttcacttt ttgcactctt aattttggtt ttatattata aaactgagaa     780
ttattacaaa catatttatt ggctattata agataaaaaa gttccttgaa attcttctca     840
aataaaattt ctctctgata aaagcatgaa acaaaaaaaa aaaaaaaaaa aaaaaaa        897

<210> SEQ ID NO 57
<211> LENGTH: 220
<212> TYPE: PRT
<213> ORGANISM: Wuchereria bancrofti

<400> SEQUENCE: 57

Met Leu Leu Phe Val Ile Phe Ser Ala Thr Ile Val Ala Val Ala Ala
1 5 10 15

Phe Glu Cys Pro Gly Gly Gln Leu Thr Pro Gln Gln Arg Lys Asp Ile
20 25 30

Val Arg Gln Asn Asn Lys Phe Arg Ser Leu Leu Ile Arg Gly Lys Leu
35 40 45

Lys Asn Arg Asn Gly Thr Tyr Met Pro Arg Gly Lys Asn Met Leu Gln
50 55 60

Leu Thr Trp Ser Cys Gln Leu Glu Asn Ser Ala Gln Arg Trp Ala Asn
65 70 75 80

Gln Cys Val Phe Gly His Ser Pro Arg Asn Gln Arg Gln Gly Ile Gly
85 90 95

```
Glu Asn Val Tyr Ala Tyr Trp Ser Ser Ala Ser Val Glu Asn Leu Arg
            100                 105                 110

Lys Thr Ala Gly Thr Glu Ala Gly Lys Ser Trp Trp Ser Glu Leu Pro
        115                 120                 125

Glu Leu Tyr Lys His Asn Pro Ser Asn Asn Leu Thr Asp Asp Val Ser
    130                 135                 140

Arg Gln Gly Val Leu His Phe Thr Gln Met Ala Trp Gly Lys Thr His
145                 150                 155                 160

Lys Ile Gly Cys Gly Ile Ala Thr Asn Cys Asp Gly Gly Arg Thr Leu
                165                 170                 175

Ile Thr Ile Cys His Tyr Ser Pro Ala Gly Asn Ile Leu Lys Asn Leu
            180                 185                 190

Ile Tyr Glu Leu Gly Glu Pro Cys Lys Lys Asp Gly Asp Cys Asn Thr
        195                 200                 205

Lys Lys Cys Ala Lys Lys Ser Gly Leu Cys Arg Lys
    210                 215                 220

<210> SEQ ID NO 58
<211> LENGTH: 873
<212> TYPE: DNA
<213> ORGANISM: Wuchereria bancrofti

<400> SEQUENCE: 58
ggaattcggc acgagcgaca tcttctgtta tcaaatatat tttcaaagct aacagtgtac      60
attctgccag aaaatcccgc aaaatgttac ttttcgtcat attttctgca actattgttg     120
ctgtggcggc ttttgaatgt ccaggaggtc aactaacacc gcaacaacgt aaagatatcg     180
ttcgtcagaa caataaattt cgttcattac tgattcgtgg aaaacttaaa aataggaatg     240
gtacatatat gccacgcggc aagaatatgt tgcaactgac atggagttgt cagttagaaa     300
attctgcgca aagatgggca aatcagtgcg tctttggaca ctcaccgaga aatcaaagac     360
aaggaatcgg tgaaaatgtt tacgcttact ggtcgtcagc aagcgttgaa aatcttagaa     420
aaaccgctgg tacggaagcc ggcaaaagtt ggtggtcaga acttccggaa ctgtacaaac     480
acaatccttc gaacaatctg actgacgatg tttccaggca aggtgttttg catttcacac     540
agatggcttg ggtaaaacg cataaaattg gttgtggtat tgctacaaac tgtgatggtg     600
gtcgcacact cataactatt tgccattatt cgcccgctgg aaatatactg aaaaatctga     660
tatatgagct tggcgaaccg tgcaaaaagg atggcgattg taacacaaag aaatgtgcga     720
aaaaatctgg attgtgcaga aagtgaaaga atttgaagag tttcaccttc tcatttctaa     780
ttttggtttt gtatcataaa actgacaatt attacaaaca tatttattgg ctattatggg     840
ataaagaagt ttcttgaaaa aaaaaaaaaa aaa                                  873

<210> SEQ ID NO 59
<211> LENGTH: 220
<212> TYPE: PRT
<213> ORGANISM: Onchocerca volvulus

<400> SEQUENCE: 59

Met Ile Leu Phe Ile Ile Phe Pro Ala Ile Val Val Ala Val Thr Gly
1               5                   10                  15

Tyr Asn Cys Pro Gly Gly Lys Leu Thr Ala Leu Glu Arg Lys Lys Ile
            20                  25                  30

Val Gly Gln Asn Asn Lys Tyr Arg Ser Asp Leu Ile Asn Gly Lys Leu
        35                  40                  45
```

```
Lys Asn Arg Asn Gly Thr Tyr Met Pro Arg Gly Lys Asn Met Leu Glu
    50                  55                  60

Leu Thr Trp Asp Cys Lys Leu Glu Ser Ser Ala Gln Arg Trp Ala Asn
65                  70                  75                  80

Gln Cys Ile Phe Gly His Ser Pro Arg Gln Gln Arg Glu Gly Val Gly
                85                  90                  95

Glu Asn Val Tyr Ala Tyr Trp Ser Ser Val Ser Val Glu Gly Leu Lys
            100                 105                 110

Lys Thr Ala Gly Thr Asp Ala Gly Lys Ser Trp Trp Ser Lys Leu Pro
        115                 120                 125

Lys Leu Tyr Glu Asn Asn Pro Ser Asn Asn Met Thr Trp Lys Val Ala
    130                 135                 140

Gly Gln Gly Val Leu His Phe Thr Gln Met Ala Trp Gly Lys Thr Tyr
145                 150                 155                 160

Lys Ile Gly Cys Gly Val Ala Thr Gln Cys Asp Gly Gly Arg Thr Leu
                165                 170                 175

Ile Val Ile Cys His Tyr Ser Pro Gly Gly Asn Met Val Gly Glu Val
            180                 185                 190

Ile Tyr His Arg Gly Asn Pro Cys Lys Val Asp Lys Asp Cys Tyr Thr
        195                 200                 205

Lys Lys Cys Leu Ser Lys Ser Gly Leu Cys Arg Lys
    210                 215                 220
```

<210> SEQ ID NO 60
<211> LENGTH: 883
<212> TYPE: DNA
<213> ORGANISM: Onchocerca volvulus

<400> SEQUENCE: 60

```
gcattttcta aagtgacatc ttctgttatt atcaaatata tttctgagat taacagctta      60
tattctatcg gaaaattccg caaaatgata cttttcatca tcttccctgc aattgtcgtc     120
gcggtgacgg gttataattg tccaggaggt aaactaacag cactggaacg taaaaaaatc     180
gttggtcaga ataataaata tcgttcggat ttgattaatg gaaagcttaa gaatagaaat     240
ggtacataca tgccaagagg caagaatatg ttggaactga catgggattg taaattggaa     300
agttcggcac aaaggtgggc caatcagtgt atctttggac attcaccaag acaacaaaga     360
gagggagttg gtgaaaatgt ttatgcgtac tggtcatcag tatcagttga aggtcttaaa     420
aaaactgctg gtacggatgc tgggaaaagc tggtggtcaa agcttccaaa attatatgaa     480
aataaccctt cgaataatat gacttggaaa gttgccggtc aaggtgtttt gcatttcaca     540
caaatggctt ggggtaagac ttataaaatt ggttgcggtg ttgcaacaca atgtgatggt     600
ggtagaacac ttattgttat ttgtcactat tctcctggtg gaaatatggt tggagaggtg     660
atataccacc gaggtaatcc gtgtaaagtc gacaaagatt gctatacgaa aaaatgttta     720
tcaaaatctg gactgtgcag aaaatgaaaa tttttcgctt ttcttcattt aattctcggc     780
tatatatctc ctatattaat ttttcagcaa aaaagctata aagaaatatt cataattaaa     840
taaatatagt aattattatg aaataaaaaa ttaagttctg ctc                       883
```

<210> SEQ ID NO 61
<211> LENGTH: 220
<212> TYPE: PRT
<213> ORGANISM: Loa loa

<400> SEQUENCE: 61

```
Met Leu Cys Ser Phe Met Phe Ala Ala Ile Ile Ile Ala Val Glu Gly
1               5                   10                  15

Tyr Arg Cys Gln Gly Gly Arg Leu Thr Pro Glu Gln Arg Lys Ala Ile
            20                  25                  30

Val Ile Gln Asn Asn Lys Phe Arg Ser Gln Leu Ile Arg Gly Glu Leu
        35                  40                  45

Lys Asn Lys Ala Gly Glu Phe Met Pro Arg Gly Lys Asn Met Leu Arg
    50                  55                  60

Met Arg Trp Ser Cys Ser Leu Glu Tyr Ser Ala Gln Arg Trp Ala Asp
65                  70                  75                  80

Arg Cys Ile Phe Gly His Ser Pro Arg Asp Gln Arg Asn Asn Ile Gly
                85                  90                  95

Glu Asn Val Tyr Ala Tyr Trp Ser Ser Gly Ser Val Glu Gly His Arg
            100                 105                 110

Lys Thr Ala Gly Thr Asp Ala Gly Lys Asn Trp Trp Ser Glu Leu Pro
        115                 120                 125

Glu Arg Tyr Gly Ser Asn Pro Ser Asn Asn Leu Thr Ala Gln Val Ser
    130                 135                 140

Ser Gln Gly Val Leu His Phe Thr Gln Met Ala Trp Gly Lys Thr Tyr
145                 150                 155                 160

Lys Ile Gly Cys Gly Ile Ala Thr Asn Cys Asp Gly Gly Arg Thr Leu
                165                 170                 175

Met Val Ile Cys His Tyr Ser Pro Ala Gly Asn Met Leu Lys Glu Leu
            180                 185                 190

Ile Tyr Glu Leu Gly Glu Pro Cys Lys Lys Asn Asn Asp Cys Tyr Thr
        195                 200                 205

Lys Lys Cys Ser Val Lys Ser Gly Leu Cys Asn Lys
    210                 215                 220

<210> SEQ ID NO 62
<211> LENGTH: 663
<212> TYPE: DNA
<213> ORGANISM: Loa loa

<400> SEQUENCE: 62
atgttatgtt ccttcatgtt tgcagcaatt atcattgctg tggaaggtta tcgatgtcaa      60
ggaggtcgac taacaccgga gcaacgtaaa gcatccgtta ttcaaaataa taaattccgt    120
tcgcaactga tccgtggcga gcttaagaac aaagctggtg aatttatgcc acgtggcaag    180
aatatgttga gaatgagatg gagttgttcg ctggaatatt ccgcgcagag atgggcagat    240
agatgtatct ttggacactc accaagagat caaagaaaca atatcggtga aaatgtctat    300
gcttactggt catcaggaag cgttgaaggt catagaaaaa ctgctggtac agatgctggt    360
aaaaattggt ggtcagaact tccggaacgg tacggatcta atccttcaaa taatttgact    420
gctcaagttt ccagccaagg tgttttgcat ttcacacaga tggcttgggg taaaacgtac    480
aaaattggct gtggtattgc tacaaactgc gatggtggca ggacactaat ggtcatttgc    540
cattattcgc cagctgggaa tatgttgaaa gagcttatat atgagcttgg cgaaccatgc    600
aagaagaaca atgattgtta taccaagaag tgttcagtca agtctggatt gtgcaacaag    660
tga                                                                  663

<210> SEQ ID NO 63
<211> LENGTH: 89
<212> TYPE: PRT
```

<213> ORGANISM: Brugia malayi

<400> SEQUENCE: 63

Met Ile Leu Glu Val Ala Ser Ile Val Leu Ile Ala Gly Lys Asp
1               5                   10                  15

Gln Phe Lys Asn Ala Leu Tyr Asn Leu Leu Ser Lys Thr Gly Glu Ser
            20                  25                  30

Glu Asp Glu Met Gln His Phe Lys Pro Ile Glu Asp Leu Phe Gln Cys
        35                  40                  45

Cys Gly Pro Thr Asn Glu Thr Met Val Arg Tyr Ile Glu Asn Gly Leu
    50                  55                  60

Cys Glu Asp Glu Leu Arg Asn Lys Pro Asn Cys Phe Ala Val Ile Ser
65                  70                  75                  80

Asp His Phe Asp Ser Ser Gln Lys Asp
                85

<210> SEQ ID NO 64
<211> LENGTH: 53
<212> TYPE: PRT
<213> ORGANISM: Brugia malayi

<400> SEQUENCE: 64

Val Ile His Cys Arg His Glu Ser Arg Ala Glu His Tyr Gly Glu Ile
1               5                   10                  15

Lys Arg Glu Ile Ser Arg Thr Tyr Lys Leu Pro Ser Asp Val Asp Thr
            20                  25                  30

Lys Thr Leu Thr Ser Asn Leu Thr Lys Arg Gly His Leu Val Ile Ala
        35                  40                  45

Ala Lys Lys Lys Ala
    50

<210> SEQ ID NO 65
<211> LENGTH: 267
<212> TYPE: DNA
<213> ORGANISM: Brugia malayi

<400> SEQUENCE: 65
atgatcctgg aggtggcctc catcgtgctg atcatcgccg gcaaggacca gttcaagaac     60
gctctgtaca acctgctgtc taagacaggc gagagcgagg acgagatgca gcacttcaag    120
cctatcgagg acctgttcca gtgctgcggc cctaccaacg agaccatggt gaggtacatc    180
gagaacggac tgtgcgagga cgagctgagg aacaagccta actgtttcgc cgtgatctct    240
gaccacttcg attctagcca gaaggac                                         267

<210> SEQ ID NO 66
<211> LENGTH: 162
<212> TYPE: DNA
<213> ORGANISM: Brugia malayi

<400> SEQUENCE: 66
gtcattcact gcagacatga atcacgtgcc gagcattatg gagaaattaa acgtgaaatt     60
agtcgtacct ataagcttcc gtcggatgta gatacgaaga ctctgacatc aaatttgacc    120
aagcgaggac atttggtcat cgctgccaaa aagaaagcat ga                       162

<210> SEQ ID NO 67
<211> LENGTH: 387
<212> TYPE: DNA
<213> ORGANISM: Brugia malayi

<400> SEQUENCE: 67

```
atgggtaaca agctcctcat cgctttcgga ctcgtgatcc tgtttgtcac cctgccttgc     60
gtcagtgaga gcgacgagga gtttgatgac tctgccgctg acgacaccga cgattccgag    120
gccggtggcg gctctgaggg gggcgacgag tacgtgacta agggggagtt tgtggagacc    180
gatggaaaga agaaagagtg ctccagccac gaggcctgtt atgaccagcg ggagcctcag    240
gcttggtgca ggctgtctga gaatcaggcc tggactgata gaggctgttt ctgtgaggac    300
aagctgcatt cttgcgtgat tgagcggact aataatggca agctggaata cagctactgc    360
gctcccgagg caggttggca gtgcgcc                                        387
```

<210> SEQ ID NO 68
<211> LENGTH: 153
<212> TYPE: DNA
<213> ORGANISM: Wuchereria bancrofti

<400> SEQUENCE: 68

```
atggtcattc actgcaggca cgagagcaga gccgagcact acggcgagat caaaagagag     60
atcagcagga catacaagct gccctcagac gtggacacta agactctgac tagcaatctg    120
accaagaggg gccacctggt catcgctgcc aag                                 153
```

<210> SEQ ID NO 69
<211> LENGTH: 267
<212> TYPE: DNA
<213> ORGANISM: Wuchereria bancrofti

<400> SEQUENCE: 69

```
atgatcctgg aggtggcctc catcgtgctg atcatcgccg gcaaggacca gttcaagaac     60
gctctgtaca acctgctgtc taagacaggc gagagcgagg acgagatgca gcacttcaag    120
cctatcgagg acctgttcca gtgctgcggc cctaccaacg agaccatggt gaggtacatc    180
gagaacggac tgtgcgagga cgagctgagg aacaagccta actgtttcgc cgtgatctct    240
gaccacttcg attctagcca gaaggac                                       267
```

<210> SEQ ID NO 70
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 70

```
Met Glu Glu Lys Val Val Glu Leu Thr His Asn Trp Ser Ala Glu Gln
1               5                   10                  15
Trp Asp Trp Pro Leu Gln His Asn Asp Glu Val Ile Lys Val Thr Asn
            20                  25                  30
Thr Asn Asp Lys Phe Glu Val Gly Leu Asp Ala Ser Phe Phe Thr Pro
        35                  40                  45
Lys Glu Ile Glu Val Lys Val Ala Gly Asp Asn Leu Val Ile His Cys
    50                  55                  60
Arg His Glu Ser Arg Ala Glu His Tyr Gly Glu Ile Lys Arg Glu Ile
65                  70                  75                  80
Ser Arg Thr Tyr Lys Leu Pro Ser Asp Val Asp Thr Lys Thr Leu Thr
                85                  90                  95
Ser Asn Leu Thr Lys Arg Gly His Leu Val Ile Ala Ala Lys Lys Lys
            100                 105                 110
```

Ala Met Gly Asn Lys Leu Leu Ile Ala Phe Gly Leu Val Ile Leu Phe
            115                 120                 125

Val Thr Leu Pro Cys Val Ser Glu Ser Asp Glu Glu Phe Asp Asp Ser
        130                 135                 140

Ala Ala Asp Asp Thr Asp Asp Ser Glu Ala Gly Gly Gly Ser Glu Gly
145                 150                 155                 160

Gly Asp Glu Tyr Val Thr Lys Gly Glu Phe Val Glu Thr Asp Gly Lys
                165                 170                 175

Lys Lys Glu Cys Ser Ser His Glu Ala Cys Tyr Asp Gln Arg Glu Pro
                180                 185                 190

Gln Ala Trp Cys Arg Leu Ser Glu Asn Gln Ala Trp Thr Asp Arg Gly
                195                 200                 205

Cys Phe Cys Glu Asp Lys Leu His Ser Cys Val Ile Glu Arg Thr Asn
        210                 215                 220

Asn Gly Lys Leu Glu Tyr Ser Tyr Cys Ala Pro Glu Ala Gly Trp Gln
225                 230                 235                 240

Cys Ala Met Ile Leu Glu Val Ala Ser Ile Val Leu Ile Ile Ala Gly
                245                 250                 255

Lys Asp Gln Phe Lys Asn Ala Leu Tyr Asn Leu Leu Ser Lys Thr Gly
                260                 265                 270

Glu Ser Glu Asp Glu Met Gln His Phe Lys Pro Ile Glu Asp Leu Phe
            275                 280                 285

Gln Cys Cys Gly Pro Thr Asn Glu Thr Met Val Arg Tyr Ile Glu Asn
            290                 295                 300

Gly Leu Cys Glu Asp Glu Leu Arg Asn Lys Pro Asn Cys Phe Ala Val
305                 310                 315                 320

Ile Ser Asp His Phe Asp Ser Ser Gln Lys Asp
                325                 330

<210> SEQ ID NO 71
<211> LENGTH: 199
<212> TYPE: PRT
<213> ORGANISM: Brugia malayi

<400> SEQUENCE: 71

Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
                20                  25                  30

Gly Gln Phe Lys Gly Lys Tyr Val Val Leu Leu Phe Tyr Pro Leu Asp
            35                  40                  45

Phe Thr Phe Val Cys Pro Thr Glu Ile Ile Ala Phe Ser Asp Arg Ile
        50                  55                  60

Ala Glu Phe Lys Gln Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ala Tyr Thr Asn His Val
            100                 105                 110

Ile Ser Arg Ala Tyr Gly Val Leu Lys Glu Asp Gly Ile Ala Tyr
            115                 120                 125

Arg Gly Leu Phe Ile Ile Asp Pro Lys Gly Ile Leu Gly Gln Ile Thr
            130                 135                 140

Ile Asn Asp Leu Pro Val Gly Arg Ser Val Asp Glu Thr Leu Arg Leu

| | | | | | | | | | | | |
|---|---|---|---|---|---|---|---|---|---|---|---|
|145| | | | |150| | | | |155| |160|

Ile Gln Ala Phe Gln Phe Val Asp Lys His Gly Glu Val Cys Pro Ala
　　　　　　　　165　　　　　　　　　　170　　　　　　　　　175

Asn Trp His Pro Gly Ser Glu Thr Ile Lys Pro Gly Val Lys Glu Ser
　　　　　　　　180　　　　　　　　　185　　　　　　　　　190

Lys Ala Tyr Phe Glu Lys His
　　　　　　　　195

```
<210> SEQ ID NO 72
<211> LENGTH: 713
<212> TYPE: DNA
<213> ORGANISM: Brugia malayi

<400> SEQUENCE: 72
```

| | | | | |
|---|---|---|---|---|
|ggtttaatta|cccaagtttg|aggaagaaaa|gaaaatgaca|cttgctggaa gtaaagcatt|60|
|tattggtcaa|ccagcaccta|atttaaaac|aacagctgtt|gtgaacggtg atttcaagga|120|
|aatttcactt|ggtcaattta|agggaaaata|tgttgttctc|ctcttttatc ctcttgattt|180|
|cactttttgtt|tgtccaacgg|aaataattgc|attttctgat|cgtattgcgg aatttaaaca|240|
|attagatgta|gctgttatgg|catgttcaac|agattcacac|ttttcacatc ttgcatgggt|300|
|aaatactgat|cgaaaaatgg|gtggacttgg|tcaaatgaat|ataccaattt tggcttatac|360|
|aaatcatgta|ataagtcgag|catatggtgt|acttaaagag|gatgatggaa ttgcttatcg|420|
|tggattattc|attattgatc|aaaaggaat|tttggggcaa|atcacaatta acgatcttcc|480|
|agtagggcgt|tctgtagacg|aaactttacg|tttaattcaa|gcttttcagt tgttgacaa|540|
|gcatggtgaa|gtatgtcctg|ctaattggca|tccaggatct|gaaacgatta agcctggtgt|600|
|gaaagaaagt|aaagcatatt|ttgagaaaca|ttaaaaacca|aaaatggttg tacgacatgg|660|
|aattactcag|tggatttttt|tgattaaatt|atatgctgaa|gtaatattaa cca|713|

```
<210> SEQ ID NO 73
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 73
```

Met Glu Glu Lys Val Val Glu Leu Thr His Asn Trp Ser Ala Glu Gln
1　　　　　　　　5　　　　　　　　　10　　　　　　　　　15

Trp Asp Trp Pro Leu Gln His Asn Asp Glu Val Ile Lys Val Thr Asn
　　　　　　　　20　　　　　　　　　25　　　　　　　　　30

Thr Asn Asp Lys Phe Glu Val Gly Leu Asp Ala Ser Phe Phe Thr Pro
　　　　　　35　　　　　　　　　40　　　　　　　　　45

Lys Glu Ile Glu Val Lys Val Ala Gly Asp Asn Leu Val Ile His Cys
　　50　　　　　　　　　55　　　　　　　　　60

Arg His Glu Ser Arg Ala Glu His Tyr Gly Glu Ile Lys Arg Glu Ile
65　　　　　　　　　70　　　　　　　　　75　　　　　　　　　80

Ser Arg Thr Tyr Lys Leu Pro Ser Asp Val Asp Thr Lys Thr Leu Thr
　　　　　　　　85　　　　　　　　　90　　　　　　　　　95

Ser Asn Leu Thr Lys Arg Gly His Leu Val Ile Ala Ala Lys Lys Lys
　　　　　　　100　　　　　　　　　105　　　　　　　　　110

Ala Met Gly Asn Lys Leu Leu Ile Ala Phe Gly Leu Val Ile Leu Phe
　　　　　　115　　　　　　　　　120　　　　　　　　　125

Val Thr Leu Pro Cys Val Ser Glu Ser Asp Glu Glu Phe Asp Asp Ser
　　　　　130　　　　　　　　　135　　　　　　　　　140

Ala Ala Asp Asp Thr Asp Asp Ser Glu Ala Gly Gly Ser Glu Gly
145                 150                 155                 160

Gly Asp Glu Tyr Val Thr Lys Gly Glu Phe Val Glu Thr Asp Gly Lys
                165                 170                 175

Lys Lys Glu Cys Ser Ser His Glu Ala Cys Tyr Asp Gln Arg Glu Pro
            180                 185                 190

Gln Ala Trp Cys Arg Leu Ser Glu Asn Gln Ala Trp Thr Asp Arg Gly
        195                 200                 205

Cys Phe Cys Glu Asp Lys Leu His Ser Cys Val Ile Glu Arg Thr Asn
    210                 215                 220

Asn Gly Lys Leu Glu Tyr Ser Tyr Cys Ala Pro Glu Ala Gly Trp Gln
225                 230                 235                 240

Cys Ala Met Thr Leu Ala Gly Ser Lys Ala Phe Ile Gly Gln Pro Ala
                245                 250                 255

Pro Asn Phe Lys Thr Thr Ala Val Val Asn Gly Asp Phe Lys Glu Ile
                260                 265                 270

Ser Leu Gly Gln Phe Lys Gly Lys Tyr Val Val Leu Leu Phe Tyr Pro
            275                 280                 285

Leu Asp Phe Thr Phe Val Cys Pro Thr Glu Ile Ala Phe Ser Asp
290                 295                 300

Arg Ile Ala Glu Phe Lys Gln Leu Asp Val Ala Val Met Ala Cys Ser
305                 310                 315                 320

Thr Asp Ser His Phe Ser His Leu Ala Trp Val Asn Thr Asp Arg Lys
                325                 330                 335

Met Gly Gly Leu Gly Gln Met Asn Ile Pro Ile Leu Ala Tyr Thr Asn
                340                 345                 350

His Val Ile Ser Arg Ala Tyr Gly Val Leu Lys Glu Asp Asp Gly Ile
            355                 360                 365

Ala Tyr Arg Gly Leu Phe Ile Ile Asp Pro Lys Gly Ile Leu Gly Gln
370                 375                 380

Ile Thr Ile Asn Asp Leu Pro Val Gly Arg Ser Val Asp Glu Thr Leu
385                 390                 395                 400

Arg Leu Ile Gln Ala Phe Gln Phe Val Asp Lys His Gly Glu Val Cys
                405                 410                 415

Pro Ala Asn Trp His Pro Gly Ser Glu Thr Ile Lys Pro Gly Val Lys
                420                 425                 430

Glu Ser Lys Ala Tyr Phe Glu Lys His
            435                 440

<210> SEQ ID NO 74
<211> LENGTH: 530
<212> TYPE: PRT
<213> ORGANISM: Artificial Sequence
<220> FEATURE:
<223> OTHER INFORMATION: Synthetic polypeptide

<400> SEQUENCE: 74

Met Glu Glu Lys Val Val Glu Leu Thr His Asn Trp Ser Ala Glu Gln
1               5                   10                  15

Trp Asp Trp Pro Leu Gln His Asn Asp Glu Val Ile Lys Val Thr Asn
                20                  25                  30

Thr Asn Asp Lys Phe Glu Val Gly Leu Asp Ala Ser Phe Phe Thr Pro
            35                  40                  45

Lys Glu Ile Glu Val Lys Val Ala Gly Asp Asn Leu Val Ile His Cys
50                  55                  60

```
Arg His Glu Ser Arg Ala Glu His Tyr Gly Glu Ile Lys Arg Glu Ile
 65                  70                  75                  80

Ser Arg Thr Tyr Lys Leu Pro Ser Asp Val Asp Thr Lys Thr Leu Thr
                 85                  90                  95

Ser Asn Leu Thr Lys Arg Gly His Leu Val Ile Ala Ala Lys Lys Lys
            100                 105                 110

Ala Met Gly Asn Lys Leu Leu Ile Ala Phe Gly Leu Val Ile Leu Phe
        115                 120                 125

Val Thr Leu Pro Cys Val Ser Glu Ser Asp Glu Phe Asp Asp Ser
    130                 135                 140

Ala Ala Asp Asp Thr Asp Ser Glu Ala Gly Gly Ser Glu Gly
145                 150                 155                 160

Gly Asp Glu Tyr Val Thr Lys Gly Glu Phe Val Glu Thr Asp Gly Lys
                165                 170                 175

Lys Lys Glu Cys Ser Ser His Glu Ala Cys Tyr Asp Gln Arg Glu Pro
            180                 185                 190

Gln Ala Trp Cys Arg Leu Ser Glu Asn Gln Ala Trp Thr Asp Arg Gly
        195                 200                 205

Cys Phe Cys Glu Asp Lys Leu His Ser Cys Val Ile Glu Arg Thr Asn
210                 215                 220

Asn Gly Lys Leu Glu Tyr Ser Tyr Cys Ala Pro Glu Ala Gly Trp Gln
225                 230                 235                 240

Cys Ala Met Thr Leu Ala Gly Ser Lys Ala Phe Ile Gly Gln Pro Ala
                245                 250                 255

Pro Asn Phe Lys Thr Thr Ala Val Val Asn Gly Asp Phe Lys Glu Ile
            260                 265                 270

Ser Leu Gly Gln Phe Lys Gly Lys Tyr Val Val Leu Leu Phe Tyr Pro
        275                 280                 285

Leu Asp Phe Thr Phe Val Cys Pro Thr Glu Ile Ile Ala Phe Ser Asp
290                 295                 300

Arg Ile Ala Glu Phe Lys Gln Leu Asp Val Ala Val Met Ala Cys Ser
305                 310                 315                 320

Thr Asp Ser His Phe Ser His Leu Ala Trp Val Asn Thr Asp Arg Lys
                325                 330                 335

Met Gly Gly Leu Gly Gln Met Asn Ile Pro Ile Leu Ala Tyr Thr Asn
            340                 345                 350

His Val Ile Ser Arg Ala Tyr Gly Val Leu Lys Glu Asp Asp Gly Ile
        355                 360                 365

Ala Tyr Arg Gly Leu Phe Ile Ile Asp Pro Lys Gly Ile Leu Gly Gln
    370                 375                 380

Ile Thr Ile Asn Asp Leu Pro Val Gly Arg Ser Val Asp Glu Thr Leu
385                 390                 395                 400

Arg Leu Ile Gln Ala Phe Gln Phe Val Asp Lys His Gly Glu Val Cys
                405                 410                 415

Pro Ala Asn Trp His Pro Gly Ser Glu Thr Ile Lys Pro Gly Val Lys
            420                 425                 430

Glu Ser Lys Ala Tyr Phe Glu Lys His Met Ile Leu Glu Val Ala Ser
        435                 440                 445

Ile Val Leu Ile Ile Ala Gly Lys Asp Gln Phe Lys Asn Ala Leu Tyr
    450                 455                 460

Asn Leu Leu Ser Lys Thr Gly Glu Ser Glu Asp Glu Met Gln His Phe
465                 470                 475                 480
```

```
Lys Pro Ile Glu Asp Leu Phe Gln Cys Cys Gly Pro Thr Asn Glu Thr
            485                 490                 495

Met Val Arg Tyr Ile Glu Asn Gly Leu Cys Glu Asp Glu Leu Arg Asn
        500                 505                 510

Lys Pro Asn Cys Phe Ala Val Ile Ser Asp His Phe Asp Ser Ser Gln
        515                 520                 525

Lys Asp
    530

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 75
gcgcataaat tcatcagc                                                 18

<210> SEQ ID NO 76
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 76
gcgcaaaact taattacaaa agc                                           23

<210> SEQ ID NO 77
<211> LENGTH: 76
<212> TYPE: PRT
<213> ORGANISM: Brugia malayi

<400> SEQUENCE: 77

Gly Lys Asp Gln Phe Lys Asn Ala Leu Tyr Asn Leu Leu Ser Lys Thr
1               5                   10                  15

Gly Glu Ser Glu Asp Glu Met Gln His Phe Lys Pro Ile Glu Asp Leu
            20                  25                  30

Phe Gln Cys Cys Gly Pro Thr Asn Glu Thr Met Val Arg Tyr Ile Glu
        35                  40                  45

Asn Gly Leu Cys Glu Asp Glu Leu Arg Asn Lys Pro Asn Cys Phe Ala
    50                  55                  60

Val Ile Ser Asp His Phe Asp Ser Ser Gln Lys Asp
65                  70                  75

<210> SEQ ID NO 78
<211> LENGTH: 33
<212> TYPE: PRT
<213> ORGANISM: Brugia malayi

<400> SEQUENCE: 78

Val Ser Glu Ser Asp Glu Glu Phe Asp Asp Ser Ala Ala Asp Asp Thr
1               5                   10                  15

Asp Asp Ser Glu Ala Gly Gly Gly Ser Glu Gly Gly Asp Glu Tyr Val
            20                  25                  30

Thr

<210> SEQ ID NO 79
<211> LENGTH: 25
<212> TYPE: PRT
```

-continued

<213> ORGANISM: Brugia malayi

<400> SEQUENCE: 79

Glu Phe Val Glu Thr Asp Gly Lys Lys Glu Cys Ser Ser His Glu
1               5                   10                  15

Ala Cys Tyr Asp Gln Arg Glu Pro Gln
            20                  25

<210> SEQ ID NO 80
<211> LENGTH: 12
<212> TYPE: PRT
<213> ORGANISM: Brugia malayi

<400> SEQUENCE: 80

Trp Ser Ala Glu Gln Trp Asp Trp Pro Leu Gln His
1               5                   10

<210> SEQ ID NO 81
<211> LENGTH: 11
<212> TYPE: PRT
<213> ORGANISM: Brugia malayi

<400> SEQUENCE: 81

Lys Leu Pro Ser Asp Val Asp Thr Lys Thr Leu
1               5                   10

<210> SEQ ID NO 82
<211> LENGTH: 10
<212> TYPE: PRT
<213> ORGANISM: Brugia malayi

<400> SEQUENCE: 82

Lys Thr Gly Glu Ser Glu Asp Glu Met Gln
1               5                   10

<210> SEQ ID NO 83
<211> LENGTH: 11
<212> TYPE: PRT
<213> ORGANISM: Brugia malayi

<400> SEQUENCE: 83

Phe Ile Gly Gln Pro Ala Pro Asn Phe Lys Thr
1               5                   10

<210> SEQ ID NO 84
<211> LENGTH: 24
<212> TYPE: PRT
<213> ORGANISM: Brugia malayi

<400> SEQUENCE: 84

Gly Glu Val Cys Pro Ala Asn Trp His Pro Gly Ser Glu Thr Ile Lys
1               5                   10                  15

Pro Gly Val Lys Glu Ser Lys Ala
            20

<210> SEQ ID NO 85
<211> LENGTH: 208
<212> TYPE: PRT
<213> ORGANISM: Wuchereria bancrofti

<400> SEQUENCE: 85

Met Ser Tyr Lys Leu Thr Tyr Phe Pro Ile Arg Gly Leu Ala Gl

```
Ile Arg Leu Val Leu Val Asp Gln Gly Ile Lys Phe Thr Asp Asp Arg
            20                  25                  30

Ile Asn Ala Ser Asp Trp Pro Ser Met Lys Ser His Phe His Phe Gly
            35                  40                  45

Gln Leu Pro Cys Leu Tyr Asp Gly Asp His Gln Ile Val Gln Ser Gly
 50                  55                  60

Ala Ile Leu Arg His Leu Ala Arg Lys His Asn Leu Asn Gly Gly Asn
 65                  70                  75                  80

Glu Leu Glu Thr Thr His Ile Asp Met Phe Cys Glu Gly Ile Arg Asp
            85                  90                  95

Leu His Thr Lys Tyr Ala Lys Met Ile Tyr Gln Ala Tyr Asp Thr Glu
            100                 105                 110

Lys Asp Ser Tyr Ile Lys Asp Ile Leu Pro Val Glu Leu Ala Lys Phe
            115                 120                 125

Glu Lys Leu Leu Ala Thr Arg Asp Asp Gly Lys Asn Phe Ile Leu Gly
 130                 135                 140

Glu Lys Ile Ser Tyr Val Asp Phe Val Leu Phe Glu Glu Leu Asp Ile
145                  150                 155                 160

His Gln Ile Leu Asp Pro His Cys Leu Asp Lys Phe Pro Leu Leu Lys
            165                 170                 175

Ala Tyr His Gln Arg Met Glu Asp Arg Pro Gly Leu Lys Glu Tyr Cys
            180                 185                 190

Lys Gln Arg Asn Arg Ala Lys Ile Pro Val Asn Gly Asn Gly Lys Gln
            195                 200                 205

<210> SEQ ID NO 86
<211> LENGTH: 627
<212> TYPE: DNA
<213> ORGANISM: Wuchereria bancrofti

<400> SEQUENCE: 86
atgagttata aactgacgta ttttcctatc cgaggcttgg ctgaaccaat tcgtttagta      60
ctggttgatc aaggtataaa gtttactgat gatcgtatca atgcaagtga ttggccttct     120
atgaaatcac actttcattt tggacaacta ccttgtcttt acgatggtga tcatcaaatt     180
gtgcagtccg gtgctattct gagacatctt gctcgcaaac ataatttaaa tggtggaaat     240
gaactggaaa cgacacatat tgatatgttc tgtgaaggca tccgtgatct acataccaaa     300
tatgcaaaaa tgatttacca ggcttatgac acagaaaagg attcctacat aaaggatata     360
ttgccagtag agctggcgaa atttgaaaag ttgcttgcta cacgagacga tggaaaaaat     420
ttcattctag gagaaaagat ttcatacgta gatttcgtcc ttttcgaaga acttgacatt     480
catcagatcc tggatccgca ctgcttggat aaatttccac tcttaaaagc ttaccatcaa     540
cgaatggaag atagacctgg acttaaggag tactgcaagc agcgtaatag agcaaaaata     600
ccagtgaatg gaaatggaaa acagtga                                         627
```